US011499171B2

(12) United States Patent
Mihara et al.

(10) Patent No.: US 11,499,171 B2
(45) Date of Patent: Nov. 15, 2022

(54) METHOD OF PRODUCING 13-HYDROXY-9(Z)-OCTADECENOIC ACID

(71) Applicant: AJINOMOTO CO., INC., Tokyo (JP)

(72) Inventors: Yoko Mihara, Kanagawa (JP); Yohei Tatsukami, Kanagawa (JP); Yoshinori Tajima, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 72 days.

(21) Appl. No.: 17/036,054

(22) Filed: Sep. 29, 2020

(65) Prior Publication Data
US 2021/0071210 A1   Mar. 11, 2021

Related U.S. Application Data

(63) Continuation of application No. PCT/JP2019/015013, filed on Apr. 4, 2019.

(30) Foreign Application Priority Data

Apr. 6, 2018 (JP) .............................. JP2018-074191

(51) Int. Cl.
*C12P 7/42* (2006.01)
*C12N 9/88* (2006.01)
*C12P 17/06* (2006.01)

(52) U.S. Cl.
CPC ................. *C12P 7/42* (2013.01); *C12P 17/06* (2013.01)

(58) Field of Classification Search
CPC ........... C12P 17/06; C12P 7/42; C12P 7/8409; C12N 9/88
See application file for complete search history.

(56) References Cited

U.S. PATENT DOCUMENTS

2021/0071210 A1\* 3/2021 Mihara .......... C12Y 402/01053

FOREIGN PATENT DOCUMENTS

KR         20150098497 A     8/2015

OTHER PUBLICATIONS

PCT/JP2019/015013—Written Opinion, (dated 2019).\*
Park, J.-Y., et al., "Production of 13S-hydroxy-9(Z)-octadecenoic acid from linoleic acid by whole recombinant cells expressing linoleate 13-hydratase from Lactobacillus acidophilus," J. Biotechnol. 2015;208:1-10.
Oh, H.-J., et al., "Biotransformation of Linoleic Acid into Hydroxy Fatty Acids and Carboxylic Acids Using a Linoleate Double Bond Hydratase as Key Enzyme," Adv. Synth. Catal. 2015;357:408-416.
Chen, Y. Y., et al., "Characterization of Linoleate 10-Hydratase of Lactobacillus plantarum and Novel Antifungal Metabolites," Front. Microbiol. 2016;7:1561, pp. 1-11.
Kim, K.-R., et al., "Unveiling of Novel Regio-Selective Fatty Acid Double Bond Hydratases From Lactobacillus acidophilus Involved in the Selective Oxyfunctionalization of Mono- and Di-Hydroxy Fatty Acids," Biotechnol. Bioeng. 2015;112(11):2206-2213.
Swizdor, A., et al., "Biotransformations Utilizing Beta-Oxidation Cycle Reactions in the Synthesis of Natural Compounds and Medicines," Int. J. Mol. Sci. 2012;13:16514-16543.
NCBI, "GenBank Accession No. AHW98239, linoleate 13-hydratase [*Lactobacillus acidophilus*]", Apr. 20, 2013, retrieved on Jun. 20, 2019, <URL: https://ww.ncbi.nlm.nih.gov/protein/AHW98239.1?report-genbank&log$=protalign&blast_rank=1&RID=GJYSNXNV014>, Origin.
UniProt, UniProtKB-A0A0R1NM81, "Lactobacillus gallinarum DSM 10532", Last modified: Jan. 20, 2016, [Retrieved on Jun. 20, 2019], <URL:https://www.uniprot.org/uniprot/A0A0R1NM8l>, sequence.
Uniprot, UniProtKB-A0A226 SF70, "Lactobacillus crispatus", Last modified: Oct. 25, 2017, [Retrieved on Jun. 20, 2019], <URL:https://www.uniprot.org/uniprot/A0A226SF70>, sequence.
Uniprot, UniProtKB-A0A1C2D7G5, "Lactobacillus crispatus", Last modified: Nov. 2, 2016, [Retrieved on Jun. 20, 2019], <URL:https://www.uniprot.org/uniprot/A0A1C2D7G5>, sequence.
UniProt, UniProtKB-A0A226 SCJ9, "Lactobacillus crispatus", Last modified: Oct. 25, 2017, [Retrieved on Jun. 20, 2019], <URL:https://www.uniprot.org/uniprot/A0A226SCJ9>, sequence.
UniProt, UniProtKB-A0A0R1YDA1, Lactobacillus hamsteri DSM 5661, Last modified: Jan. 20, 2016, [Retrieved on Jun. 20, 2019], <URL:https://www.uniprot.org/uniprot/A0A0R1YDA1>, sequence.
UniProt, UniProtKB-G8PAJ4, "Pediococcus claussenii", Last modified: Feb. 22, 2012, [Retrieved on Jun. 20, 2019], <URL:https://www.uniprot.org/uniprot/G8PAJ4>, sequence.
UniProt, UniProtKB A0A0R2NJM0, "Pediococcus argentinicus", Last modified: Jan. 20, 2016, [Retrieved on Jun. 20, 2019], <URL:https://www.uniprot.org/uniprot/A0A0R2NJM0>, sequence.
UniProt, UniProtKB-Q8DT14, "*Streptococcus mutans* serotype c", Last modified: Mar. 1, 2003, [Retrieved on Jun. 20, 2019], <URL:https://www.uniprot.org/uniprot/Q8DT14>, sequence.
UniProt, UniProtKB-A0A2J9QD48, "*Streptococcus mutans*", Last modified: Mar. 28, 2018, [Retrieved on Jun. 20, 2019], <URL:https://www.uniprot.org/uniprot/A0A2J9QD48>, sequence.
UniProt, UniProtKB-A0AIH0JQ81, "*Streptococcus equinus*", Last modified: Apr. 12, 2017, [Retrieved on Jun. 20, 2019], <URL:https://www.uniprot.org/uniprot/AOA1H0JQ8l>, sequence.

(Continued)

*Primary Examiner* — Tekchand Saidha
(74) *Attorney, Agent, or Firm* — Cermak Nakajima & McGowan LLP; Shelly Guest Cermak

(57) ABSTRACT

The present invention provides a method of producing 13-hydroxy-9(Z)-octadecenoic acid, productivity of which has been enhanced. Specifically, the present invention provides a method of producing 13-hydroxy-9(Z)-octadecenoic acid, by producing 13-hydroxy-9(Z)-octadecenoic acid from linoleic acid in the presence of a transformed microorganism that produces a protein such as the following: (A) a protein having an amino acid sequence of SEQ ID NOs: 4, 5, 8 to 10, 13, or 14; (B) a protein having an amino acid sequence containing one or several amino acid substitutions, deletions, insertions or additions in the amino acid sequence of SEQ ID NOs: 4, 5, 8 to 10, 13, or 14, and having a linoleate 13-hydratase activity; and (C) a protein having an amino acid sequence having 90% or more identity to the amino acid sequence of SEQ ID NOs: 4, 5, 8 to 10, 13 or 14, and having a linoleate 13-hydratase activity.

20 Claims, 29 Drawing Sheets
Specification includes a Sequence Listing.

(56) References Cited

OTHER PUBLICATIONS

UniProt, UniProtKB-A0A239R7F6, "*Streptococcus equinus*", Last modified: Oct. 25, 2017, [Retrieved on Jun. 20, 2019), <URL:https://www.uniprot.org/uniprot/A0A239R7F6>, sequence.

NCBI, "GenBank Accession No. WP_003546333, oleate hydratase [*Lactobacillus acidophilus*]", Nov. 20, 2015, [Retrieved on Jun. 20, 2019], <URL:https://www.ncbi.nlm.nih.gov/protein/489614893?sat=5&satkey=120419704>, Origin.

Kang, W.-R., et al., "Production of δ-decalactone from linoleic acid via 13-hydroxy-9(Z)-octadecenoic acid intermediate by one-pot reaction using linoleate 13-hydratase and whole Yarrowia lipolytica cells," Biotechnol. Lett. 2016;38:817-823.

International Search Report and Written Opinion for PCT Patent App. No. PCT/JP2019/015013 (dated Jul. 2, 2019) with English translation of the ISR.

UniProt, UniProtKB-A0A249NK64, "Lactobacillus gasseri DSM 14869" Last modified: Dec. 20, 2017, [Retrieved on Jun. 20, 2019), <URL:https://www.uniprot.org/uniprot/A0A249NK64>, sequence.

Wache, Y., et al., "Role of β-Oxidation Enzymes in γ-Decalactone Production by the Yeast Yarrowia lipolytica," Appl. Environmen. Microbiol. 2001;67(12):5700-5704.

Database UniProtKB [Online], Jan. 20, 2016, Database Accession No. A0A0R1NM81, pp. 1-2; retrieved from the internet on Nov. 22, 2019.

Database UniProt [Online], Feb. 28, 2018, Database Accession No. A0A2I1WLH7, p. 1; retrieved from the internet on Nov. 22, 2019.

Database UniProtKB [Online], Jan. 20, 2016, Database Accession No. A0A0R1YDA1, p. 1; retrieved from the internet on Nov. 22, 2019.

Database UniProtKB [Online], Dec. 20, 2017, Database Accession No. A0A249NK64, p. 1; retrieved from the internet on Nov. 22, 2019.

Database UniProtKB [Online], Feb. 22, 2012, Accession No. G8PAJ4, pp. 1-2; retrieved from the internet on Nov. 22, 2019.

Database UniProtKB [Online], Mar. 1, 2013, Accession No. Q8DT14, pp. 1-2; retrieved from the internet on Nov. 22, 2019.

Database UniProtKB [Online], Apr. 12, 2017, Accession No. A0A1H0JQ81, p. 1; retrieved from the internet on Nov. 22, 2019.

Extended European Search Report for European Patent App. No. 19781497.3 (dated Dec. 20, 2021).

* cited by examiner

SEQUENCE LISTING

<160> NUMBER OF SEQ ID NOS: 91

<210> SEQ ID NO 1
<211> LENGTH: 590
<212> TYPE: PRT
<213> ORGANISM: Lactobacillus acidophilus

<400> SEQUENCE: 1

```
Met His Tyr Ser Ser Gly Asn Tyr Glu Ala Phe Val Asn Ala Ser Lys
1               5                   10                  15

Pro Lys Asp Val Asp Gln Lys Ser Ala Tyr Leu Val Gly Ser Gly Leu
            20                  25                  30

Ala Ser Leu Ala Ser Ala Val Phe Leu Ile Arg Asp Gly His Met Lys
        35                  40                  45

Gly Asp Arg Ile His Ile Leu Glu Glu Leu Ser Leu Pro Gly Gly Ser
50                  55                  60

Met Asp Gly Ile Tyr Asn Lys Gln Lys Glu Ser Tyr Ile Ile Arg Gly
65                  70                  75                  80

Gly Arg Glu Met Glu Ala His Phe Glu Cys Leu Trp Asp Leu Phe Arg
                85                  90                  95

Ser Ile Pro Ser Ala Glu Asn Lys Asp Glu Ser Val Leu Asp Glu Phe
            100                 105                 110

Tyr Arg Leu Asn Arg Lys Asp Pro Ser Phe Ala Lys Thr Arg Val Ile
        115                 120                 125

Val Asn Arg Gly His Glu Leu Pro Thr Asp Gly Gln Leu Leu Leu Thr
130                 135                 140

Pro Lys Ala Val Lys Glu Ile Ile Asp Leu Cys Leu Thr Pro Glu Lys
145                 150                 155                 160

Asp Leu Gln Asn Lys Lys Ile Asn Glu Val Phe Ser Lys Glu Phe Phe
                165                 170                 175

Glu Ser Asn Phe Trp Leu Tyr Trp Ser Thr Met Phe Ala Phe Glu Pro
            180                 185                 190

Trp Ala Ser Ala Met Glu Met Arg Arg Tyr Leu Met Arg Phe Val Gln
        195                 200                 205

His Val Ser Thr Leu Lys Asn Leu Ser Ser Leu Arg Phe Thr Lys Tyr
210                 215                 220

Asn Gln Tyr Glu Ser Leu Ile Leu Pro Met Val Lys Tyr Leu Lys Asp
225                 230                 235                 240

Arg Gly Val Gln Phe His Tyr Asn Thr Val Val Asp Asn Ile Phe Val
                245                 250                 255

Asn Arg Ser Asn Gly Glu Lys Ile Ala Lys Gln Ile Leu Leu Thr Glu
            260                 265                 270

Asn Gly Glu Lys Lys Ser Ile Asp Leu Thr Glu Asn Asp Leu Val Phe
        275                 280                 285

Val Thr Asn Gly Ser Ile Thr Glu Ser Thr Thr Tyr Gly Asp Asn Leu
290                 295                 300

His Pro Ala Ser Glu Glu His Lys Leu Gly Ala Thr Trp Lys Leu Trp
305                 310                 315                 320

Gln Asn Leu Ala Ala Gln Asp Asp Phe Gly His Pro Asp Val Phe
                325                 330                 335

Cys Lys Asp Ile Pro Lys Ala Asn Trp Val Met Ser Ala Thr Ile Thr
            340                 345                 350

Phe Lys Asn Asn Asp Ile Val Pro Phe Ile Glu Ala Val Asn Lys Lys
        355                 360                 365

Asp Pro His Ser Gly Ser Ile Val Thr Ser Gly Pro Thr Thr Ile Lys
370                 375                 380

Asp Ser Asn Trp Leu Leu Gly Tyr Ser Ile Ser Arg Gln Pro His Phe
385                 390                 395                 400

Glu Ala Gln Lys Pro Asn Glu Leu Ile Val Trp Leu Tyr Gly Leu Phe
```

```
            405                 410                 415
Ser Asp Thr Lys Gly Asn Tyr Val Glu Lys Thr Met Pro Asp Cys Asn
            420                 425                 430

Gly Ile Glu Leu Cys Glu Glu Trp Leu Tyr His Met Gly Val Pro Glu
            435                 440                 445

Glu Arg Ile Pro Glu Met Ala Ser Ala Thr Thr Ile Pro Ala His
450                 455                 460

Met Pro Tyr Ile Thr Ser Tyr Phe Met Pro Arg Ala Leu Gly Asp Arg
465                 470                 475                 480

Pro Lys Val Val Pro Asp His Ser Lys Asn Leu Ala Phe Ile Gly Asn
            485                 490                 495

Phe Ala Glu Thr Pro Arg Asp Thr Val Phe Thr Thr Glu Tyr Ser Val
            500                 505                 510

Arg Thr Ala Met Glu Ala Val Tyr Thr Leu Leu Asn Ile Asp Arg Gly
            515                 520                 525

Val Pro Glu Val Phe Ala Ser Ala Phe Asp Val Arg Met Leu Met Asn
            530                 535                 540

Ala Met Tyr Tyr Leu Asn Asp Gln Lys Lys Leu Glu Asp Leu Asp Leu
545                 550                 555                 560

Pro Ile Ala Glu Lys Leu Ala Ile Lys Gly Met Leu Lys Lys Val Lys
            565                 570                 575

Gly Thr Tyr Ile Glu Glu Leu Leu Lys Lys Tyr Lys Leu Val
            580                 585                 590

<210> SEQ ID NO 2
<211> LENGTH: 590
<212> TYPE: PRT
<213> ORGANISM: Lactobacillus amylovorus

<400> SEQUENCE: 2

Met His Tyr Ser Asn Gly Asn Tyr Glu Ala Phe Val Asn Ala Ser Lys
1               5                   10                  15

Pro Lys Asp Val Asp Gln Lys Ser Ala Tyr Ile Val Gly Ser Gly Leu
            20                  25                  30

Ala Ala Leu Ala Ser Ala Val Phe Leu Ile Arg Asp Gly His Met Lys
            35                  40                  45

Gly Glu Arg Ile His Ile Phe Glu Glu Leu Gly Leu Pro Gly Gly Ser
50                  55                  60

Met Asp Gly Ile Tyr Asn Lys Gln Lys Glu Ser Tyr Ile Ile Arg Gly
65                  70                  75                  80

Gly Arg Glu Met Glu Pro His Phe Glu Cys Leu Trp Asp Leu Phe Arg
                85                  90                  95

Ser Ile Pro Ser Pro Glu Asn Lys Asp Glu Ser Val Leu Asp Glu Phe
            100                 105                 110

Tyr Arg Leu Asn Arg Arg Asp Pro Ser Tyr Ala Lys Thr Arg Val Ile
            115                 120                 125

Val Asn Arg Gly Glu Ala Leu Pro Thr Asp Gly Gln Leu Leu Leu Thr
            130                 135                 140

Pro Lys Ala Val Lys Glu Ile Val Asp Leu Cys Leu Thr Pro Glu Lys
145                 150                 155                 160

Asp Leu Gln Asn Lys Lys Ile Asn Glu Val Phe Asp Lys Glu Phe Phe
                165                 170                 175

Gln Ser Asn Phe Trp Leu Tyr Trp Ser Thr Met Phe Ala Phe Glu Pro
            180                 185                 190
```

Trp Ala Ser Ala Met Glu Met Arg Arg Tyr Leu Met Arg Phe Val Gln
            195                 200                 205

His Val Ala Thr Leu Lys Asn Leu Ser Ser Leu Arg Phe Thr Lys Tyr
210                 215                 220

Asn Gln Tyr Glu Ser Leu Ile Leu Pro Met Val Lys Tyr Leu Lys Asp
225                 230                 235                 240

His Gly Val Gln Phe His Tyr Asp Thr Val Asp Asn Val Phe Val
            245                 250                 255

Asn Arg Ser Asn Gly Glu Lys Val Ala Lys Gln Ile Ile Leu Thr Glu
            260                 265                 270

Asn Gly Glu Lys Lys Asn Ile Asp Leu Thr Glu Asn Asp Leu Val Phe
            275                 280                 285

Val Thr Asn Gly Ser Ile Thr Glu Ser Thr Thr Tyr Gly Asp Asn Leu
290                 295                 300

His Pro Ala Pro Glu Glu His Glu Leu Gly Ala Ser Trp Gln Leu Trp
305                 310                 315                 320

Lys Asn Leu Ala Ala Gln Asp Glu Asp Phe Gly His Pro Glu Val Phe
                325                 330                 335

Cys Lys Asp Ile Pro Lys Ala Asn Trp Arg Met Ser Ala Thr Ile Thr
                340                 345                 350

Phe Lys Asn Asn Asp Ile Val Pro Phe Ile Glu Ala Val Asn Lys Lys
            355                 360                 365

Asp Pro His Ser Gly Ser Ile Val Thr Ser Gly Pro Thr Thr Ile Lys
            370                 375                 380

Asp Ser Asn Trp Leu Leu Gly Tyr Ser Ile Ser Arg Gln Pro His Phe
385                 390                 395                 400

Lys Ala Gln Lys Pro Asn Glu Leu Ile Val Trp Leu Tyr Gly Leu Phe
            405                 410                 415

Ser Asp Thr Lys Gly Asn Tyr Val Glu Lys Thr Met Pro Asp Cys Asn
            420                 425                 430

Gly Ile Glu Leu Cys Glu Glu Trp Leu Tyr His Met Gly Val Pro Glu
            435                 440                 445

Glu Arg Ile Pro Glu Met Ala Ala Ala Thr Thr Ile Pro Ala His
450                 455                 460

Met Pro Tyr Ile Thr Ser Tyr Phe Met Pro Arg Ala Leu Gly Asp Arg
465                 470                 475                 480

Pro Lys Val Val Pro Asp His Ser Lys Asn Leu Ala Phe Ile Gly Asn
                485                 490                 495

Phe Ala Glu Thr Pro Arg Asp Thr Val Phe Thr Thr Glu Tyr Ser Val
            500                 505                 510

Arg Thr Ala Met Glu Ala Val Tyr Thr Leu Leu Asp Ile Asp Arg Gly
            515                 520                 525

Val Pro Glu Val Phe Ala Ser Ala Phe Asp Val Arg Met Leu Met Asn
530                 535                 540

Ala Met Tyr Tyr Leu Asn Asp Gln Lys Lys Leu Glu Glu Leu Asp Leu
545                 550                 555                 560

Pro Ile Pro Glu Lys Met Ala Ile Lys Gly Met Leu Lys Lys Val Lys
                565                 570                 575

Gly Thr Tyr Val Glu Glu Leu Leu Lys Lys Tyr Lys Leu Ile
            580                 585                 590

<210> SEQ ID NO 3
<211> LENGTH: 590
<212> TYPE: PRT

<213> ORGANISM: Lactobacillus helveticus

<400> SEQUENCE: 3

```
Met His Tyr Ser Asn Gly Asn Tyr Glu Ala Phe Val Lys Ala Glu Lys
1               5                   10                  15

Pro Lys Asp Val Asp Gln Lys Ser Ala Tyr Ile Val Gly Ser Gly Leu
            20                  25                  30

Ala Ala Leu Ala Ser Ala Val Phe Leu Ile Arg Asp Gly Gln Met Lys
        35                  40                  45

Gly Asn Arg Ile His Ile Phe Glu Glu Leu Ser Leu Pro Gly Gly Ser
    50                  55                  60

Met Asp Gly Ile Tyr Ser Lys Glu Lys Glu Ser Tyr Ile Ile Arg Gly
65                  70                  75                  80

Gly Arg Glu Met Glu Pro His Phe Glu Cys Leu Trp Asp Leu Phe Arg
                85                  90                  95

Ser Ile Pro Ser Thr Glu His Glu Gly Glu Ser Ile Leu Asp Glu Phe
            100                 105                 110

Tyr Arg Leu Asn Arg Lys Asp Pro Ser Tyr Ala Lys Thr Arg Val Ile
        115                 120                 125

Ile Asn Arg Gly Glu Ala Leu Pro Thr Asp Gly Gln Leu Leu Leu Thr
    130                 135                 140

Pro Lys Ala Val Lys Glu Ile Val Asp Leu Cys Leu Thr Pro Glu Lys
145                 150                 155                 160

Asp Leu Gln Asn Lys Lys Ile Asn Glu Val Phe Thr Lys Glu Phe Phe
                165                 170                 175

Gln Ser Asn Phe Trp Leu Tyr Trp Ser Thr Met Phe Ala Phe Glu Pro
            180                 185                 190

Trp Ala Ser Ala Met Glu Met Arg Arg Tyr Leu Met Arg Phe Val Gln
        195                 200                 205

His Val Ala Thr Leu Lys Asn Leu Ser Ser Leu Arg Phe Thr Lys Tyr
    210                 215                 220

Asn Gln Tyr Glu Ser Leu Ile Leu Pro Met Val Lys Tyr Leu Lys Ser
225                 230                 235                 240

His Gly Val Gln Phe His Tyr Asp Thr Val Val Asp Asn Ile Phe Val
                245                 250                 255

Asn Arg Ser Asn Gly Glu Lys Val Ala Lys Gln Ile Ile Leu Thr Glu
            260                 265                 270

Lys Gly Glu Arg Lys Thr Ile Asp Leu Thr Glu Asn Asp Leu Val Phe
        275                 280                 285

Val Thr Asn Gly Ser Ile Thr Glu Ser Thr Thr Tyr Gly Asp Asn Phe
    290                 295                 300

His Pro Ala Ser Glu Glu His Glu Leu Gly Ala Ser Trp Gln Leu Trp
305                 310                 315                 320

Lys Asn Leu Ala Ala Gln Asp Ser Asp Phe Gly His Pro Asp Val Phe
                325                 330                 335

Cys Lys Asp Ile Pro Lys Ala Asn Trp Arg Met Ser Ala Thr Ile Thr
            340                 345                 350

Phe Lys Asn Asp Asp Ile Val Pro Phe Ile Glu Ala Val Asn Lys Lys
        355                 360                 365

Asp Pro His Ser Gly Ser Ile Val Thr Ser Gly Pro Thr Thr Ile Lys
    370                 375                 380

Asp Ser Asn Trp Leu Leu Gly Tyr Ser Ile Ser Arg Gln Pro His Phe
385                 390                 395                 400
```

```
Lys Ala Gln Lys Pro Asn Glu Leu Ile Val Trp Leu Tyr Gly Leu Phe
                405                 410                 415

Ser Asp Thr Lys Gly Asn Tyr Val Glu Lys Thr Met Pro Asp Cys Asn
            420                 425                 430

Gly Ile Glu Leu Cys Glu Glu Trp Leu Tyr His Met Gly Val Pro Glu
        435                 440                 445

Glu Arg Ile Pro Glu Met Ala Ala Ala Thr Thr Ile Pro Ala His
    450                 455                 460

Met Pro Tyr Ile Thr Ser Tyr Phe Met Pro Arg Ala Leu Gly Asp Arg
465                 470                 475                 480

Pro Lys Val Val Pro Asp His Ser Lys Asn Leu Ala Phe Ile Gly Asn
                485                 490                 495

Phe Ala Glu Thr Pro Arg Asp Thr Val Phe Thr Thr Glu Tyr Ser Val
            500                 505                 510

Arg Thr Ala Met Glu Ala Val Tyr Thr Leu Leu Asp Ile Asp Arg Gly
        515                 520                 525

Val Pro Glu Val Phe Ala Ser Ala Phe Asp Val Arg Met Leu Met Asn
    530                 535                 540

Ala Leu Tyr Tyr Leu Asn Asp Gln Lys Lys Leu Glu Asp Leu Asp Leu
545                 550                 555                 560

Pro Met Gly Glu Lys Leu Ala Ile Lys Gly Met Leu Lys Val Lys
                565                 570                 575

Gly Thr Tyr Ile Glu Glu Leu Met Lys Glu Tyr Lys Leu Ile
            580                 585                 590

<210> SEQ ID NO 4
<211> LENGTH: 590
<212> TYPE: PRT
<213> ORGANISM: Lactobacillus gallinarum

<400> SEQUENCE: 4

Met His Tyr Ser Asn Gly Asn Tyr Glu Ala Phe Val Lys Ala Glu Lys
1               5                   10                  15

Pro Lys Asp Val Asp Gln Lys Ser Ala Tyr Ile Val Gly Ser Gly Leu
                20                  25                  30

Ala Ala Leu Ala Ser Ala Val Phe Leu Ile Arg Asp Gly Gln Met Lys
            35                  40                  45

Gly Asn Arg Ile His Ile Phe Glu Glu Leu Ala Leu Pro Gly Gly Ser
        50                  55                  60

Met Asp Gly Ile Tyr Asn Lys Glu Lys Glu Ser Tyr Ile Ile Arg Gly
65                  70                  75                  80

Gly Arg Glu Met Glu Pro His Phe Glu Cys Leu Trp Asp Leu Phe Arg
                85                  90                  95

Ser Ile Pro Ser Thr Glu His Glu Gly Glu Ser Ile Leu Asp Glu Phe
            100                 105                 110

Tyr Arg Leu Asn Arg Lys Asp Pro Ser Tyr Ala Lys Thr Arg Val Ile
        115                 120                 125

Ile Asn Arg Gly Glu Ala Leu Pro Thr Asp Gly Gln Leu Leu Leu Thr
    130                 135                 140

Pro Lys Ala Val Lys Glu Ile Ile Asp Leu Cys Leu Thr Pro Glu Lys
145                 150                 155                 160

Asp Leu Gln Asn Lys Lys Ile Asn Glu Val Phe Thr Lys Glu Phe Phe
                165                 170                 175

Gln Ser Asn Phe Trp Leu Tyr Trp Ser Thr Met Phe Ala Phe Glu Pro
            180                 185                 190
```

Trp Ala Ser Ala Met Glu Met Arg Arg Tyr Leu Met Arg Phe Val Gln
            195                 200                 205

His Val Ala Thr Leu Lys Asn Leu Ser Ser Leu Arg Phe Thr Lys Tyr
    210                 215                 220

Asn Gln Tyr Glu Ser Leu Ile Leu Pro Met Val Lys Tyr Leu Lys Gly
225                 230                 235                 240

His Gly Val Gln Phe His Tyr Asp Thr Val Asp Asn Ile Phe Val
                245                 250                 255

Asn Arg Ser Asp Gly Lys Lys Val Ala Lys Gln Ile Val Leu Thr Glu
            260                 265                 270

Lys Gly Glu Arg Lys Thr Ile Asp Leu Thr Glu Asn Asp Leu Val Phe
            275                 280                 285

Val Thr Asn Gly Ser Ile Thr Glu Ser Thr Thr Tyr Gly Asp Asn Phe
    290                 295                 300

His Pro Ala Pro Ala Glu His Glu Leu Gly Ala Ser Trp Gln Leu Trp
305                 310                 315                 320

Lys Asn Leu Ala Ala Gln Asp Glu Asp Phe Gly His Pro Glu Val Phe
                325                 330                 335

Cys Arg Asp Ile Pro Lys Ala Asn Trp Arg Met Ser Ala Thr Ile Thr
            340                 345                 350

Phe Lys Asn Asp Asp Ile Val Pro Phe Ile Glu Ala Val Asn Lys Lys
            355                 360                 365

Asp Pro His Ser Gly Ser Ile Val Thr Ser Gly Pro Thr Thr Ile Lys
            370                 375                 380

Asp Ser Asn Trp Leu Leu Gly Tyr Ser Ile Ser Arg Gln Pro His Phe
385                 390                 395                 400

Lys Ala Gln Lys Pro Asn Glu Leu Ile Val Trp Leu Tyr Gly Leu Phe
                405                 410                 415

Ser Asp Thr Lys Gly Asn Tyr Val Glu Lys Thr Met Pro Asp Cys Asn
                420                 425                 430

Gly Ile Glu Leu Cys Glu Glu Trp Leu Tyr His Met Gly Val Pro Glu
            435                 440                 445

Glu Arg Ile Pro Glu Met Ala Ala Ala Thr Thr Ile Pro Ala His
            450                 455                 460

Met Pro Tyr Ile Thr Ser Tyr Phe Met Pro Arg Ala Leu Gly Asp Arg
465                 470                 475                 480

Pro Lys Val Val Pro Asp His Ser Lys Asn Leu Ala Phe Ile Gly Asn
                485                 490                 495

Phe Ala Glu Thr Pro Arg Asp Thr Val Phe Thr Thr Glu Tyr Ser Val
                500                 505                 510

Arg Thr Ala Met Glu Ala Val Tyr Thr Leu Leu Asp Ile Asp Arg Gly
            515                 520                 525

Val Pro Glu Val Phe Ala Ser Ala Phe Asp Val Arg Met Leu Met Asn
            530                 535                 540

Ala Met Tyr Tyr Leu Asn Asp Gln Lys Lys Leu Glu Asp Phe Asp Leu
545                 550                 555                 560

Pro Met Pro Glu Lys Leu Val Ile Lys Gly Ile Leu Lys Lys Val Lys
                565                 570                 575

Gly Thr Tyr Val Glu Glu Leu Met Lys Lys Tyr Lys Leu Ile
            580                 585                 590

<210> SEQ ID NO 5
<211> LENGTH: 590

<212> TYPE: PRT
<213> ORGANISM: Lactobacillus crispatus

<400> SEQUENCE: 5

```
Met His Tyr Ser Asn Gly Asn Tyr Glu Ala Phe Val Lys Ala Asp Lys
1               5                   10                  15

Pro Lys Asp Val Asp Gln Lys Ser Ala Tyr Ile Val Gly Ser Gly Leu
            20                  25                  30

Ala Ala Leu Ala Thr Ala Val Phe Leu Ile Arg Asp Gly Gln Met Lys
        35                  40                  45

Gly Glu Lys Ile His Ile Phe Glu Glu Leu Gly Leu Pro Gly Gly Ser
    50                  55                  60

Met Asp Gly Ile Tyr Asn Lys Glu Lys Glu Ser Tyr Ile Ile Arg Gly
65                  70                  75                  80

Gly Arg Glu Met Glu Pro His Phe Glu Cys Leu Trp Asp Leu Phe Arg
                85                  90                  95

Ser Ile Pro Ser Pro Asp His Glu Gly Glu Ser Ile Leu Asp Ser Phe
            100                 105                 110

Tyr Arg Leu Asn Arg Lys Asp Pro Ser Tyr Ala Lys Thr Arg Val Ile
        115                 120                 125

Val Asn Arg Gly Gln Ala Leu Pro Thr Asp Gly Gln Leu Leu Leu Thr
130                 135                 140

Pro Lys Ala Val Lys Glu Ile Val Asp Leu Cys Leu Thr Pro Glu Lys
145                 150                 155                 160

Asp Leu Gln Asn Lys Lys Ile Asn Glu Val Phe Thr Lys Glu Phe Phe
                165                 170                 175

Glu Ser Asn Phe Trp Leu Tyr Trp Ser Thr Met Phe Ala Phe Glu Pro
            180                 185                 190

Trp Ala Ser Ala Met Glu Met Arg Arg Tyr Leu Met Arg Phe Val Gln
        195                 200                 205

His Val Ala Thr Leu Lys Asn Leu Ser Ser Leu Arg Phe Thr Lys Tyr
    210                 215                 220

Asn Gln Tyr Glu Ser Leu Ile Leu Pro Leu Val Lys Tyr Leu Lys Asp
225                 230                 235                 240

Arg Gly Val Ile Phe His Tyr Asn Thr Val Val Asp Asn Ile Phe Val
                245                 250                 255

Asn Arg Ser Asp Gly Glu Lys Val Ala Lys Gln Ile Ile Leu Thr Glu
            260                 265                 270

Asp Gly Glu Lys Lys Thr Ile Asp Leu Thr Pro Asn Asp Leu Val Phe
        275                 280                 285

Val Thr Asn Gly Ser Ile Thr Glu Ser Thr Thr Tyr Gly Asp Gln Leu
    290                 295                 300

His Pro Ala Pro Ala Glu His Glu Leu Gly Ala Ser Trp Gln Leu Trp
305                 310                 315                 320

Lys Asn Leu Ala Ala Gln Asp Glu Asp Phe Gly His Pro Asp Val Phe
                325                 330                 335

Cys Lys Asp Ile Pro Lys Ala Asn Trp Arg Met Ser Ala Thr Ile Thr
            340                 345                 350

Phe Lys Asn Asp Asp Val Val Pro Phe Ile Glu Ala Val Asn Lys Lys
        355                 360                 365

Asp Pro His Ser Gly Ser Ile Val Thr Ser Gly Pro Thr Thr Ile Lys
    370                 375                 380

Asp Ser Asn Trp Leu Leu Gly Tyr Ser Ile Ser Arg Gln Pro His Phe
385                 390                 395                 400
```

```
Lys Ala Gln Lys Pro Asn Glu Leu Ile Val Trp Leu Tyr Gly Leu Phe
                405                 410                 415
Ser Asp Thr Lys Gly Asn Tyr Val Glu Lys Thr Met Pro Asp Cys Asn
            420                 425                 430
Gly Leu Glu Met Cys Glu Glu Trp Leu Tyr His Met Gly Val Pro Glu
        435                 440                 445
Glu Arg Ile Pro Glu Ile Ala Ala Ala Thr Thr Ile Pro Val His
    450                 455                 460
Met Pro Tyr Ile Thr Ser Tyr Phe Met Pro Arg Ala Leu Gly Asp Arg
465                 470                 475                 480
Pro Lys Val Val Pro Glu His Ser Lys Asn Leu Ala Phe Ile Gly Asn
                485                 490                 495
Phe Ala Glu Thr Pro Arg Asp Thr Val Phe Thr Thr Glu Tyr Ser Val
            500                 505                 510
Arg Thr Ala Met Glu Ala Val Tyr Thr Leu Leu Asp Ile Asp Arg Gly
        515                 520                 525
Val Pro Glu Val Phe Ala Ser Ala Phe Asp Val Arg Met Leu Met Asn
    530                 535                 540
Ala Met Tyr Tyr Leu Asn Asp Gln Lys Lys Leu Val Asp Leu Asp Leu
545                 550                 555                 560
Pro Met Pro Glu Lys Leu Ala Ile Lys Gly Met Leu Lys Lys Val Lys
                565                 570                 575
Gly Thr Tyr Ile Glu Glu Leu Met Lys Lys Tyr Lys Leu Ile
            580                 585                 590

<210> SEQ ID NO 6
<211> LENGTH: 590
<212> TYPE: PRT
<213> ORGANISM: Lactobacillus kefiranofaciens

<400> SEQUENCE: 6

Met His Tyr Ser Asn Gly Asn Tyr Glu Ala Phe Val Lys Ala Glu Lys
1               5                   10                  15
Pro Lys Asp Val Asp Gln Lys Ser Ala Tyr Ile Val Gly Ser Gly Leu
            20                  25                  30
Ala Ala Leu Ala Ser Ala Val Phe Leu Ile Arg Asp Gly Gln Met Lys
        35                  40                  45
Gly Glu His Ile His Ile Leu Glu Glu Leu Gly Leu Pro Gly Gly Ser
    50                  55                  60
Met Asp Gly Ile Tyr Asn Lys Glu Lys Glu Ser Tyr Ile Ile Arg Gly
65                  70                  75                  80
Gly Arg Glu Met Glu Pro His Phe Glu Cys Leu Trp Asp Leu Phe Arg
                85                  90                  95
Ser Ile Pro Ser Thr Glu His Glu Gly Glu Ser Ile Leu Asp Glu Phe
            100                 105                 110
Tyr Arg Leu Asn Arg Arg Asp Pro Ser Tyr Ala Lys Thr Arg Val Ile
        115                 120                 125
Val Asn Arg Gly Gln Ala Leu Pro Thr Asp Gly Gln Leu Leu Leu Thr
    130                 135                 140
Pro Lys Ala Val Lys Glu Ile Val Asp Leu Cys Leu Thr Pro Glu Lys
145                 150                 155                 160
Asp Leu Gln Asn Lys Lys Ile Asn Glu Val Phe Thr Lys Glu Phe Phe
                165                 170                 175
Glu Ser Asn Phe Trp Leu Tyr Trp Ser Thr Met Phe Ala Phe Glu Pro
```

```
            180                 185                 190
Trp Ala Ser Ala Met Glu Met Arg Arg Tyr Leu Met Arg Phe Val Gln
            195                 200                 205

His Val Ala Thr Leu Lys Asn Leu Ser Ser Leu Arg Phe Thr Lys Tyr
            210                 215                 220

Asn Gln Tyr Glu Ser Leu Ile Leu Pro Met Val Lys Tyr Leu Lys Asp
225                 230                 235                 240

His Gly Val Gln Phe His Tyr Asn Thr Ile Val Asp Asn Val Phe Val
            245                 250                 255

Asn Arg Ser Asn Gly Glu Lys Val Ala Lys Gln Ile Ile Leu Thr Glu
            260                 265                 270

Asn Gly Glu Lys Lys Ser Ile Asp Leu Thr Pro Asn Asp Leu Val Phe
            275                 280                 285

Val Thr Asn Gly Ser Ile Thr Glu Ser Thr Thr Tyr Gly Asp Asn Thr
            290                 295                 300

His Pro Ala Pro Ala Glu Tyr Glu Leu Gly Ala Ser Trp Gln Leu Trp
305                 310                 315                 320

Lys Asn Leu Ala Ala Gln Asp Glu Asp Phe Gly His Pro Glu Val Phe
                    325                 330                 335

Cys His Asp Ile Pro Lys Ala Asn Trp Arg Met Ser Ala Thr Ile Thr
                    340                 345                 350

Phe Lys Asn Asp Asp Ile Val Pro Phe Ile Glu Ala Val Asn Lys Lys
                355                 360                 365

Asp Pro His Ser Gly Ser Ile Val Thr Ser Gly Pro Thr Thr Ile Lys
        370                 375                 380

Asp Ser Asn Trp Leu Leu Gly Tyr Ser Ile Ser Arg Gln Pro His Phe
385                 390                 395                 400

Lys Ala Gln Lys Pro Asn Glu Leu Ile Val Trp Leu Tyr Gly Leu Phe
                    405                 410                 415

Ser Asp Thr Lys Gly Asn Tyr Ile Gln Lys Thr Met Pro Asp Cys Ser
                420                 425                 430

Gly Met Glu Met Cys Glu Glu Trp Leu Tyr His Met Gly Val Pro Glu
            435                 440                 445

Gly Lys Ile Pro Glu Met Ala Ala Ala Ala Thr Thr Ile Pro Ala His
        450                 455                 460

Met Pro Tyr Ile Thr Ser Tyr Phe Met Pro Arg Ala Leu Gly Asp Arg
465                 470                 475                 480

Pro Lys Val Val Pro Asp His Ser Lys Asn Leu Ala Phe Ile Gly Asn
                    485                 490                 495

Phe Ala Glu Thr Pro Arg Asp Thr Val Phe Thr Thr Glu Tyr Ser Val
                500                 505                 510

Arg Thr Ala Met Glu Ala Val Tyr Thr Leu Leu Asp Ile Asp Arg Gly
            515                 520                 525

Val Pro Glu Val Phe Ala Ser Ala Phe Asp Val Arg Met Leu Met Asn
        530                 535                 540

Ala Met Tyr Tyr Leu Asn Asp Gln Lys Lys Leu Glu Asp Leu Asp Val
545                 550                 555                 560

Ser Met Pro Glu Lys Leu Ala Ile Lys Gly Ile Leu Lys Lys Val Lys
                    565                 570                 575

Gly Thr Tyr Ile Glu Glu Leu Met Lys Lys Tyr Lys Leu Ile
            580                 585                 590

<210> SEQ ID NO 7
```

<211> LENGTH: 600
<212> TYPE: PRT
<213> ORGANISM: Lactobacillus intestinalis

<400> SEQUENCE: 7

```
Met Leu Gly Leu Thr Lys Glu Val Phe Asp Met His Tyr Thr Asn Gly
1               5                   10                  15

Asn Tyr Glu Ala Phe Val Gln Ala Glu Lys Pro Lys Asp Val Glu Asn
            20                  25                  30

Lys Ser Ala Tyr Ile Val Gly Gly Leu Ala Ser Leu Ala Thr Ala
        35                  40                  45

Val Phe Leu Ile Arg Asp Ala Gln Met Pro Gly Asp Lys Ile His Ile
    50                  55                  60

Phe Glu Glu Leu Ala Leu Pro Gly Gly Ser Met Asp Gly Ile Tyr Asn
65                  70                  75                  80

Pro Glu Lys Gln Ala Tyr Ile Ile Arg Gly Gly Arg Glu Met Glu Ser
                85                  90                  95

His Phe Glu Thr Leu Trp Asp Leu Phe Arg Ser Ile Pro Ser Leu Glu
            100                 105                 110

Asn Lys Asp Ile Ser Val Leu Asp Glu Phe Tyr Arg Leu Asn Arg Lys
        115                 120                 125

Asp Pro Ser Tyr Ser Lys Thr Arg Val Ile Val Asn Arg Gly Glu Glu
    130                 135                 140

Leu Pro Thr Asp Gly Lys Leu Leu Leu Thr Pro Lys Ala Ile Lys Glu
145                 150                 155                 160

Ile Val Asp Leu Val Leu Thr Pro Glu Lys Asp Leu Gln Asn Lys Lys
                165                 170                 175

Ile Asn Glu Val Phe Ser Lys Glu Phe Phe Glu Ser Asn Phe Trp Leu
            180                 185                 190

Tyr Trp Ser Thr Met Phe Ala Phe Glu Pro Trp Ala Ser Ala Met Glu
        195                 200                 205

Met Arg Arg Tyr Leu Met Arg Phe Val Gln His Val Ala Thr Leu Lys
    210                 215                 220

Asn Leu Ser Ser Leu Lys Phe Thr Lys Tyr Asn Gln Tyr Glu Ser Leu
225                 230                 235                 240

Ile Leu Pro Leu Val Ser Tyr Leu Lys Asp His Gly Val Gln Phe His
                245                 250                 255

Tyr Asp Thr Val Val Asp Asn Ile Ile Val Asn Arg Ser Glu Gly Lys
            260                 265                 270

Lys Val Ala Thr Glu Ile Lys Leu Thr Glu Asn Gly Lys Glu Lys Thr
        275                 280                 285

Ile His Leu Ser Glu Asp Asp Leu Val Phe Val Thr Asn Gly Ser Ile
    290                 295                 300

Thr Glu Ser Thr Thr Tyr Gly Asp Asn Leu His Pro Ala Ser Gln Glu
305                 310                 315                 320

His Lys Leu Gly Ala Ser Trp Gln Leu Trp Lys Asn Leu Ala Ala Gln
                325                 330                 335

Asp Ser Asp Phe Gly His Pro Glu Lys Phe Tyr Asp Asn Ile Pro Lys
            340                 345                 350

Ala Asn Trp Val Met Ser Ala Thr Ile Thr Phe Lys Asn Asn Asp Ile
        355                 360                 365

Val Pro Phe Ile Glu Lys Val Asn Lys Asp Pro His Ser Gly Ser
    370                 375                 380

Ile Val Ser Ser Gly Pro Thr Thr Ile Lys Asp Ser Asn Trp Leu Leu
```

```
385                 390                 395                 400
Gly Tyr Ser Ile Ser Arg Gln Pro His Phe Arg Lys Gln Lys Pro Asn
                405                 410                 415

Glu Leu Ile Val Trp Leu Tyr Gly Leu Tyr Ser Asp Thr Lys Gly Asn
            420                 425                 430

Tyr Val Gln Lys Thr Met Pro Glu Cys Asn Gly Ile Glu Leu Cys Glu
        435                 440                 445

Glu Trp Leu Tyr His Met Gly Val Pro Glu Lys Ile Ala Glu Met
    450                 455                 460

Ala His Ala Ala Thr Thr Ile Pro Gln His Met Pro Tyr Ile Thr Ser
465                 470                 475                 480

Tyr Phe Met Pro Arg Ala Leu Gly Asp Arg Pro Lys Val Val Pro Asp
                485                 490                 495

Asn Ser Lys Asn Leu Ala Phe Ile Gly Asn Phe Ala Glu Thr Pro Arg
            500                 505                 510

Asp Thr Val Phe Thr Thr Glu Tyr Ser Val Arg Thr Ala Met Glu Ala
        515                 520                 525

Val Tyr Thr Leu Leu Asp Ile Asp Arg Gly Val Pro Glu Val Phe Ala
    530                 535                 540

Ser Ala Phe Asp Val Arg Met Leu Leu Asn Ala Met Tyr Tyr Leu Asn
545                 550                 555                 560

Asp Gln Lys Lys Leu Thr Asp Leu Asp Leu Pro Leu Thr Glu Lys Leu
                565                 570                 575

Ala Ile Lys Gly Met Leu Lys Lys Val Lys Gly Thr Tyr Ile Glu Glu
            580                 585                 590

Leu Leu Lys Gln Tyr Lys Leu Met
        595                 600

<210> SEQ ID NO 8
<211> LENGTH: 590
<212> TYPE: PRT
<213> ORGANISM: Lactobacillus hamsteri

<400> SEQUENCE: 8

Met His Tyr Ser Asn Gly Asn Tyr Glu Ala Phe Val His Ala Ser Lys
1               5                   10                  15

Pro Lys Asp Val Asp Lys Lys Ser Ala Tyr Ile Val Gly Ser Gly Leu
            20                  25                  30

Ala Ser Leu Ala Thr Ala Thr Phe Leu Leu Arg Asp Ala Gln Met Lys
        35                  40                  45

Gly Glu Lys Ile His Ile Leu Glu Glu Leu Ser Leu Pro Gly Gly Ser
    50                  55                  60

Met Asp Gly Ile Tyr Asp Gln Val Lys Gln Ser Tyr Ile Ile Arg Gly
65                  70                  75                  80

Gly Arg Glu Met Glu Thr His Phe Glu Thr Leu Trp Asp Leu Phe Arg
                85                  90                  95

Ser Ile Pro Ser Leu Asp Asn Pro Gly Glu Thr Val Leu Asp Glu Phe
            100                 105                 110

Tyr Arg Leu Asn Arg Lys Asp Pro Ser Phe Ser Lys Thr Arg Val Ile
        115                 120                 125

Val Asn Arg Gly Glu Glu Leu Pro Thr Asp Gly Gln Leu Leu Leu Thr
    130                 135                 140

Pro Lys Ala Val Lys Glu Ile Val Asn Leu Cys Leu Thr Pro Glu Arg
145                 150                 155                 160
```

```
Asp Leu Gln Asp Lys Lys Ile Asn Glu Val Phe Ser Arg Glu Phe Phe
            165                 170                 175
Glu Ser Asn Phe Trp Leu Tyr Trp Ala Thr Met Phe Ala Phe Glu Pro
        180                 185                 190
Trp Ala Ser Ala Met Glu Met Arg Arg Tyr Leu Met Arg Phe Val Gln
    195                 200                 205
His Val Ala Thr Leu Lys Asp Leu Ser Ser Leu Arg Phe Thr Lys Tyr
210                 215                 220
Asn Gln Tyr Glu Ser Leu Ile Leu Pro Met Val Lys Phe Leu Lys Asp
225                 230                 235                 240
His Gly Val Gln Phe His Tyr Asp Thr Val Val Asn Asn Ile Ile Val
            245                 250                 255
Asn Arg Ser Asn Gly Ala Lys Val Ala Glu Glu Ile Lys Met Thr Glu
        260                 265                 270
Asn Gly Glu Glu Lys Ser Ile Lys Leu Ser Pro Asp Asp Leu Val Phe
    275                 280                 285
Val Thr Asn Gly Ser Ile Thr Glu Ser Thr Thr Tyr Gly Asp Asn Leu
290                 295                 300
His Pro Ala Asp Glu His His Glu Phe Gly Ala Ser Trp Gln Leu Trp
305                 310                 315                 320
Lys Asn Leu Ala Ala Gln Asp Ser Asp Phe Gly His Pro Glu Lys Phe
            325                 330                 335
Cys Glu Asn Ile Pro Lys Ala Asn Trp Val Met Ser Ala Thr Val Thr
        340                 345                 350
Phe Lys Asn Asp Asp Ile Val Pro Phe Ile Glu Lys Ile Asn Lys Lys
    355                 360                 365
Asp Pro His Ser Gly Ser Ile Val Thr Ser Gly Pro Thr Thr Ile Lys
370                 375                 380
Asp Ser Asn Trp Met Leu Gly Tyr Ser Ile Ser Arg Gln Pro His Phe
385                 390                 395                 400
His Lys Gln Lys Pro Asn Glu Leu Ile Val Trp Leu Tyr Gly Leu Tyr
            405                 410                 415
Ser Asp Thr Asn Gly Asn Tyr Val Lys Lys Thr Met Pro Glu Cys Asn
        420                 425                 430
Gly Ile Glu Leu Cys Glu Glu Trp Leu Tyr His Met Gly Val Pro Asp
    435                 440                 445
Glu Lys Ile Ser Glu Met Ala His Ala Ala Val Thr Ile Pro Ala His
450                 455                 460
Met Pro Tyr Ile Thr Ser Tyr Phe Met Pro Arg Ala Leu Gly Asp Arg
465                 470                 475                 480
Pro Lys Val Val Pro Glu Lys Ser Lys Asn Leu Ala Phe Ile Gly Asn
            485                 490                 495
Phe Ala Glu Thr Glu Arg Asp Thr Val Phe Thr Thr Glu Tyr Ser Val
        500                 505                 510
Arg Thr Ala Met Glu Ala Val Tyr Thr Leu Leu Asp Ile Asp Arg Gly
    515                 520                 525
Ile Pro Glu Val Phe Ala Ser Ala Phe Asp Val Arg Met Leu Met Asn
530                 535                 540
Ala Met Tyr Tyr Leu Asn Asp Gln Lys Lys Leu Thr Glu Leu Asp Leu
545                 550                 555                 560
Pro Leu Pro Glu Lys Leu Ala Ile Lys Gly Met Leu Lys Lys Val Lys
            565                 570                 575
Gly Thr Tyr Ile Glu Asp Leu Leu Lys Glu Tyr Arg Leu Met
```

-continued

```
                580             585             590

<210> SEQ ID NO 9
<211> LENGTH: 590
<212> TYPE: PRT
<213> ORGANISM: Lactobacillus gasseri

<400> SEQUENCE: 9

Met His Tyr Ser Asn Gly Asn Tyr Glu Ala Phe Ile Asn Ala Glu Lys
1               5                   10                  15

Pro Lys Asp Val Asp Asn Lys Ser Ala Tyr Ile Val Gly Ser Gly Leu
            20                  25                  30

Ala Ala Leu Ala Ala Ala Val Phe Leu Ile Arg Asp Gly His Met Lys
        35                  40                  45

Gly Asp Lys Ile His Val Leu Glu Glu Leu Ala Leu Pro Gly Gly Ser
    50                  55                  60

Met Asp Ala Ile Tyr Asn Val Ala Asp Gln Ala Tyr Val Met Arg Gly
65                  70                  75                  80

Gly Arg Glu Met Glu Pro His Phe Glu Thr Leu Trp Asp Leu Phe Arg
                85                  90                  95

Ser Ile Pro Ser Leu Asp Tyr Pro Asp Gln Ser Val Leu Asp Glu Phe
            100                 105                 110

Tyr Arg Glu Asn Arg Lys Asp Pro Cys Tyr Ser Lys Thr Arg Val Ile
        115                 120                 125

Glu Asn Arg Gly Gln Glu Leu Pro Thr Asp Gly Asp Leu Leu Leu Ser
    130                 135                 140

Pro Lys Ala Val Lys Glu Ile Leu Asn Leu Val Met Thr Pro Glu Lys
145                 150                 155                 160

Asp Leu Gln Asp Lys Lys Ile Asn Glu Val Phe Asp Asp Glu Phe Phe
                165                 170                 175

Lys Ser Asn Phe Trp Leu Tyr Trp Gln Thr Met Phe Ala Phe Met Pro
            180                 185                 190

Trp Ala Ser Ala Met Glu Met Arg Arg Tyr Leu Met Arg Phe Val Gln
        195                 200                 205

His Val Ala Thr Leu Lys Asn Leu Ser Ser Leu Arg Phe Thr Lys Tyr
    210                 215                 220

Asn Gln Tyr Glu Asp Leu Ile Met Pro Leu Ile Ser Tyr Leu Lys Lys
225                 230                 235                 240

His Gly Val Lys Phe His Tyr Asp Thr Ile Val Asp Asn Ile Ile Val
                245                 250                 255

Asn Arg Thr Glu Asp Glu Lys Val Ala Thr Glu Ile Lys Met Thr Glu
            260                 265                 270

Lys Gly Glu Pro Lys Val Ile Lys Leu Thr Pro Asn Asp Leu Val Phe
        275                 280                 285

Val Thr Asn Gly Ser Ile Thr Glu Ser Thr Thr Tyr Gly Asp Asn Thr
    290                 295                 300

His Pro Ala Glu Gln Lys His Glu Leu Gly Pro Ser Trp Gln Leu Trp
305                 310                 315                 320

Lys Asn Leu Ala Ala Gln Asp Glu Asp Phe Gly His Pro Glu Lys Phe
                325                 330                 335

Cys Glu Asn Ile Pro Ala Ala Asn Trp Val Ile Ser Ala Thr Val Thr
            340                 345                 350

Phe Thr Asn Asp Asp Ile Val Pro Tyr Ile Glu Lys Val Asn Lys Lys
        355                 360                 365
```

```
Asp Pro His Ser Gly Ser Ile Val Thr Ser Gly Pro Thr Thr Ile Lys
    370                 375                 380

Asp Ser Asn Trp Leu Leu Gly Tyr Ser Ile Ser Arg Gln Pro Gln Phe
385                 390                 395                 400

His Lys Gln Lys Pro Asn Glu Leu Ile Val Trp Leu Tyr Gly Leu Tyr
                    405                 410                 415

Ser Asn Thr Lys Gly Asn Tyr Val Lys Lys Thr Met Pro Glu Cys Asp
                420                 425                 430

Gly Ile Glu Leu Cys Glu Glu Trp Leu Tyr His Met Gly Val Pro Glu
            435                 440                 445

Ser Glu Ile Lys Lys Met Ala Ile Asp Ala Thr Thr Ile Pro Asn His
    450                 455                 460

Met Pro Tyr Ile Thr Ser Tyr Phe Met Pro Arg Ala Leu Gly Asp Arg
465                 470                 475                 480

Pro Lys Val Val Pro Lys Asn Ser Lys Asn Leu Ala Phe Ile Gly Asn
                    485                 490                 495

Phe Ala Glu Thr Glu Arg Asp Thr Val Phe Thr Thr Glu Tyr Ser Val
                500                 505                 510

Arg Thr Ala Met Glu Ala Val Tyr Thr Leu Leu Asn Val Asp Arg Gly
            515                 520                 525

Val Pro Glu Val Phe Ala Ser Ala Phe Asp Val Arg Met Leu Met Asn
    530                 535                 540

Ala Met Tyr Tyr Leu Asn Asp Arg Lys Lys Leu Thr Glu Leu Asp Leu
545                 550                 555                 560

Pro Leu Pro Glu Lys Leu Met Val Lys Glu Gly Leu Lys Lys Val Lys
                    565                 570                 575

Gly Thr Tyr Val Glu Glu Leu Leu Lys Lys Tyr Lys Leu Ile
                580                 585                 590

<210> SEQ ID NO 10
<211> LENGTH: 590
<212> TYPE: PRT
<213> ORGANISM: Pediococcus claussenii

<400> SEQUENCE: 10

Met Tyr Tyr Ser Asn Gly Asn Tyr Glu Ala Phe Ala Arg Pro Lys Lys
1               5                   10                  15

Pro Ala Asn Val Asp Gln Lys Ser Ala Tyr Leu Val Gly Ser Gly Leu
                20                  25                  30

Ala Ser Leu Ala Ala Ala Thr Phe Leu Val Arg Asp Gly Gln Met Ala
            35                  40                  45

Gly Asp Arg Ile His Val Leu Glu Glu Leu Gly Leu Pro Gly Gly Ser
    50                  55                  60

Met Asp Gly Ile Trp Asn Glu Gln Lys Gly Tyr Ile Ile Arg Gly Gly
65                  70                  75                  80

Arg Glu Met Glu Pro His Phe Glu Thr Leu Trp Asp Leu Phe Arg Ser
                85                  90                  95

Ile Pro Ser Leu Glu Asn Glu Asp Val Ser Val Leu Asp Glu Tyr Tyr
                100                 105                 110

Trp Leu Asn Lys Glu Asp Pro Ser Phe Ser Lys Ala Arg Val Ile Glu
            115                 120                 125

Asn Arg Gly Gln Arg Met Ala Ser Asp Gly Lys Leu Thr Leu Ser Arg
    130                 135                 140

Lys Ala Ile Asn Glu Ile Ile Lys Val Ala Leu Thr Pro Glu Asp Gln
145                 150                 155                 160
```

```
Leu Gln Asp Lys Gln Ile Asp Glu Val Phe Ser Gln Glu Phe Phe Asp
            165                 170                 175

Ser Asn Phe Trp Leu Tyr Trp Ser Thr Met Phe Ala Phe Glu Pro Trp
        180                 185                 190

Ala Ser Ala Leu Glu Met Arg Arg Tyr Leu Leu Arg Phe Val His His
    195                 200                 205

Ile Ala Thr Leu Ser Asp Leu Ser Ser Leu Arg Phe Thr Lys Tyr Asn
210                 215                 220

Gln Tyr Glu Ser Leu Ile Ile Pro Met Val Lys Phe Leu Glu Ser Lys
225                 230                 235                 240

Gly Val His Phe Gln Tyr Asn Thr Thr Val Asp Asn Ile Leu Val Asn
            245                 250                 255

Arg Val Gly Thr Gly Lys Val Ala Thr Lys Leu Glu Met Thr Val Asp
        260                 265                 270

Gly Lys His Glu Ser Lys Lys Leu Thr Ala Asp Asp Leu Val Phe Val
    275                 280                 285

Thr Asn Gly Ser Ile Thr Glu Ser Thr Thr Tyr Gly Asp Asn Thr His
290                 295                 300

Ala Ala Pro Val Glu His Glu Leu Gly Ala Thr Trp Gln Leu Trp Lys
305                 310                 315                 320

Asn Leu Ala Ala Gln Asp Pro Asp Phe Gly His Pro Glu Lys Phe Tyr
            325                 330                 335

Asp Asn Ile Pro Asp Ala Asn Trp Thr Ile Ser Gly Thr Ile Thr Phe
        340                 345                 350

Asn Asp Asp Arg Val Thr Pro Tyr Ile Glu Lys Ile Ser Gln Lys Asp
    355                 360                 365

Pro His Ser Gly Ser Ile Val Thr Ser Gly Pro Val Ser Ile Lys Asp
370                 375                 380

Ser Asn Trp Leu Leu Gly Tyr Ser Ile Ser Arg Gln Pro His Phe Lys
385                 390                 395                 400

Ala Gln Lys Pro Asn Glu Leu Val Val Trp Val Tyr Gly Leu Phe Ser
            405                 410                 415

Asp Lys Pro Gly Asn Phe Val Asp Lys Lys Ile Thr Glu Cys Thr Gly
        420                 425                 430

Ile Glu Leu Cys Glu Glu Trp Leu Tyr His Ile Gly Val Pro Glu Asp
    435                 440                 445

Gln Ile Val Asp Ile Ala Thr Asn Ser Ala Ser Thr Ile Pro Ala His
450                 455                 460

Met Pro Tyr Ile Thr Ser Tyr Phe Met Pro Arg Ala Leu Gly Asp Arg
465                 470                 475                 480

Pro Leu Val Val Pro Glu Gly Ser Val Asn Leu Ala Phe Ile Gly Asn
            485                 490                 495

Phe Ala Glu Thr Glu Arg Asp Thr Val Phe Thr Glu Tyr Ser Val
        500                 505                 510

Arg Thr Ala Met Glu Ala Val Tyr Thr Leu Leu Asn Val Asp Arg Gly
    515                 520                 525

Val Pro Glu Val Phe Asp Ser Ala Phe Asp Ala Arg Val Leu Met Asn
530                 535                 540

Ala Ile Tyr Tyr Leu Asn Asp Lys Lys Lys Leu Glu Asp Ile Gln Leu
545                 550                 555                 560

Pro Phe Ala Glu Lys Ala Ile Glu Lys Gln Val Leu Arg Lys Ile Lys
            565                 570                 575
```

Gly Thr Tyr Ile Glu Glu Leu Leu Lys Asn Ala His Leu Leu
            580                 585                 590

<210> SEQ ID NO 11
<211> LENGTH: 590
<212> TYPE: PRT
<213> ORGANISM: Lactobacillus ruminis

<400> SEQUENCE: 11

Met Tyr Tyr Ser Asn Gly Asn Tyr Glu Ala Phe Ala Arg Pro Lys Lys
1               5                   10                  15

Pro Ala Gly Val Glu Asn Lys Ser Ala Tyr Ile Val Gly Ser Gly Leu
            20                  25                  30

Ala Ala Leu Ser Thr Ala Val Phe Leu Ile Arg Asp Gly Gln Met Asp
        35                  40                  45

Gly Ala Lys Ile His Leu Leu Glu Glu Leu Ser Leu Pro Gly Gly Ser
    50                  55                  60

Met Asp Gly Ile Lys Asn Glu Arg Leu Gly Tyr Ile Ile Arg Gly Gly
65                  70                  75                  80

Arg Glu Met Glu Pro His Phe Glu Val Leu Trp Asp Leu Phe Arg Ser
                85                  90                  95

Ile Pro Ser Leu Glu Asn Pro Glu His Ser Ile Leu Asp Glu Phe Tyr
            100                 105                 110

Trp Leu Asn Lys Glu Asp Pro Cys Phe Ala Lys Thr Arg Val Ile Tyr
        115                 120                 125

His Gln Gly Gln Glu Ile Pro Asp Asp Gly Gln Leu Thr Leu Ser Lys
    130                 135                 140

Lys Ala Ile Lys Glu Ile Ile Lys Leu Ile Leu Thr Pro Glu Asp Lys
145                 150                 155                 160

Leu Gln Asp Val Gln Ile Asp Gln Val Phe Asp Glu Phe Phe Lys
                165                 170                 175

Ser Asn Phe Trp Leu Tyr Trp Arg Thr Met Phe Ala Phe Glu Pro Trp
            180                 185                 190

Ala Ser Ala Met Glu Met Arg Arg Tyr Leu Met Arg Phe Val Gln His
        195                 200                 205

Val Gly Thr Leu Lys Asn Leu Ser Ser Leu Arg Phe Thr Lys Tyr Asn
    210                 215                 220

Gln Tyr Glu Ser Leu Ile Met Pro Ile Val Ala Tyr Leu Lys Glu His
225                 230                 235                 240

Gly Val Asn Phe Arg Tyr Asp Thr Val Val Thr Asn Ile Ile Val Asn
                245                 250                 255

Arg Thr Gly Ser Asp Lys Val Ala Lys Lys Ile Glu Met Thr Val Ala
            260                 265                 270

Gly Glu Glu Lys Ala Leu Glu Leu Thr Glu Asn Asp Leu Val Phe Val
        275                 280                 285

Thr Asn Gly Ser Ile Thr Glu Ser Thr Tyr Gly Asp Asn Asp His
    290                 295                 300

Ala Ala Pro Val Thr His Glu Leu Gly Ala Ser Trp Gln Leu Trp Glu
305                 310                 315                 320

Asn Leu Ala Ala Gln Asp Glu Ala Phe Gly His Pro Asp Lys Phe Cys
                325                 330                 335

Lys His Ile Pro Asp Ala Asn Trp Thr Val Ser Ala Thr Ile Thr Phe
            340                 345                 350

Lys Asp Ser Arg Val Ala Lys Tyr Ile Glu Arg Val Asn Lys Lys Asp
        355                 360                 365

Pro Tyr Ser Gly Ser Ile Val Ser Ser Gly Pro Thr Ser Ile Lys Asp
        370                 375                 380

Ser Asn Trp Ser Leu Gly Tyr Ser Ile Ser Arg Gln Pro His Phe Lys
385                 390                 395                 400

Ala Gln Gln Pro Asn Glu Leu Val Val Trp Leu Tyr Pro Leu Phe Thr
                405                 410                 415

Asp Arg Ile Gly Asn Tyr Ile Glu Lys Arg Pro Asp Glu Cys Thr Gly
                420                 425                 430

Met Glu Leu Cys Glu Glu Trp Leu Tyr His Met Gly Val Pro Glu Asn
        435                 440                 445

Glu Ile Lys Ala Ile Ser Gln Asp Ala Ser Thr Ile Pro Cys His Met
        450                 455                 460

Pro Tyr Ile Thr Thr Tyr Phe Met Pro Arg Ala Asn Gly Asp Arg Pro
465                 470                 475                 480

Leu Val Val Pro Lys His Cys Lys Asn Leu Ala Phe Ile Gly Asn Tyr
                485                 490                 495

Ala Glu Thr Pro Arg Asp Thr Val Phe Thr Thr Glu Tyr Ser Val Arg
                500                 505                 510

Thr Ala Met Glu Ala Val Tyr Thr Leu Leu Asn Val Asp Arg Gly Val
        515                 520                 525

Pro Glu Val Phe Gly Ser Val Phe Asp Val Arg Met Met Leu Asn Ala
530                 535                 540

Phe Tyr Tyr Leu Asn Asp Gln Lys Ser Leu Glu Leu Asp Leu Ser
545                 550                 555                 560

Trp Pro Glu Lys Thr Ala Val Lys Gly Phe Met Ser Lys Ile Lys Gly
                565                 570                 575

Thr Tyr Ile Glu Glu Leu Met Lys Glu Tyr His Val Ile Lys
        580                 585                 590

<210> SEQ ID NO 12
<211> LENGTH: 589
<212> TYPE: PRT
<213> ORGANISM: Streptococcus infantarius

<400> SEQUENCE: 12

Met Tyr Tyr Ser Asn Gly Asn Tyr Glu Ala Phe Ala Arg Pro Lys Lys
1               5                   10                  15

Pro Glu Asn Val Asp Glu Lys Ser Ala Tyr Ile Val Gly Ser Gly Leu
                20                  25                  30

Ala Ala Leu Ser Thr Ala Val Phe Leu Val Arg Asp Ala Gln Met Ser
            35                  40                  45

Gly Asp His Ile His Ile Leu Glu Glu Leu Ser Leu Pro Gly Gly Ser
        50                  55                  60

Met Asp Gly Ile Lys Asn Asp Arg Leu Gly Tyr Ile Ile Arg Gly Gly
65                  70                  75                  80

Arg Glu Met Glu Pro His Phe Glu Val Leu Trp Asp Leu Phe Arg Ser
                85                  90                  95

Ile Pro Ser Leu Glu Asn Pro Asp His Ser Ile Leu Asp Glu Phe Tyr
                100                 105                 110

Trp Leu Asn Lys Glu Asp Pro Cys Tyr Ala Lys Thr Arg Val Ile Cys
            115                 120                 125

Asn Arg Gly Lys Ala Leu Pro Asn Asp Gly Gln Leu Thr Leu Ser Glu
        130                 135                 140

Lys Ala Ile Lys Glu Met Ile Asp Leu Ile Leu Met Pro Glu Ser Lys

```
                145                 150                 155                 160
        Leu Glu Asn Val Gln Ile Asp Gln Val Phe Asp Asp Glu Phe Phe Asn
                        165                 170                 175
        Ser Asn Phe Trp Leu Tyr Trp Cys Thr Met Phe Ala Phe Glu Pro Trp
                        180                 185                 190
        Ser Ser Ala Met Glu Met Arg Arg Tyr Leu Met Arg Phe Ile Gln His
                        195                 200                 205
        Val Ser Cys Leu Lys Asn Leu Ser Ser Leu Arg Phe Thr Lys Tyr Asn
                210                 215                 220
        Gln Tyr Glu Ser Leu Ile Leu Pro Ile Val His Tyr Leu Ser Glu His
        225                 230                 235                 240
        Gly Val Asp Phe Asn Tyr Asp Thr Thr Val Thr Asn Ile Leu Val Asn
                        245                 250                 255
        Arg Lys Gly Asn Lys Lys Val Ala Ser Lys Leu Glu Phe Thr Lys Ala
                        260                 265                 270
        Gly Gln Val Lys Glu Leu Phe Leu Ser Glu Asn Asp Leu Val Phe Val
                        275                 280                 285
        Thr Asn Gly Ser Ile Thr Glu Ser Thr Thr Tyr Gly Asp Asn Asp His
                290                 295                 300
        Pro Ala Pro Val Lys His Glu Leu Gly Ala Ser Trp Glu Leu Trp Gln
        305                 310                 315                 320
        Lys Leu Ala Ala Gln Asp Glu Ser Phe Gly His Pro Glu Lys Phe Cys
                        325                 330                 335
        Gln Asn Ile Pro Asp Ala Asn Trp Thr Ile Ser Ala Thr Ile Thr Phe
                        340                 345                 350
        Lys Asp Lys Arg Ile Ser Pro Tyr Ile Glu Ala Val Asn His Lys Asp
                        355                 360                 365
        Pro Tyr Ser Gly Ser Ile Val Thr Ser Gly Pro Thr Ser Ile Lys Asp
                        370                 375                 380
        Ser Asn Trp Leu Leu Gly Tyr Ser Ile Ser Arg Gln Pro His Phe Lys
        385                 390                 395                 400
        Val Gln Lys Asp Asn Glu Leu Val Val Trp Leu Tyr Ser Leu Tyr Thr
                        405                 410                 415
        Asp Arg Lys Gly Asn Tyr Ile Ala Lys Arg Pro Asp Glu Cys Thr Gly
                        420                 425                 430
        Lys Glu Leu Cys Gln Glu Trp Leu Tyr His Met Gly Val Pro Glu Thr
                        435                 440                 445
        Glu Ile Ala Glu Ile Ala Asp Thr Ala Ser Thr Ile Pro Cys His Met
                450                 455                 460
        Pro Tyr Ile Thr Thr Tyr Phe Met Pro Arg Gly Leu Asn Asp Arg Pro
        465                 470                 475                 480
        Leu Val Val Pro Lys Asp Ser Gln Asn Leu Ala Phe Ile Gly Asn Tyr
                        485                 490                 495
        Ala Glu Thr Pro Arg Asp Thr Val Phe Thr Thr Glu Tyr Ser Val Arg
                        500                 505                 510
        Thr Ala Met Glu Ala Val Tyr Thr Leu Leu Asp Val Asp Arg Gly Val
                        515                 520                 525
        Pro Glu Val Phe Ala Ser Ala Phe Asp Val Arg Met Leu Leu Asn Ala
                        530                 535                 540
        Leu Tyr Tyr Leu Asn Asp Gln Lys Ser Leu Thr Glu Ile Asp Ile Pro
        545                 550                 555                 560
        Trp Ala Glu Lys Ala Val Leu Lys Glu Ala Leu Lys Lys Val His Gly
                        565                 570                 575
```

Thr Tyr Leu Glu Glu Leu Leu Lys Glu Tyr His Leu Leu
            580                 585

<210> SEQ ID NO 13
<211> LENGTH: 589
<212> TYPE: PRT
<213> ORGANISM: Streptococcus mutans

<400> SEQUENCE: 13

Met Tyr Tyr Ser Asn Gly Asn Tyr Glu Ala Phe Ala His Ser Gln Lys
1               5                   10                  15

Pro Glu Asn Val Asp Gly Lys Ser Ala Tyr Ile Val Gly Ser Gly Leu
            20                  25                  30

Ala Ala Leu Ser Thr Ala Val Phe Leu Ile Arg Asp Gly Gln Met Ala
        35                  40                  45

Gly Glu Arg Ile His Ile Leu Glu Glu Leu Ser Leu Pro Gly Gly Ser
    50                  55                  60

Met Asp Gly Ile Arg Asn Glu Arg Leu Gly Tyr Ile Ile Arg Gly Gly
65                  70                  75                  80

Arg Glu Met Glu Pro His Phe Glu Val Leu Trp Asp Leu Phe Arg Ser
                85                  90                  95

Ile Pro Ser Leu Glu Asn Pro Lys His Ser Ile Leu Asp Glu Phe Tyr
            100                 105                 110

Trp Leu Asn Lys Lys Asp Pro Ser Phe Ala Lys Thr Arg Ala Ile Tyr
        115                 120                 125

Glu Arg Gly Lys Ala Ile Pro Asp Asp Gly Gln Leu Thr Leu Ser Gln
    130                 135                 140

Lys Ala Val Lys Glu Ile Phe Asp Leu Val Leu Thr Pro Glu Ser His
145                 150                 155                 160

Leu Gln Asp Val Gln Ile Asp Gln Val Phe Ser Glu Asp Phe Phe Asn
                165                 170                 175

Ser Asn Phe Trp Leu Tyr Trp Ser Thr Met Phe Ala Phe Glu Pro Trp
            180                 185                 190

Ala Ser Ala Met Glu Met Arg Arg Tyr Leu Met Arg Phe Ile Gln His
        195                 200                 205

Val Gly Thr Leu Lys Asn Leu Ser Ser Leu Lys Phe Thr Gln Tyr Asn
    210                 215                 220

Gln Tyr Glu Ser Leu Ile Leu Pro Leu Val Ala Phe Leu Lys Asp His
225                 230                 235                 240

Asn Val Asn Phe Ser Tyr Gln Thr Val Val Thr Asn Ile Leu Val Asn
                245                 250                 255

Arg Ser Gly Ser Asp Lys Leu Ala Thr Lys Ile Glu Met Thr Val Asn
            260                 265                 270

Gly Gln Glu Lys Ser Ile Ala Leu Ser Arg Asp Asp Leu Val Phe Val
        275                 280                 285

Thr Asn Gly Ser Ile Thr Glu Ser Ser Thr Tyr Gly Asn Asn Asn His
    290                 295                 300

Pro Ala Pro Leu Thr His Asp Leu Gly Ala Ser Trp Gln Leu Trp Lys
305                 310                 315                 320

Asn Leu Ala Ala Gln Asp Ser Asp Phe Gly Cys Pro Glu Lys Phe Cys
                325                 330                 335

Glu Asn Ile Pro Asp Ala Asn Trp Thr Met Ser Ala Thr Ile Thr Phe
            340                 345                 350

Thr Asp Gln Arg Ile Ala Lys Tyr Ile Glu Gln Ile Asn Gln Lys Asp

```
                355                 360                 365
Pro Tyr Ser Gly Ser Ile Val Thr Ser Gly Pro Thr Ser Ile Lys Asp
370                 375                 380

Ser Ser Trp Leu Leu Gly Tyr Ser Ile Ser Arg Gln Pro His Phe Lys
385                 390                 395                 400

Glu Gln Lys Lys Asn Glu Leu Val Ile Trp Leu Tyr Ala Leu Tyr Thr
                405                 410                 415

Asp Arg Lys Gly Asp Tyr Val Ala Lys Arg Pro Asp Glu Cys Thr Gly
                420                 425                 430

Ile Glu Met Cys Glu Glu Trp Leu Tyr His Ile Gly Val Pro Glu Asn
                435                 440                 445

Thr Ile His Glu Leu Ala Cys Ser Ala Ser Thr Ile Pro Cys His Met
                450                 455                 460

Pro Tyr Ile Thr Thr Tyr Phe Met Pro Arg Thr Thr Asn Asp Arg Pro
465                 470                 475                 480

Leu Val Val Pro Lys His Ser Lys Asn Leu Ala Phe Ile Gly Asn Tyr
                485                 490                 495

Ala Glu Thr Pro Arg Asp Thr Val Phe Thr Thr Glu Tyr Ser Val Arg
                500                 505                 510

Thr Ala Met Glu Ala Val Tyr Thr Leu Leu Glu Val Asp Arg Gly Val
                515                 520                 525

Pro Glu Val Phe Ala Ser Thr Phe Asp Ile Arg Met Leu Leu Asn Ala
                530                 535                 540

Leu Tyr Tyr Leu Asn Gly Gln Lys Ser Leu Ile Glu Ile Asp Phe Pro
545                 550                 555                 560

Trp Val Glu Lys Ala Ala Leu Lys Glu Ala Leu Lys Lys Val Lys Gly
                565                 570                 575

Thr Tyr Ile Glu Glu Leu Leu Lys Asp Tyr His Leu Ile
                580                 585

<210> SEQ ID NO 14
<211> LENGTH: 589
<212> TYPE: PRT
<213> ORGANISM: Streptococcus equinus

<400> SEQUENCE: 14

Met Tyr Tyr Ser Asn Gly Asn Tyr Glu Ala Phe Ala Arg Pro Lys Lys
1               5                   10                  15

Pro Glu Asn Val Asp Gln Lys Ser Ala Tyr Ile Val Gly Ser Gly Leu
                20                  25                  30

Ala Ala Leu Ser Thr Ala Val Phe Leu Val Arg Asp Ala Gln Met Pro
                35                  40                  45

Gly Asp His Ile His Ile Leu Glu Glu Leu Lys Leu Pro Gly Gly Ser
                50                  55                  60

Met Asp Gly Ile Lys Asn Asp Arg Leu Gly Tyr Ile Ile Arg Gly Gly
65                  70                  75                  80

Arg Glu Met Glu Pro His Phe Glu Val Leu Trp Asp Leu Phe Arg Ser
                85                  90                  95

Ile Pro Ser Leu Glu Asn Pro Glu Asn Ser Ile Leu Asp Glu Phe Tyr
                100                 105                 110

Trp Leu Asn Lys Glu Asp Pro Cys Tyr Ala Lys Thr Arg Val Ile His
                115                 120                 125

Asp Arg Gly Lys Ala Ile Pro Asn Asp Gly Gln Leu Thr Leu Ser Glu
                130                 135                 140
```

-continued

Lys Ala Ile Lys Glu Ile Ile Ser Leu Ile Leu Thr Pro Glu Ser Lys
145                 150                 155                 160

Leu Ala Asn Val Gln Ile Asp Gln Val Phe Thr Asp Glu Phe Phe Lys
                165                 170                 175

Ser Asn Phe Trp Leu Tyr Trp Cys Thr Met Phe Ala Phe Glu Pro Trp
            180                 185                 190

Ser Ser Ala Met Glu Met Arg Arg Tyr Leu Met Arg Phe Ile Gln His
        195                 200                 205

Val Gly Cys Leu Lys Asn Leu Ser Ser Leu Arg Phe Thr Lys Tyr Asn
    210                 215                 220

Gln Tyr Glu Ser Leu Ile Leu Pro Ile Val His Tyr Leu Thr Glu His
225                 230                 235                 240

Gly Val Asp Phe Ser Tyr Asn Thr Thr Val Thr Asn Ile Leu Val Asn
                245                 250                 255

Arg Lys Gly Gln Asp Lys Val Ala Thr Lys Ile Glu Phe Ser Lys Asp
                260                 265                 270

Gly Gln Ala Lys Glu Leu Phe Leu Thr Pro Asp Asp Leu Val Phe Val
            275                 280                 285

Thr Asn Gly Ser Ile Thr Glu Ser Thr Thr Tyr Gly Asp Asn Asp His
290                 295                 300

Pro Ala Pro Val Glu His Asp Leu Gly Ala Ser Trp Glu Leu Trp Lys
305                 310                 315                 320

Lys Leu Ala Ala Gln Asp Asp Ser Phe Gly His Pro Glu Val Phe Cys
                325                 330                 335

Gln Asn Ile Pro Asp Ala Asn Trp Thr Ile Ser Ala Thr Ile Thr Phe
                340                 345                 350

Lys Asp Lys Arg Ile Ala Pro Tyr Ile Glu Ala Val Asn His Lys Asp
                355                 360                 365

Pro Tyr Ser Gly Ser Ile Val Thr Ser Gly Pro Thr Ser Ile Lys Asp
                370                 375                 380

Ser Asn Trp Leu Leu Gly Tyr Ser Ile Ser Arg Gln Pro His Phe Lys
385                 390                 395                 400

Thr Gln Lys Asp Asn Glu Leu Val Val Trp Leu Tyr Pro Leu Tyr Thr
                405                 410                 415

Asp Arg Lys Gly Asn Phe Val Asp Lys Arg Pro Asp Gln Cys Ser Gly
                420                 425                 430

Lys Glu Leu Cys Gln Glu Trp Leu Tyr His Met Gly Val Pro Glu Ala
                435                 440                 445

Asp Ile Lys Glu Met Ala Glu Ser Ala Ser Thr Ile Pro Cys His Met
450                 455                 460

Pro Tyr Ile Thr Thr Tyr Phe Met Pro Arg Gly Leu Asn Asp Arg Pro
465                 470                 475                 480

Leu Val Val Pro Glu His Ser Lys Asn Leu Ala Phe Ile Gly Asn Tyr
                485                 490                 495

Ala Glu Thr Pro Arg Asp Thr Val Phe Thr Thr Glu Tyr Ser Val Arg
                500                 505                 510

Thr Ala Met Glu Ala Val Tyr Thr Leu Leu Lys Val Asp Arg Gly Val
            515                 520                 525

Pro Glu Val Phe Ala Ser Phe Asp Val Arg Met Ile Leu Asn Ala
            530                 535                 540

Leu Tyr Tyr Leu Asn Asp Gln Lys Ser Leu Thr Glu Ile Asp Ile Pro
545                 550                 555                 560

Trp Thr Glu Lys Ala Val Leu Lys Glu Ser Leu Lys Lys Ile His Gly

Thr Tyr Ile Glu Glu Leu Leu Lys Glu Tyr His Leu Leu
           580              585

<210> SEQ ID NO 15
<211> LENGTH: 1773
<212> TYPE: DNA
<213> ORGANISM: Lactobacillus acidophilus

<400> SEQUENCE: 15

| | | | | | |
|---|---|---|---|---|---|
| atgcactaca | gcagcggtaa | ctatgaggcg | ttcgttaacg | cgagcaagcc | gaaagatgtg | 60 |
| gaccaaaaga | gcgcgtatct | ggttggtagc | ggtctggcga | gcctggcgag | cgcggtgttt | 120 |
| ctgatccgtg | atggtcacat | gaaaggcgac | cgtatccaca | ttctggagga | actgagcctg | 180 |
| ccgggtggca | gcatggatgg | catttacaac | aagcagaaag | agagctatat | cattcgtggt | 240 |
| ggccgtgaga | tggaagcgca | cttcgaatgc | ctgtgggacc | tgtttcgtag | catcccgagc | 300 |
| gcggagaaca | aggatgaaag | cgttctggac | gagttctacc | gtctgaaccg | taaggatccg | 360 |
| agctttgcga | aaacccgtgt | gattgttaac | cgtggtcacg | aactgccgac | cgatggtcaa | 420 |
| ctgctgctga | ccccgaaggc | ggtgaaagag | atcattgatc | tgtgcctgac | cccggaaaag | 480 |
| gacctgcaga | caagaaaat | caacgaagtt | ttcagcaaag | agttctttga | aagcaacttt | 540 |
| tggctgtact | ggagcaccat | gttcgcgttt | gagccgtggg | cgagcgcgat | ggaaatgcgt | 600 |
| cgttatctga | tgcgtttcgt | gcagcacgtt | agcaccctga | gaacctgag | cagcctgcgt | 660 |
| tttaccaaat | acaaccaata | tgagagcctg | atcctgccga | tggtgaagta | cctgaaagat | 720 |
| cgtggtgttc | agttccacta | taacaccgtg | gttgacaaca | tttttgtgaa | ccgtagcaac | 780 |
| ggtgaaaaga | tcgcgaaaca | aattctgctg | accgagaacg | gcgaaaagaa | aagcatcgat | 840 |
| ctgaccgaga | acgacctggt | gttcgttacc | aacggtagca | ttaccgaaag | caccacctac | 900 |
| ggcgataacc | tgcaccccgc | gagcgaggaa | cacaagctgg | gtgcgacctg | gaaactgtgg | 960 |
| cagaacctgg | cggcgcaaga | cgatgacttc | ggccacccgg | atgtgttttg | caaggacatc | 1020 |
| ccgaaagcga | actgggttat | gagcgcgacc | attaccttca | aaaacaacga | tatcgtgccg | 1080 |
| tttattgagg | cggttaacaa | gaaagacccg | cacagcggta | gcatcgtgac | cagcggcccg | 1140 |
| accaccatta | aggacagcaa | ctggctgctg | ggttacagca | tcagccgtca | gccgcacttc | 1200 |
| gaggcgcaaa | aaccgaacga | actgattgtg | tggctgtacg | gtctgtttag | cgataccaag | 1260 |
| ggcaactatg | ttgagaaaac | catgccggac | tgcaacggta | tcgaactgtg | cgaggaatgg | 1320 |
| ctgtatcaca | tgggcgttcc | ggaggaacgt | attccggaaa | tggcgagcgc | ggcgaccacc | 1380 |
| atcccggcgc | acatgccgta | cattaccagc | tatttcatgc | cgcgtgcgct | gggtgatcgt | 1440 |
| ccgaaggtgt | ttccggacca | cagcaaaaac | ctggcgttca | tcggcaactt | tgcggagacc | 1500 |
| ccgcgtgata | ccgtgttcac | caccgagtac | agcgttcgta | ccgcgatgga | agcggtgtat | 1560 |
| accctgctga | acattgatcg | tggtgtgccg | gaagttttcg | cgagcgcgtt | tgacgttcgt | 1620 |
| atgctgatga | acgcgatgta | ctatctgaac | gaccagaaga | aactggagga | tctggacctg | 1680 |
| ccgatcgcgg | aaaagctggc | gattaagggt | atgctgaaga | agtgaaggg | cacctacatc | 1740 |
| gaggaactgc | tgaagaaata | taaactggtt | taa | | | 1773 |

<210> SEQ ID NO 16
<211> LENGTH: 1773
<212> TYPE: DNA
<213> ORGANISM: Lactobacillus amylovorus

<400> SEQUENCE: 16

```
atgcactaca gcaacggtaa ctatgaggcg ttcgttaacg cgagcaagcc gaaagacgtg      60
gatcaaaaga gcgcgtacat cgttggtagc ggtctggcgg cgctggcgag cgcggtgttc     120
ctgattcgtg acggtcacat gaaaggcgaa cgtatccaca tttttgagga actgggtctg     180
ccgggtggca gcatggatgg catctacaac aagcagaaag agagctatat cattcgtggt     240
ggccgtgaga tggaaccgca cttcgaatgc ctgtgggacc tgtttcgtag cattccgagc     300
ccggagaaca aggacgaaag cgtgctggat gagttctacc gtctgaaccg tcgtgacccg     360
agctatgcga aacccgtgt gatcgttaac cgtggtgaag cgctgccgac cgatggccaa     420
ctgctgctga ccccgaaggc ggtgaaagag atcgttgacc tgtgcctgac cccggaaaag     480
gatctgcaga caagaaaat taacgaggtt ttcgacaaag aattctttca aagcaacttt     540
tggctgtact ggagcaccat gttcgcgttt gagccgtggg cgagcgcgat ggaaatgcgt     600
cgttatctga tgcgtttcgt gcagcacgtt gcgaccctga gaacctgag cagcctgcgt     660
tttaccaaat acaaccaata tgagagcctg atcctgccga tggtgaagta cctgaaagat     720
cacggtgttc agttccacta tgacaccgtg gttgataacg tgtttgttaa ccgtagcaac     780
ggtgaaaagg ttgcgaaaca gatcattctg accgagaacg gcgaaaagaa aaacatcgac     840
ctgaccgaga cgatctggt gttcgttacc aacggtagca ttaccgaaag caccacctac     900
ggcgacaacc tgcacccggc gccggaggaa catgagctgg gtgcgagctg gcagctgtgg     960
aagaacctgg cggcgcaaga cgaggatttc ggccacccgg aagtgttttg caaggatatc    1020
ccgaaagcga actggcgtat gagcgcgacc attaccttca gaacaacga catcgtgccg    1080
tttattgagg cggttaacaa gaaagatccg cacagcggta gcatcgttac cagcggcccg    1140
accaccatta agacagcaa ctggctgctg ggttacagca tcagccgtca gccgcacttc    1200
aaggcgcaaa accgaacga actgattgtg tggctgtacg gtctgtttag cgacaccaag    1260
ggcaactatg ttgagaaaac catgccggat tgcaacggta tcgaactgtg cgaggaatgg    1320
ctgtatcaca tgggcgtgcc ggaggaacgt atcccggaga tggcggcggc ggcgaccacc    1380
atcccggcgc acatgccgta cattaccagc tatttcatgc cgcgtgcgct gggtgaccgt    1440
ccgaaggtgg ttccggatca cagcaaaaac ctggcgttca ttggcaactt tgcggagacc    1500
ccgcgtgaca ccgtgtttac caccgagtac agcgttcgta ccgcgatgga agcggtgtat    1560
accctgctgg acatcgatcg tggcgtgccg gaagttttcg cgagcgcgtt tgatgttcgt    1620
atgctgatga cgcgatgta ctatctgaac gaccaaaaga aactggagga actggatctg    1680
ccgatcccgg aaaagatggc gattaagggt atgctgaaga agtgaagggg cacctacgtt    1740
gaggaactgc tgaagaaata taaactgatc taa                                 1773
```

<210> SEQ ID NO 17
<211> LENGTH: 1773
<212> TYPE: DNA
<213> ORGANISM: Lactobacillus helveticus

<400> SEQUENCE: 17

```
atgcactaca gcaacggtaa ctatgaagcg ttcgttaagg cggagaagcc gaaagacgtg      60
gatcagaaga gcgcgtacat cgttggtagc ggtctggcgg cgctggcgag cgcggtgttc     120
ctgattcgtg acggtcagat gaaggggcaac cgtatccaca tttttgagga actgagcctg     180
ccgggtggca gcatggatgg catctacagc aaggagaaag aaagctatat cattcgtggt     240
ggccgtgaga tggaaccgca cttcgaatgc ctgtgggacc tgtttcgtag catcccgagc     300
```

```
accgagcacg aaggcgagag cattctggac gagttctacc gtctgaaccg taaggatccg    360
agctatgcga aaacccgtgt gatcattaac cgtggtgaag cgctgccgac cgatggccaa    420
ctgctgctga ccccgaaggc ggtgaaagaa atcgttgacc tgtgcctgac cccggagaag    480
gatctgcaga acaagaaaat taacgaagtt ttcaccaagg agttctttca aagcaacttt    540
tggctgtact ggagcaccat gttcgcgttt gaaccgtggg cgagcgcgat ggagatgcgt    600
cgttatctga tgcgtttcgt gcagcacgtt gcgaccctga gaacctgag cagcctgcgt     660 tttaccaaat acaaccaata tgagagcctg atcctgccga tggtgaagta cctgaaaagc    720
cacggtgttc agttccacta tgacaccgtg gttgataaca tttttgtgaa ccgtagcaac    780
ggcgaaaagg ttgcgaaaca gatcattctg accgaaaagg gcgagcgtaa aaccatcgac    840
ctgaccgaaa acgatctggt gttcgttacc aacggcagca ttaccgagag caccacctac    900
ggtgacaact tcatccggc gagcgaggaa catgagctgg gtgcgagctg cagctgtgg      960 aagaacctgg cggcgcaaga cagcgatttc ggtcacccgg acgtgttttg caaggatatc   1020
ccgaaagcga actggcgtat gagcgcgacc attaccttca gaacgacga tatcgtgccg    1080 tttattgagg cggttaacaa gaaagacccg cacagcggta gcatcgttac cagcggcccg   1140
accaccatta agatagcaa ctggctgctg ggctacagca tcagccgtca gccgcacttc     1200
aaggcgcaaa aaccgaacga actgattgtg tggctgtacg gtctgtttag cgacaccaag   1260
ggcaactatg ttgaaaaaac catgccggat tgcaacggca tcgagctgtg cgaggaatgg   1320
ctgtatcaca tgggtgttcc ggaggaacgt atcccggaga tggcggcggc ggcgaccacc   1380
atcccggcgc acatgccgta cattaccagc tatttcatgc cgcgtgcgct gggtgaccgt   1440
ccgaaggtgg ttccggatca cagcaaaaac ctggcgttca tcggtaactt tgcggagacc   1500
ccgcgtgaca ccgtgtttac caccgaatac agcgttcgta ccgcgatgga ggcggtgtat   1560
accctgctgg acatcgatcg tggtgtgccg gaagttttcg cgagcgcgtt tgacgtgcgt   1620
atgctgatga cgcgctgta ctatctgaac gatcaaaaga aactggaaga cctggatctg    1680
ccgatgggcg agaagctggc gatcaaaggc atgctgaaga agttaaagg tacctacatc    1740 gaggaactga tgaaggaata taaactgatt taa                                1773
```

<210> SEQ ID NO 18
<211> LENGTH: 1773
<212> TYPE: DNA
<213> ORGANISM: Lactobacillus gallinarum

<400> SEQUENCE: 18

```
atgcactaca gcaacggtaa ctatgaagcg ttcgttaagg cggagaagcc gaaagacgtg     60
gatcagaaga gcgcgtacat cgttggtagc ggtctggcgg cgctggcgag cgcggtgttc    120
ctgattcgtg acggtcagat gaagggcaac cgtatccaca tttttgagga actggcgctg    180
ccgggtggca gcatggatgg tatctacaac aaggagaaaa aaagctatat cattcgtggt    240
ggccgtgaga tggaaccgca cttcgaatgc ctgtgggacc tgtttcgtag catcccgagc    300
accgagcacg aaggcgagag cattctggac gagttctacc gtctgaaccg taaggatccg    360
agctatgcga aaacccgtgt gatcattaac cgtggtgaag cgctgccgac cgatggccaa    420
ctgctgctga ccccgaaggc ggttaaagaa atcattgacc tgtgcctgac cccggagaag    480
gatctgcaga acaagaaaat caacgaagtg ttcaccaagg agttctttca aagcaacttt    540
tggctgtact ggagcaccat gttcgcgttt gaaccgtggg cgagcgcgat ggagatgcgt    600
```

-continued

| | |
|---|---|
| cgttatctga tgcgtttcgt gcagcacgtt gcgaccctga gaacctgag cagcctgcgt | 660 |
| tttaccaaat acaaccaata tgagagcctg atcctgccga tggtgaagta cctgaaaggt | 720 |
| cacggcgttc agttccacta tgacaccgtg gttgataaca ttttgttaa ccgtagcgac | 780 |
| ggtaagaaag tggcgaagca gatcgttctg accgaaaagg gcgagcgtaa aaccattgac | 840 |
| ctgaccgaaa acgatctggt gttcgttacc aacggtagca tcaccgagag caccacctac | 900 |
| ggcgacaact tcatccggc gccggcggaa catgagctgg gtgcgagctg cagctgtgg | 960 |
| aaaaacctgg cggcgcaaga cgaagatttc ggccacccgg aagtgttctg ccgtgatatc | 1020 |
| ccgaaggcga actggcgtat gagcgcgacc attaccttca aaaacgacga tatcgtgccg | 1080 |
| tttattgagg cggttaacaa gaaagacccg cacagcggta gcatcgttac cagcggcccg | 1140 |
| accaccatta agatagcaa ctggctgctg ggttacagca tcagccgtca gccgcacttc | 1200 |
| aaggcgcaaa accgaacga actgattgtg tggctgtacg gtctgtttag cgacaccaag | 1260 |
| ggcaactatg ttgaaaaaac catgccggat gcaacggta tcgagctgtg cgaggaatgg | 1320 |
| ctgtatcaca tgggcgttcc ggaggaacgt attccggaaa tggcggcggc ggcgaccacc | 1380 |
| atcccggcgc acatgccgta cattaccagc tatttcatgc cgcgtgcgct gggtgaccgt | 1440 |
| ccgaaggtgg ttccggatca cagcaaaaac ctggcgttca tcggcaactt tgcggagacc | 1500 |
| ccgcgtgaca ccgtgtttac caccgaatac agcgttcgta ccgcgatgga ggcggtgtat | 1560 |
| accctgctgg acattgatcg tggtgtgccg gaagttttcg cgagcgcgtt tgacgtgcgt | 1620 |
| atgctgatga cgcgatgta ctatctgaac gatcaaaaga aactggaaga cttcgatctg | 1680 |
| ccgatgccgg agaagctggt tatcaaaggt attctgaaga agtgaagggg cacctacgtt | 1740 |
| gaggaactga tgaagaaata taaactgatc taa | 1773 |

<210> SEQ ID NO 19
<211> LENGTH: 1773
<212> TYPE: DNA
<213> ORGANISM: Lactobacillus crispatus

<400> SEQUENCE: 19

| | |
|---|---|
| atgcactaca gcaacggtaa ctatgaggcg ttcgttaagg cggacaagcc gaaagacgtg | 60 |
| gatcagaaaa gcgcgtacat tgttggtagc ggtctggcgg cgctggcgac cgcggtgttc | 120 |
| ctgatccgtg acggtcaaat gaagggcgag aaaatccaca ttttgagga actgggtctg | 180 |
| ccgggtggca gcatggatgg catttacaac aaggagaaag aaagctatat cattcgtggt | 240 |
| ggccgtgaga tggaaccgca cttcgaatgc ctgtgggacc tgttccgtag catcccgagc | 300 |
| ccggaccatg agggcgaaag cattctggat agcttctacc gtctgaaccg taaggacccg | 360 |
| agctatgcga aaacccgtgt gatcgttaac cgtggtcagg cgctgccgac cgatggtcaa | 420 |
| ctgctgctga ccccgaaggc ggtgaaagag attgttgacc tgtgcctgac cccggaaaag | 480 |
| gatctgcaga acaagaaaat caacgaagtt tcaccaaag agttcttga aagcaacttt | 540 |
| tggctgtact ggagcaccat gttcgcgttt gagccgtggg cgagcgcgat ggaaatgcgt | 600 |
| cgttatctga tgcgtttcgt gcagcacgtt gcgaccctga gaacctgag cagcctgcgt | 660 |
| tttaccaaat acaaccaata tgagagcctg atcctgccgc tggtgaagta cctgaaagac | 720 |
| cgtggtgtta tcttccacta taacaccgtg gttgacaaca ttttgtgaa ccgtagcgat | 780 |
| ggtgaaaagg ttgcgaaaca gatcattctg accgaggacg gcgaaaagaa aaccattgac | 840 |
| ctgaccccga cgatctggt gttcgttacc aacggtagca tcaccgagag caccacctac | 900 |
| ggcgatcaac tgcatccggc gccggcgag catgaactgg gtgcgagctg cagctgtgg | 960 |

```
aagaacctgg cggcgcaaga cgaagatttc ggccacccgg acgtgttttg caaggatatc    1020
ccgaaagcga actggcgtat gagcgcgacc attaccttca agaacgacga tgtggttccg    1080
tttatcgagg cggtgaacaa gaaagacccg cacagcggta gcatcgttac cagcggcccg    1140
accaccatta agatagcaa ctggctgctg gttacagca ttagccgtca gccgcacttc     1200
```
(Note: line 1200 as shown)

```
accaccatta aagatagcaa ctggctgctg gttacagca ttagccgtca gccgcacttc    1200
aaggcgcaaa aaccgaacga actgatcgtg tggctgtacg gtctgtttag cgacaccaag    1260
ggcaactatg ttgagaaaac catgccggat tgcaacggtc tggaaatgtg cgaggaatgg    1320
ctgtatcaca tgggcgtgcc ggaggaacgt attccggaga ttgcggcggc ggcgaccacc    1380
atcccggttc acatgccgta cattaccagc tatttcatgc cgcgtgcgct gggtgaccgt    1440
ccgaaggtgg ttccggagca cagcaaaaac ctggcgttca ttggcaactt tgcggaaacc    1500
ccgcgtgata ccgtgtttac caccgagtac agcgttcgta ccgcgatgga agcggtgtat    1560
accctgctgg acatcgatcg tggtgtgccg gaagtgttcg cgagcgcgtt tgacgtgcgt    1620
atgctgatga cgcgatgta ctatctgaac gatcaaaaga aactggttga cctggatctg    1680
ccgatgccgg aaaagctggc gatcaagggt atgctgaaga agttaagggg cacctacatc    1740
gaggaactga tgaagaaata taaactgatt taa                                1773
```

<210> SEQ ID NO 20
<211> LENGTH: 1773
<212> TYPE: DNA
<213> ORGANISM: Lactobacillus kefiranofaciens

<400> SEQUENCE: 20

```
atgcactaca gcaacggtaa ctatgaagcg ttcgttaagg cggagaagcc gaaagacgtg     60
gatcagaaga gcgcgtacat cgttggtagc ggtctggcgg cgctggcgag cgcggttttt    120
ctgattcgtg acggtcagat gaagggcgag cacatccaca ttctggagga actgggtctg    180
ccgggtggca gcatggatgg catctacaac aaggagaaag aaagctatat cattcgtggt    240
ggccgtgaga tggaaccgca cttcgaatgc ctgtgggacc tgtttcgtag catcccgagc    300
accgagcacg aaggcgagag cattctggac gagttctacc gtctgaaccg tcgtgatccg    360
agctatgcga aaacccgtgt gatcgttaac cgtggtcagg cgctgccgac cgatggtcaa    420
ctgctgctga ccccgaaggc ggtgaaagaa attgttgacc tgtgcctgac cccggagaag    480
gatctgcaaa acaagaaaat caacgaagtg ttcaccaaag aattctttga gagcaacttt    540
tggctgtact ggagcaccat gttcgcgttt gaaccgtggg cgagcgcgat ggagatgcgt    600
cgttatctga tgcgtttcgt gcagcacgtt gcgaccctga agaacctgag cagcctgcgt    660
tttaccaaat acaaccaata tgaaagcctg attctgccga tggtgaagta cctgaaagac    720
cacggtgttc agttccacta taacaccatc gtggataact gtttgttaa ccgtagcaac    780 ggcgagaagg ttgcgaaaca gatcattctg accgaaaacg gcgagaagaa agcatcgac    840 ctgaccccga cgatctggt gttcgttacc aacggtagca ttaccgaaag caccacctac    900
ggcgacaaca cccatccggc gccggcggaa tatgagctgg gtgcgagctg gcagctgtgg    960
aagaacctgg cggcgcaaga cgaagatttc ggccacccgg aagtgttctg ccacgatatc    1020
ccgaaggcga actggcgtat gagcgcgacc attaccttca aaaacgacga tatcgtgccg    1080
tttattgagg cggttaacaa gaaagacccg cacagcggta gcatcgttac cagcggcccg    1140
accaccatta aagatagcaa ctggctgctg ggttacagca tcagccgtca gccgcacttc    1200
aaggcgcaaa aaccgaacga actgattgtg tggctgtacg gtctgtttag cgacaccaag    1260
```

```
ggcaactata tccaaaaaac catgccggat tgcagcggca tggagatgtg cgaggaatgg      1320
ctgtaccaca tgggtgttcc ggaaggcaag atcccggaga tggcggcggc ggcgaccacc      1380
atcccggcgc acatgccgta cattaccagc tatttcatgc cgcgtgcgct gggtgaccgt      1440
ccgaaggtgg ttccggatca cagcaaaaac ctggcgttca ttggcaactt tgcggaaacc      1500
ccgcgtgaca ccgtgtttac caccgaatac agcgttcgta ccgcgatgga ggcggtgtat      1560
accctgctgg acatcgatcg tggtgtgccg gaagtgttcg cgagcgcgtt tgacgtgcgt      1620
atgctgatga acgcgatgta ctatctgaac gatcagaaga aactggaaga cctggatgtt      1680
agcatgccgg agaagctggc gatcaaaggt attctgaaga agtgaagggg cacctacatc      1740
gaggaactga tgaagaaata taaactgatt taa                                  1773

<210> SEQ ID NO 21
<211> LENGTH: 1803
<212> TYPE: DNA
<213> ORGANISM: Lactobacillus intestinalis

<400> SEQUENCE: 21
atgctgggtc tgaccaagga agtgttcgac atgcactaca ccaacggcaa ctatgaggcg       60
tttgttcagg cggaaaagcc gaaagatgtg gagaacaaaa gcgcgtacat cgttggtagc      120
ggtctggcga gcctggcgac cgcggttttc ctgattcgtg acgcgcaaat gccgggtgat      180
aagatccaca tttttgagga actggcgctg ccgggtggca gcatggatgg tatctacaac      240
ccggaaaaac aggcgtatat cattcgtggt ggccgtgaga tggaaagcca cttcgagacc      300
ctgtgggacc tgttccgtag catcccgagc ctggaaaaca ggacattag cgtgctggat      360 gagttctacc gtctgaaccg taaggacccg agctatagca aaacccgtgt gatcgttaac      420
cgtggtgagg aactgccgac cgatggcaaa ctgctgctga ccccgaaggc gatcaaagaa      480
attgtggacc tggttctgac cccggagaag gatctgcaaa acaagaaaat taacgaagtt      540
ttcagcaaag agttctttga agcaactttt ggctgtact ggagcaccat gttcgcgttt      600
gaaccgtggg cgagcgcgat ggagatgcgt cgttatctga tgcgtttcgt gcagcacgtt      660
gcgaccctga gaaccctgag cagcctgaag tttaccaaat acaaccaata tgagagcctg      720
atcctgccgc tggttagcta cctgaaagac cacggtgttc agttccacta tgacaccgtg      780
gttgataaca tcattgtgaa ccgtagcgaa ggtaagaaag ttgcgaccga gatcaagctg      840
accgagaacg gcaaggaaaa aaccattcac ctgagcgaag acgatctggt gtttgttacc      900
aacggtagca tcaccgagag caccacctac ggcgacaacc tgcacccggc gagccaggaa      960
cacaagctgg gtgcgagctg gcagctgtgg aaaaacctgg cggcgcaaga cagcgatttc     1020
ggccacccgg agaagtttta tgataacatc ccgaaagcga actgggtgat gagcgcgacc     1080
attaccttca gaacaacga catcgtgccg ttcatcgaaa aggttaacaa gaaagatccg     1140
cacagcggta gcatcgttag cagcggcccg accaccatta ggacagcaa ctggctgctg     1200 ggttacagca tcagccgtca gccgcacttc cgtaagcaaa accgaacga gctgattgtg     1260 tggctgtacg gtctgtatag cgataccaag ggcaactacg ttcaaaaaac catgccggag     1320
tgcaacggta tcgaactgtg cgaggaatgg ctgtatcaca tgggcgtgcc ggaggaaaaa     1380
attgcggaaa tggcgcatgc ggcgaccacc atcccgcagc acatgccgta cattaccagc     1440
tatttcatgc cgcgtgcgct gggtgaccgt ccgaaggtgg ttccggataa cagcaaaaac     1500
ctggcgttca tcggcaactt tgcggaaacc ccgcgtgaca ccgtgtttac caccgaatac     1560
agcgttcgta ccgcgatgga ggcggtgtat accctgctgg acattgatcg tggtgtgccg     1620
```

| | |
|---|---:|
| gaagtgttcg cgagcgcgtt tgacgtgcgt atgctgctga acgcgatgta ctatctgaac | 1680 |
| gatcaaaaga aactgaccga cctggatctg ccgctgaccg agaagctggc gatcaagggt | 1740 |
| atgctgaaga aagttaaagg cacctacatt gaggaactgc tgaagcagta taaactgatg | 1800 |
| taa | 1803 |

<210> SEQ ID NO 22
<211> LENGTH: 1773
<212> TYPE: DNA
<213> ORGANISM: Lactobacillus hamsteri

<400> SEQUENCE: 22

| | |
|---|---:|
| atgcactaca gcaacggtaa ctatgaggcg ttcgttcacg cgagcaagcc gaaagacgtg | 60 |
| gataagaaaa gcgcgtacat cgttggtagc ggtctggcga gcctggcgac cgcgaccttt | 120 |
| ctgctgcgtg acgcgcaaat gaagggcgag aaaatccaca ttctggagga actgagcctg | 180 |
| ccgggtggca gcatggatgg tatctacgat caggtgaagc aaagctatat cattcgtggt | 240 |
| ggccgtgaga tggaaaccca cttcgaaacc ctgtgggacc tgttccgtag cattccgagc | 300 |
| ctggacaacc cggcgagac cgttctggat gaattctacc gtctgaaccg taaggacccg | 360 |
| agctttagca aaacccgtgt gatcgttaac cgtggtgagg aactgccgac cgatggccaa | 420 |
| ctgctgctga ccccgaaggc ggtgaaagag atcgttaacc tgtgcctgac cccggaacgt | 480 |
| gacctgcagg ataagaaaat taacgaggtg ttcagccgtg agttctttga aagcaacttt | 540 |
| tggctgtact gggcgaccat gttcgcgttt gagccgtggg cgagcgcgat ggaaatgcgt | 600 |
| cgttatctga tgcgtttcgt gcagcacgtt gcgaccctga aggacctgag cagcctgcgt | 660 |
| tttaccaaat acaaccaata tgaaagcctg attctgccga tggtgaagtt cctgaaagac | 720 |
| cacggtgttc agtttcacta cgataccgtg gttaacaaca tcattgtgaa ccgtagcaac | 780 |
| ggtgcgaagg ttgcggagga aatcaaaatg accgagaacg gcgaggaaaa gagcattaaa | 840 |
| ctgagcccgg acgatctggt gttcgttacc aacggtagca tcaccgaaag caccacctat | 900 |
| ggcgacaacc tgcacccggc ggatgagcac cacgaatttg gtgcgagctg cagctgtgg | 960 |
| aagaacctgg cggcgcaaga cagcgatttc ggccaccgg agaagttttg cgaaaacatc | 1020 |
| ccgaaagcga actgggtgat gagcgcgacc gttaccttca gaacgacga tattgtgccg | 1080 |
| tttatcgaga aaattaacaa gaaagacccg cacagcggta gcatcgttac cagcggcccg | 1140 |
| accaccatta agatagcaa ctggatgctg ggttacagca tcagccgtca gccgcacttc | 1200 |
| cacaagcaaa aaccgaacga actgattgtg tggctgtacg gtctgtatag cgacaccaac | 1260 |
| ggcaactacg ttaagaaaac catgccggag tgcaacggta tcgaactgtg cgaggaatgg | 1320 |
| ctgtatcaca tgggcgtgcc ggatgagaag attagcgaaa tggcgcatgc ggcggttacc | 1380 |
| atcccggcgc acatgccgta cattaccagc tatttcatgc cgcgtgcgct gggtgaccgt | 1440 |
| ccgaaagtgg ttccggagaa gagcaaaaac ctggcgttca tcggcaactt tgcggagacc | 1500 |
| gaacgtgata ccgtgttcac caccgagtac agcgttcgta ccgcgatgga agcggtgtat | 1560 |
| accctgctgg acatcgatcg tggtattccg gaagttttcg cgagcgcgtt tgacgtgcgt | 1620 |
| atgctgatga cgcgatgta ctatctgaac gaccagaaga aactgaccga gctggatctg | 1680 |
| ccgctgccgg aaaagctggc gatcaagggt atgctgaaga aagttaaggg cacctacatt | 1740 |
| gaggatctgc tgaaagaata tcgtctgatg taa | 1773 |

<210> SEQ ID NO 23

<211> LENGTH: 1773
<212> TYPE: DNA
<213> ORGANISM: Lactobacillus gasseri

<400> SEQUENCE: 23

```
atgcactaca gcaacggtaa ctatgaggcg ttcattaacg cggaaaagcc gaaagacgtg      60
gataacaaga gcgcgtacat cgttggtagc ggtctggcgg cgctggcggc ggcggtgttt     120
ctgattcgtg acggtcacat gaagggcgat aaaatccacg ttctggagga actggcgctg     180
ccgggtggca gcatggatgc gatttacaac gtggcggatc aggcgtatgt tatgcgtggt     240
ggccgtgaga tggaaccgca cttcgagacc ctgtgggacc tgtttcgtag catcccgagc     300
ctggactacc cggatcagag cgtgctggac gagttctacc gtgaaaaccg taaggatccg     360
tgctatagca aaacccgtgt tattgagaac cgtggtcaag aactgccgac cgatggtgat     420
ctgctgctga gcccgaaggc ggtgaaagag attctgaacc tggttatgac cccggaaaag     480
gacctgcagg ataagaaaat caacgaggtg ttcgacgatg aattctttaa aagcaacttt     540
tggctgtact ggcaaaccat gttcgcgttt atgccgtggg cgagcgcgat ggagatgcgt     600
cgttatctga tgcgtttcgt gcagcacgtt gcgaccctga gaacctgag cagcctgcgt      660
tttaccaaat acaaccaata tgaagacctg atcatgccgc tgattagcta cctgaagaaa     720
cacggtgtta gttccacta tgacaccatc gtggataaca tcattgttaa ccgtaccgag      780
gatgaaaaag tggcgaccga gattaagatg accgagaaag cgaaccgaa ggttatcaaa      840
ctgaccccga cgacctggt gtttgttacc aacggtagca ttaccgaaag caccacctac      900
ggcgataaca cccacccggc ggagcagaag cacgaactgg gtccgagctg gcagctgtgg     960
aaaaacctgg cggcgcaaga cgaggatttc ggccacccgg agaaattttg cgaaaacatt    1020
ccggcggcga ctgggtgat cagcgcgacc gttaccttca ccaacgatga tatcgtgccg      1080
tacattgaaa aggttaacaa gaaagacccg cacagcggta gcattgtgac cagcggcccg     1140
accaccatca agatagcaa ctggctgctg gttatagca ttagccgtca gccgcaattt       1200
cacaagcaaa aaccgaacga actgatcgtg tggctgtacg gtctgtatag caacaccaag    1260
ggcaactacg ttaagaaaac catgccggag tgcgacggta tcgaactgtg cgaggaatgg    1320
ctgtatcaca tgggcgttcc ggagagcgaa atcaagaaaa tggcgattga cgcgaccacc    1380
atcccgaacc acatgccgta cattaccagc tatttcatgc cgcgtgcgct gggtgatcgt    1440
ccgaaagtgg ttccgaagaa cagcaaaaac ctggcgttca tcggcaactt tgcggagacc    1500
gaacgtgata ccgtgtttac caccgagtac agcgttcgta ccgcgatgga agcggtgtat    1560
accctgctga acgttgatcg tggcgtgccg gaagtgtttg cgagcgcgtt tgatgtgcgt    1620
atgctgatga cgcgatgta ctatctgaac gaccgtaaga aactgaccga actggatctg     1680
ccgctgccgg agaagctgat ggttaaagaa ggtctgaaga agtgaaggg cacctacgtt     1740
gaggaactgc tgaagaaata taaactgatc taa                                 1773
```

<210> SEQ ID NO 24
<211> LENGTH: 1773
<212> TYPE: DNA
<213> ORGANISM: Pediococcus claussenii

<400> SEQUENCE: 24

```
atgtactata gcaacggtaa ctacgaggcg ttcgcgcgtc cgaagaaacc ggcgaacgtg      60
gaccagaaaa gcgcgtatct ggttggtagc ggtctggcga gctggcggc ggcgaccttt      120
ctggttcgtg atggtcaaat ggcgggcgac cgtatccacg tgctggagga actgggtctg     180
```

```
ccgggtggca gcatggatgg tatttggaac gagcagaagg gctacatcat tcgtggtggc    240
cgtgagatgg aaccgcactt cgaaaccctg tgggacctgt ttcgtagcat cccgagcctg    300
gagaacgaag atgtgagcgt tctggacgag tactattggc tgaacaaaga agatccgagc    360
ttcagcaagg cgcgtgttat tgaaaaccgt ggtcaacgta tggcgagcga cggcaaactg    420
accctgagcc gtaaggcgat caacgagatc attaaagttg cgctgacccc ggaagaccag    480
ctgcaagata gcagattgac gaggtgttc agccaagaat tctttgatag caacttttgg    540
ctgtactgga gcaccatgtt tgcgtttgaa ccgtgggcga gcgcgctgga aatgcgtcgt    600
tatctgctgc gtttcgtgca ccacattgcg accctgagcg acctgagcag cctgcgtttt    660
accaaataca accagtatga gagcctgatc attccgatgg tgaaattcct ggaaagcaag    720
ggtgttcact ttcaatacaa caccaccgtg ataacatcc tggtgaaccg tgttggtacc    780
ggcaaagttg cgaccaagct ggagatgacc gtggacggca agcacgaaag caagaaactg    840 accgcgacg atctggtgtt cgttaccaac ggtagcatta ccgagagcac cacctatggc    900
gataacaccc atgcggcgcc ggttgagcat gaactgggtg cgacctggca gctgtggaaa    960
aacctggcgg cgcaagaccc ggattttggt caccccggaga agttttacga taacatcccg    1020
gacgcgaact ggaccatcag cggtaccatt accttcaacg acgatcgtgt gaccccgtat    1080
atcgaaaaaa ttagccagaa ggatccgcac agcggtagca tcgtgaccag cggcccggtt    1140
agcattaaag acagcaactg gctgctgggc tacagcatca gccgtcagcc gcactttaaa    1200
gcgcaaaagc cgaacgaact ggtggtttgg gtttatggtc tgttcagcga taagccgggc    1260
aactttgtgg acaagaaaat caccgagtgc accggtattg aactgtgcga ggaatggctg    1320
taccacattg gcgtgccgga ggatcagatc gttgacattg cgaccaacag cgcgagcacc    1380
atcccggcgc acatgccgta cattaccagc tatttcatgc cgcgtgcgct gggtgaccgt    1440
ccgctggttg tgccggaagg tagcgttaac ctggcgttca tcggcaactt tgcggagacc    1500
gaacgtgata ccgtgtttac caccgagtac agcgttcgta ccgcgatgga agcggtgtat    1560
accctgctga cgttgaccg tggtgtgccg gaagtgttcg atagcgcgtt tgacgcgcgt    1620
gttctgatga acgcgatcta ctatctgaac gataagaaaa agctggaaga catccagctg    1680
ccgttcgcgg agaaagcgat tgaaaagcaa gtgctgcgta aaatcaaggg cacctacatt    1740
gaggaactgc tgaaaaacgc gcacctgctg taa                                  1773

<210> SEQ ID NO 25
<211> LENGTH: 1773
<212> TYPE: DNA
<213> ORGANISM: Lactobacillus ruminis

<400> SEQUENCE: 25
atgtactata gcaacggcaa ctacgaagcg ttcgcgcgtc cgaagaaacc ggcgggtgtg     60
gagaacaaga gcgcgtatat tgttggtagc ggtctggcgg cgctgagcac cgcggttttt    120
ctgatccgtg acggtcaaat ggatggcgcg aagattcacc tgctggagga actgagcctg    180
ccgggtggca gcatggatgg tatcaaaaac gaacgtctgg gctacatcat tcgtggtggc    240
cgtgagatgg aaccgcactt cgaggttctg tgggacctgt ttcgtagcat cccgagcctg    300
gagaacccgg aacacagcat tctggatgaa ttctactggc tgaacaaaga ggacccgtgc    360
tttgcgaaaa cccgtgtgat ctatcaccag ggtcaagaaa ttccgacga tggccagctg    420 accctgagca agaaagcgat caaggaaatc attaaactga ttctgacccc ggaggacaag    480
```

```
ctgcaggatg tgcaaatcga ccaggttttc gacgatgagt tctttaaaag caacttttgg      540
ctgtactggc gtaccatgtt cgcgtttgaa ccgtgggcga gcgcgatgga gatgcgtcgt      600
tatctgatgc gtttcgtgca acacgttggc accctgaaga acctgagcag cctgcgtttt      660
accaaataca accagtatga aagcctgatc atgccgattg tggcgtacct gaaagagcac      720
ggtgttaact tccgttatga taccgtggtt accaacatca ttgtgaaccg taccggcagc      780
gacaaggttg cgaagaaaat tgaaatgacc gtggcgggcg aggaaaaagc gctggagctg      840
accgaaaacg acctggtgtt tgttaccaac ggtagcatca ccgaaagcac cacctacggc      900
gacaacgatc atgcggcgcc ggttacccat gagctgggtg cgagctggca actgtgggaa      960
aacctggcgg cgcaggatga ggcgtttggt cacccggaca agttttgcaa acacatcccg     1020
gatgcgaact ggaccgttag cgcgaccatt accttcaagg acagccgtgt ggcgaaatac     1080
atcgaacgtg ttaacaagaa agatccgtat agcggtagca tcgtgagcag cggcccgacc     1140
agcattaagg acagcaactg gagcctgggt tacagcatca gccgtcaacc gcacttcaaa     1200
gcgcagcaac cgaacgagct ggttgtgtgg ctgtacccgc tgtttaccga tcgtatcggt     1260
aactatattg agaagcgtcc ggacgaatgc accggcatgg agctgtgcga ggaatggctg     1320
tatcacatgg gtgtgccgga gaacgaaatc aaagcggatta ccaggatgc gagcaccatc     1380
ccgtgccaca tgccgtacat taccacctat ttcatgccgc gtgcgaacgg tgaccgtccg     1440
ctggttgtgc cgaagcactg caaaaacctg cgttcattg gtaactacgc ggaaaccccg     1500
cgtgataccg tgtttaccac cgaatacagc gttcgtaccg cgatggaggc ggtgtatacc     1560
ctgctgaacg ttgatcgtgg tgtgccggaa gtgttcggca gcgtgtttga cgttcgtatg     1620
atgctgaacg cgttctacta tctgaacgac cagaagagcc tggacgaact ggatctgagc     1680
tggccggaga gaccgcggt taaggttttt atgagcaaga tcaaaggcac ctacattgag     1740
gaactgatga aggagtatca cgtgatcaaa taa                                    1773

<210> SEQ ID NO 26
<211> LENGTH: 1770
<212> TYPE: DNA
<213> ORGANISM: Streptococcus infantarius

<400> SEQUENCE: 26
atgtactata gcaacggcaa ctacgaagcg ttcgcgcgtc cgaagaaacc ggagaacgtg       60
gacgagaaga gcgcgtatat cgttggtagc ggtctggcgg cgctgagcac cgcggtgttt      120
ctggttcgtg acgcgcagat gagcggtgat cacatccaca ttctggagga actgagcctg      180
ccgggtggca gcatggacgg tattaagaac gatcgtctgg gctacatcat cgtggtggc       240
cgtgagatgg aaccgcactt cgaggtgctg tgggacctgt ccgtagcat cccgagcctg      300
gaaaacccgg accacagcat tctggatgag ttctactggc tgaacaaaga agacccgtgc      360
tatgcgaaga cccgtgttat ctgcaaccgt ggtaaagcgc tgccgaacga cggccaactg      420
accctgagcg agaaggcgat caagaaatg atcgatctga ttctgatgcc ggagagcaag      480
ctggaaaacg tgcagattga ccaagttttc gacgatgagt tctttaacag caacttttgg      540
ctgtactggt gcaccatgtt cgcgtttgag ccgtggagca gcgcgatgga aatgcgtcgt      600
tatctgatgc gtttcattca gcacgtgagc tgcctgaaaa acctgagcag cctgcgtttt      660
accaagtaca accaatatga gagcctgatc ctgccgattg tgcactacct gagcgaacac      720
ggcgttgact tcaactatga taccaccgtg accaacatcc tggttaaccg taaaggcaac      780
aagaaagtgg cgagcaagct ggaatttacc aaagcgggtc aggttaagga gctgttcctg      840
```

```
agcgaaaacg atctggtgtt tgttaccaac ggtagcatta ccgagagcac cacctacggc    900
gacaacgatc atccggcgcc ggttaaacat gagctgggtg cgagctggga actgtggcag    960
aagctggcgg cgcaagacga gagcttcggt cacccggaaa agttttgcca aaacatcccg   1020
gacgcgaact ggaccatcag cgcgaccatt accttcaagg ataaacgtat cagcccgtac   1080
attgaagcgg tgaaccacaa agatccgtat agcggtagca tcgttaccag cggcccgacc   1140
agcattaagg acagcaactg gctgctgggt tacagcatca gccgtcagcc gcactttaag   1200
gtgcaaaaag ataacgagct ggttgtgtgg ctgtacagcc tgtataccga ccgtaagggt   1260
aactacattg cgaagcgtcc ggatgaatgc accggcaaag agctgtgcca ggaatggctg   1320
tatcacatgg gtgttccgga gaccgaaatc gcggagattg cggacaccgc gagcaccatc   1380
ccgtgccaca tgccgtacat taccacctat ttcatgccgc gtggcctgaa cgaccgtccg   1440
ctggttgtgc gaaggatag ccaaaacctg gcgttcatcg gtaactacgc ggaaaccccg   1500
cgtgataccg tgtttaccac cgagtacagc gttcgtaccg cgatggaagc ggtgtatacc   1560
ctgctggacg ttgatcgtgg cgtgccggaa gttttcgcga gcgcgtttga cgtgcgtatg   1620
ctgctgaacg cgctgtacta tctgaacgac cagaaaagcc tgaccgagat cgatattccg   1680
tgggcggaga aggcggtgct gaaagaagcg ctgaagaaag ttcacggtac ctacctggag   1740
gaactgctga aggagtatca cctgctgtaa                                    1770

<210> SEQ ID NO 27
<211> LENGTH: 1770
<212> TYPE: DNA
<213> ORGANISM: Streptococcus mutans

<400> SEQUENCE: 27
atgtactata gcaacggcaa ctacgaagcg ttcgcgcaca gccaaaagcc ggagaacgtg     60
gacggtaaaa gcgcgtatat cgttggtagc ggtctggcgg cgctgagcac cgcggtgttt    120
ctgattcgtg acggtcagat ggcgggcgaa cgtatccaca ttctggagga actgagcctg    180
ccgggtggca gcatggatgg tatccgtaac gaacgtctgg gctacatcat tcgtggtggc    240
cgtgagatgg aaccgcactt cgaggttctg tgggacctgt tccgtagcat cccgagcctg    300
gaaaacccga gcacagcat tctggacgag ttctactggc tgaacaagaa agatccgagc    360
tttgcgaaga cccgtgcgat ctatgaacgt ggtaaagcga ttccggacga tggccaactg    420
accctgagcc agaaggcggt gaaagaaatc ttcgacctgg ttctgacccc ggagagccac    480
ctgcaggacg tgcaaattga tcaggttttc agcgaggatt tctttaacag caactttgg    540 ctgtactgga gcaccatgtt cgcgtttgag ccgtgggcga gcgcgatgga aatgcgtcgt    600
tatctgatgc gtttcatcca acacgtgggt accctgaaga acctgagcag cctgaaattt    660
acccaataca accagtatga gagcctgatc ctgccgctgg ttgcgttcct gaaggaccac    720
aacgttaact ttagctacca aaccgtggtt accaacattc tggtgaaccg tagcggcagc    780
gataagctgg cgaccaaaat cgagatgacc gttaacggtc aggagaagag cattgcgctg    840
agccgtgacg atctggtgtt cgttaccaac ggtagcatca ccgaaagcag cacctatggc    900
aacaacaacc atccggcgcc gctgacccat gacctgggtg cgagctggca actgtggaag    960
aacctggcgg cgcaggacag cgatttcggt tgcccggaga atttttgcga aaacattccg   1020
gacgcgaact ggaccatgag cgcgaccatc accttcaccg atcagcgtat tgcgaagtac   1080
atcgagcaaa ttaaccagaa agacccgtat agcggtagca tcgtgaccag cggcccgacc   1140
```

```
agcattaagg atagcagctg gctgctgggt tacagcatca gccgtcaacc gcactttaaa    1200
gagcagaaga aaaacgaact ggtgatttgg ctgtacgcgc tgtataccga ccgtaagggt    1260
gattacgttg cgaaacgtcc ggacgagtgc accggcatcg aaatgtgcga ggaatggctg    1320
tatcacatcg gtgttccgga gaacaccatt cacgaactgg cgtgcagcgc gagcaccatc    1380
ccgtgccaca tgccgtacat taccacctat ttcatgccgc gtaccaccaa cgaccgtccg    1440
ctggttgtgc cgaagcacag caaaaacctg gcgttcatcg gcaactacgc ggaaaccccg    1500
cgtgataccg tgtttaccac cgagtacagc gttcgtaccg cgatggaggc ggtgtatacc    1560
ctgctggaag ttgaccgtgg cgtgccggaa gtgttcgcga gcacctttga tattcgtatg    1620
ctgctgaacg cgctgtacta tctgaacggt cagaaaagcc tgatcgaaat tgactttccg    1680
tgggtggaga aggcggcgct gaaagaagcg ctgaagaaag ttaagggtac ctacatcgag    1740
gaactgctga aagattatca cctgatttaa                                     1770

<210> SEQ ID NO 28
<211> LENGTH: 1770
<212> TYPE: DNA
<213> ORGANISM: Streptococcus equinus

<400> SEQUENCE: 28
atgtactata gcaacggcaa ctacgaggcg ttcgcgcgtc cgaagaaacc ggaaaacgtg      60
gaccagaaaa gcgcgtatat cgttggtagc ggtctggcgg cgctgagcac cgcggtgttt    120
ctggttcgtg acgcgcaaat gccgggtgat cacatccaca ttctggagga actgaaactg    180
ccgggtggca gcatggacgg tattaagaac gatcgtctgg gctacatcat cgtggtggc     240 cgtgagatgg aaccgcactt cgaggtgctg tgggacctgt tccgtagcat cccgagcctg    300
gagaacccgg aaaacagcat tctggacgag ttctactggc tgaacaaaga agatccgtgc    360
tatgcgaaga cccgtgttat ccacgaccgt ggcaaggcga ttccgaacga tggccagctg    420
accctgagcg agaaggcgat caaagaaatc attagcctga ttctgacccc ggagagcaaa    480
ctggcgaacg tgcagatcga ccaagttttc accgatgaat tctttaagag caacttttgg    540
ctgtactggt gcaccatgtt cgcgtttgag ccgtggagca gcgcgatgga aatgcgtcgt    600
tatctgatgc gtttcattca gcacgtgggc tgcctgaaaa acctgagcag cctgcgtttt    660
accaagtaca ccaatatgaa gagcctgatc ctgccgattg tgcactacct gaccgaacac    720
ggtgttgact tcagctataa caccaccgtg accaacatcc tggttaaccg taagggccag    780
gacaaagttg cgaccaagat tgagtttagc aaagatggtc aagcgaagga actgttcctg    840
accccggacg atctggtgtt tgttaccaac ggtagcatca ccgaaagcac cacctacggc    900
gacaacgatc atccggcgcc ggtggagcat gatctgggtg cgagctggga actgtggaag    960
aaactggcgg cgcaggacga tagcttcggt caccggaag tgttctgcca aaacatcccg   1020
gacgcgaact ggaccatcag cgcgaccatt accttcaagg ataaacgtat cgcgccgtac   1080
attgaagcgg tgaaccacaa agaccccgtat agcggtagca tcgttaccag cggcccgacc   1140
agcattaagg atagcaactg gctgctgggt tacagcatca gccgtcagcc gcacttcaag   1200
acccaaaaag acaacgagct ggttgtgtgg ctgtacccgc tgtataccga tcgtaagggt   1260
aactttgtgg acaagcgtcc ggatcagtgc agcggcaaag agctgtgcca agaatggctg   1320
tatcacatgg gtgttccgga agcggacatc aaggagatgg cggaaagcgc gagcaccatc   1380
ccgtgccaca tgccgtacat taccacctat tttatgccgc gtggcctgaa cgaccgtccg   1440
ctggttgtgc cggagcacag caaaaacctg gcgttcattg gtaactacgc ggaaaccccg   1500
```

```
cgtgataccg tgtttaccac cgagtacagc gttcgtaccg cgatggaagc ggtgtatacc    1560
ctgctgaaag ttgatcgtgg cgtgccggaa gtgtttgcga gcgcgtttga tgtgcgtatg    1620
atcctgaacg cgctgtacta tctgaacgac cagaagagcc tgaccgaaat cgatattccg    1680
tggaccgaga aagcggttct gaaggaaagc ctgaagaaaa tccacggtac ctacattgag    1740
gaactgctga aggagtatca cctgctgtaa                                    1770
```

<210> SEQ ID NO 29
<211> LENGTH: 44
<212> TYPE: DNA
<213> ORGANISM: Artificial Sequence
<220> FEATURE:
<223> OTHER INFORMATION: primer

<400> SEQUENCE: 29

```
tgaaaaagga agagttgaag cctgcttttt tatactaagt tggc                      44
```

<210> SEQ ID NO 30
<211> LENGTH: 45
<212> TYPE: DNA
<213> ORGANISM: Artificial Sequence
<220> FEATURE:
<223> OTHER INFORMATION: primer

<400> SEQUENCE: 30

```
aacttggtct gacagcgctc aagttagtat aaaaaagctg aacga                     45
```

<210> SEQ ID NO 31
<211> LENGTH: 28
<212> TYPE: DNA
<213> ORGANISM: Artificial Sequence
<220> FEATURE:
<223> OTHER INFORMATION: primer

<400> SEQUENCE: 31

```
actcttcctt tttcaatatt attgaagc                                        28
```

<210> SEQ ID NO 32
<211> LENGTH: 28
<212> TYPE: DNA
<213> ORGANISM: Artificial Sequence
<220> FEATURE:
<223> OTHER INFORMATION: primer

<400> SEQUENCE: 32

```
ctgtcagacc aagtttactc atatatac                                        28
```

<210> SEQ ID NO 33
<211> LENGTH: 38
<212> TYPE: DNA
<213> ORGANISM: Artificial Sequence
<220> FEATURE:
<223> OTHER INFORMATION: primer

<400> SEQUENCE: 33

```
aagaaggaga tatacatatg cactacagca acggtaac                             38
```

<210> SEQ ID NO 34
<211> LENGTH: 40
<212> TYPE: DNA
<213> ORGANISM: Artificial Sequence
<220> FEATURE:
<223> OTHER INFORMATION: primer

```
<400> SEQUENCE: 34
tgtcgacgga gctcgaattc ttagatcagt ttatatttct                        40

<210> SEQ ID NO 35
<211> LENGTH: 38
<212> TYPE: DNA
<213> ORGANISM: Artificial Sequence
<220> FEATURE:
<223> OTHER INFORMATION: primer

<400> SEQUENCE: 35
aagaaggaga tatacatatg cactacagca acggtaac                          38

<210> SEQ ID NO 36
<211> LENGTH: 40
<212> TYPE: DNA
<213> ORGANISM: Artificial Sequence
<220> FEATURE:
<223> OTHER INFORMATION: primer

<400> SEQUENCE: 36
tgtcgacgga gctcgaattc ttaaatcagt ttatattcct                        40

<210> SEQ ID NO 37
<211> LENGTH: 38
<212> TYPE: DNA
<213> ORGANISM: Artificial Sequence
<220> FEATURE:
<223> OTHER INFORMATION: primer

<400> SEQUENCE: 37
aagaaggaga tatacatatg cactacagca acggtaac                          38

<210> SEQ ID NO 38
<211> LENGTH: 40
<212> TYPE: DNA
<213> ORGANISM: Artificial Sequence
<220> FEATURE:
<223> OTHER INFORMATION: primer

<400> SEQUENCE: 38
tgtcgacgga gctcgaattc ttagatcagt ttatatttct                        40

<210> SEQ ID NO 39
<211> LENGTH: 38
<212> TYPE: DNA
<213> ORGANISM: Artificial Sequence
<220> FEATURE:
<223> OTHER INFORMATION: primer

<400> SEQUENCE: 39
aagaaggaga tatacatatg cactacagca acggtaac                          38

<210> SEQ ID NO 40
<211> LENGTH: 40
<212> TYPE: DNA
<213> ORGANISM: Artificial Sequence
<220> FEATURE:
<223> OTHER INFORMATION: primer

<400> SEQUENCE: 40
tgtcgacgga gctcgaattc ttaaatcagt ttatatttct                        40

<210> SEQ ID NO 41
<211> LENGTH: 38
```

-continued

```
<212> TYPE: DNA
<213> ORGANISM: Artificial Sequence
<220> FEATURE:
<223> OTHER INFORMATION: primer

<400> SEQUENCE: 41
aagaaggaga tatacatatg cactacagca acggtaac                               38

<210> SEQ ID NO 42
<211> LENGTH: 40
<212> TYPE: DNA
<213> ORGANISM: Artificial Sequence
<220> FEATURE:
<223> OTHER INFORMATION: primer

<400> SEQUENCE: 42
tgtcgacgga gctcgaattc ttaaatcagt ttatatttct                             40

<210> SEQ ID NO 43
<211> LENGTH: 38
<212> TYPE: DNA
<213> ORGANISM: Artificial Sequence
<220> FEATURE:
<223> OTHER INFORMATION: primer

<400> SEQUENCE: 43
aagaaggaga tatacatatg ctgggtctga ccaaggaa                               38

<210> SEQ ID NO 44
<211> LENGTH: 40
<212> TYPE: DNA
<213> ORGANISM: Artificial Sequence
<220> FEATURE:
<223> OTHER INFORMATION: primer

<400> SEQUENCE: 44
tgtcgacgga gctcgaattc ttacatcagt ttatactgct                             40

<210> SEQ ID NO 45
<211> LENGTH: 38
<212> TYPE: DNA
<213> ORGANISM: Artificial Sequence
<220> FEATURE:
<223> OTHER INFORMATION: primer

<400> SEQUENCE: 45
aagaaggaga tatacatatg cactacagca acggtaac                               38

<210> SEQ ID NO 46
<211> LENGTH: 40
<212> TYPE: DNA
<213> ORGANISM: Artificial Sequence
<220> FEATURE:
<223> OTHER INFORMATION: primer

<400> SEQUENCE: 46
tgtcgacgga gctcgaattc ttacatcaga cgatattctt                             40

<210> SEQ ID NO 47
<211> LENGTH: 38
<212> TYPE: DNA
<213> ORGANISM: Artificial Sequence
<220> FEATURE:
<223> OTHER INFORMATION: primer

<400> SEQUENCE: 47
```
aagaaggaga tatacatatg cactacagca acggtaac          38

<210> SEQ ID NO 48
<211> LENGTH: 40
<212> TYPE: DNA
<213> ORGANISM: Artificial Sequence
<220> FEATURE:
<223> OTHER INFORMATION: primer

<400> SEQUENCE: 48
tgtcgacgga gctcgaattc ttagatcagt ttatatttct          40

<210> SEQ ID NO 49
<211> LENGTH: 38
<212> TYPE: DNA
<213> ORGANISM: Artificial Sequence
<220> FEATURE:
<223> OTHER INFORMATION: primer

<400> SEQUENCE: 49
aagaaggaga tatacatatg tactatagca acggtaac          38

<210> SEQ ID NO 50
<211> LENGTH: 40
<212> TYPE: DNA
<213> ORGANISM: Artificial Sequence
<220> FEATURE:
<223> OTHER INFORMATION: primer

<400> SEQUENCE: 50
tgtcgacgga gctcgaattc ttacagcagg tgcgcgtttt          40

<210> SEQ ID NO 51
<211> LENGTH: 38
<212> TYPE: DNA
<213> ORGANISM: Artificial Sequence
<220> FEATURE:
<223> OTHER INFORMATION: primer

<400> SEQUENCE: 51
aagaaggaga tatacatatg tactatagca acggcaac          38

<210> SEQ ID NO 52
<211> LENGTH: 40
<212> TYPE: DNA
<213> ORGANISM: Artificial Sequence
<220> FEATURE:
<223> OTHER INFORMATION: primer

<400> SEQUENCE: 52
tgtcgacgga gctcgaattc ttatttgatc acgtgatact          40

<210> SEQ ID NO 53
<211> LENGTH: 38
<212> TYPE: DNA
<213> ORGANISM: Artificial Sequence
<220> FEATURE:
<223> OTHER INFORMATION: primer

<400> SEQUENCE: 53
aagaaggaga tatacatatg tactatagca acggcaac          38

<210> SEQ ID NO 54
<211> LENGTH: 40
<212> TYPE: DNA
<213> ORGANISM: Artificial Sequence

```
<220> FEATURE:
<223> OTHER INFORMATION: primer

<400> SEQUENCE: 54
tgtcgacgga gctcgaattc ttacagcagg tgatactcct                    40

<210> SEQ ID NO 55
<211> LENGTH: 38
<212> TYPE: DNA
<213> ORGANISM: Artificial Sequence
<220> FEATURE:
<223> OTHER INFORMATION: primer

<400> SEQUENCE: 55
aagaaggaga tatacatatg tactatagca acggcaac                      38

<210> SEQ ID NO 56
<211> LENGTH: 40
<212> TYPE: DNA
<213> ORGANISM: Artificial Sequence
<220> FEATURE:
<223> OTHER INFORMATION: primer

<400> SEQUENCE: 56
tgtcgacgga gctcgaattc ttaaatcagg tgataatctt                    40

<210> SEQ ID NO 57
<211> LENGTH: 38
<212> TYPE: DNA
<213> ORGANISM: Artificial Sequence
<220> FEATURE:
<223> OTHER INFORMATION: primer

<400> SEQUENCE: 57
aagaaggaga tatacatatg tactatagca acggcaac                      38

<210> SEQ ID NO 58
<211> LENGTH: 40
<212> TYPE: DNA
<213> ORGANISM: Artificial Sequence
<220> FEATURE:
<223> OTHER INFORMATION: primer

<400> SEQUENCE: 58
tgtcgacgga gctcgaattc ttacagcagg tgatactcct                    40

<210> SEQ ID NO 59
<211> LENGTH: 37
<212> TYPE: DNA
<213> ORGANISM: Artificial Sequence
<220> FEATURE:
<223> OTHER INFORMATION: primer

<400> SEQUENCE: 59
aagaaggaga tatacatatg cactacagca gcggcaa                       37

<210> SEQ ID NO 60
<211> LENGTH: 40
<212> TYPE: DNA
<213> ORGANISM: Artificial Sequence
<220> FEATURE:
<223> OTHER INFORMATION: primer

<400> SEQUENCE: 60
tgtcgacgga gctcgaattc ttaaaccagc ttgtatttct                    40
```

<210> SEQ ID NO 61
<211> LENGTH: 20
<212> TYPE: DNA
<213> ORGANISM: Artificial Sequence
<220> FEATURE:
<223> OTHER INFORMATION: primer

<400> SEQUENCE: 61
taatacgact cactataggg                                               20

<210> SEQ ID NO 62
<211> LENGTH: 19
<212> TYPE: DNA
<213> ORGANISM: Artificial Sequence
<220> FEATURE:
<223> OTHER INFORMATION: primer

<400> SEQUENCE: 62
gctagttatt gctcagcgg                                                19

<210> SEQ ID NO 63
<211> LENGTH: 31
<212> TYPE: DNA
<213> ORGANISM: Artificial Sequence
<220> FEATURE:
<223> OTHER INFORMATION: primer

<400> SEQUENCE: 63
tactctacag cgagtatacc tgtacagact g                                  31

<210> SEQ ID NO 64
<211> LENGTH: 30
<212> TYPE: DNA
<213> ORGANISM: Artificial Sequence
<220> FEATURE:
<223> OTHER INFORMATION: primer

<400> SEQUENCE: 64
tgaccttggt actcaaagaa tattcagatg                                    30

<210> SEQ ID NO 65
<211> LENGTH: 39
<212> TYPE: DNA
<213> ORGANISM: Artificial Sequence
<220> FEATURE:
<223> OTHER INFORMATION: primer

<400> SEQUENCE: 65
cccagtcacg acgtttgatc ccagctttgt ttctagctc                          39

<210> SEQ ID NO 66
<211> LENGTH: 33
<212> TYPE: DNA
<213> ORGANISM: Artificial Sequence
<220> FEATURE:
<223> OTHER INFORMATION: primer

<400> SEQUENCE: 66
tgagtaccaa ggtcaattgt cttgttttca cac                                33

<210> SEQ ID NO 67
<211> LENGTH: 33
<212> TYPE: DNA
<213> ORGANISM: Artificial Sequence
<220> FEATURE:
<223> OTHER INFORMATION: primer

```
<400> SEQUENCE: 67
tactcgctgt agagtagaat gtaattacta atg                                    33

<210> SEQ ID NO 68
<211> LENGTH: 38
<212> TYPE: DNA
<213> ORGANISM: Artificial Sequence
<220> FEATURE:
<223> OTHER INFORMATION: primer

<400> SEQUENCE: 68
ggaaacagct atgactgctc ctggaccaga gccttgag                               38

<210> SEQ ID NO 69
<211> LENGTH: 20
<212> TYPE: DNA
<213> ORGANISM: Artificial Sequence
<220> FEATURE:
<223> OTHER INFORMATION: primer

<400> SEQUENCE: 69
gtcatagctg tttcctgtgt                                                   20

<210> SEQ ID NO 70
<211> LENGTH: 20
<212> TYPE: DNA
<213> ORGANISM: Artificial Sequence
<220> FEATURE:
<223> OTHER INFORMATION: primer

<400> SEQUENCE: 70
aacgtcgtga ctgggaaaac                                                   20

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71
gttttcccag tcacgacgtt                                                   20

<210> SEQ ID NO 72
<211> LENGTH: 20
<212> TYPE: DNA
<213> ORGANISM: Artificial Sequence
<220> FEATURE:
<223> OTHER INFORMATION: primer

<400> SEQUENCE: 72
acacaggaaa cagctatgac                                                   20

<210> SEQ ID NO 73
<211> LENGTH: 24
<212> TYPE: DNA
<213> ORGANISM: Artificial Sequence
<220> FEATURE:
<223> OTHER INFORMATION: primer

<400> SEQUENCE: 73
tgatcccagc tttgttttcta gctc                                             24

<210> SEQ ID NO 74
```

<211> LENGTH: 23
<212> TYPE: DNA
<213> ORGANISM: Artificial Sequence
<220> FEATURE:
<223> OTHER INFORMATION: primer

<400> SEQUENCE: 74
tgctcctgga ccagagcctt gag            23

<210> SEQ ID NO 75
<211> LENGTH: 24
<212> TYPE: DNA
<213> ORGANISM: Artificial Sequence
<220> FEATURE:
<223> OTHER INFORMATION: primer

<400> SEQUENCE: 75
acactgctca ctatcgcagg ctgc           24

<210> SEQ ID NO 76
<211> LENGTH: 23
<212> TYPE: DNA
<213> ORGANISM: Artificial Sequence
<220> FEATURE:
<223> OTHER INFORMATION: primer

<400> SEQUENCE: 76
agcttcaaaa cacacagcag tcc            23

<210> SEQ ID NO 77
<211> LENGTH: 2103
<212> TYPE: DNA
<213> ORGANISM: Yarrowia lipoytica

<400> SEQUENCE: 77
atgatctccc ccaacctcac agctaacgtc gagattgacg gcaagcagta caacaccttc     60
acagagccac ccaaggcgct cgccggcgag cgagccaagg tcaagttccc catcaaggac    120
atgacggagt ttctgcacgg tggcgaggag aacgtgacca tgatcgagcg actgatgacg    180
gagctcgagc gagaccccgt gctcaacgtg tcgggcgact acgacatgcc caaggagcag    240
ctgcgagaga cggccgtggc gcgaattgcg gcgctgtccg gccactggaa gaaggacaca    300
gaaaaggagg cgctgctgcg gtcccagctg cacggcattg tggacatggg cacccgaatc    360
cgactcggtg tgcacacggg cctgttcatg ggcgccatcc ggggttccgg caccaaggag    420
cagtacgact actgggtgcg aaagggcgcc gcggacgtca agggcttcta cggctgcttt    480
gctatgaccg agctgggcca tggctccaac gtggccggtc ttgagaccac cgccacctac    540
atccaggaca cggacgagtt catcatcaac acccccaaca ctggagccac caagtggtgg    600
attggaggag ccgcccactc ggccacccac accgcctgct tgctcgtct gcttgtcgac    660
ggcaaggact acggcgtcaa gatctttgtt gtccagctgc gagacgtctc ttctcactct    720
ctcatgcccg gcatcgctct cggcgacatt ggaaagaaga tgggccgaga cgccatcgac    780
aacggctgga tccagttcac caatgtgcga atcccccgac agaacatgct catgaagtac    840
gccaaggtct cgtctaccgg caaggtgtcg cagcctcctc tggcccagct cacctacggc    900
gctctcattg gcggccgagt caccatgatt gccgactcct ctttgtctc ccagcgattc    960
atcaccattg ctctgcgata cgcctgtgtg cgacgacagt ttggcaccac ccccggccag   1020
cccgagacta agatcatcga ctaccccac catcagcgac gtctgctgcc tcttctggcc   1080
ttcacctacg ccatgaagat ggccgccgac cagtcccaga ttcagtacga tcagaccacc   1140

-continued

```
gatctgctgc agaccatcga ccctaaggac aagggcgctc tgggcaaggc cattgtcgac    1200
ctcaaggagc tgtttgcctc ttctgctggt ctcaaggcct tcaccacctg gacctgtgcc    1260
aacatcattg accagtgccg acaggcctgc ggtggccacg gctactctgg ctacaacggc    1320
tttggccagg cctacgccga ctgggttgtc cagtgcacct gggagggtga caacaacgtc    1380
ctgtgtctgt ccatgggccg aggtctcatc cagtcgtgtc tgggccaccg aaagggtaag    1440
cctctgggct cttctgtcgg ctacctggct aacaagggtc ttgagcaggc tactctgagc    1500
ggccgagacc tcaaggaccc caaggttctc atcgaggcct gggagaaggt cgccaacggc    1560
gccatccagc gggccactga caaatttgtc gagctcacca agggcggcct ctctcctgac    1620
caggcctttg aggagctgtc gcagcagcga ttccagtgtg ccaagatcca cacccgaaag    1680
cacctggtga ctgccttcta cgagcgaatc aacgcctctg cgaaggccga cgtcaagcct    1740
tacctcatca acctcgccaa cctcttcact ctgtggtcca ttgaggagga ctctggtctc    1800
ttcctgcgag agggtttcct gcagcccaag gacattgacc aggtgactga gctggtgaac    1860
cactactgca aggaggttcg agaccaggtt gccggctaca ccgatgcctt tggtctgtct    1920
gactggttca tcaacgctcc cattggaaac tacgatggtg acgtttacaa gcattacttt    1980
gccaaggtta accagcagaa ccctgctcag aaccccgac ctccttacta tgagagcact    2040
cttcgacctt tcctgttccg agaggatgag gatgacgaca tttgcgagct ggacgaggaa    2100
tag                                                                 2103
```

<210> SEQ ID NO 78
<211> LENGTH: 700
<212> TYPE: PRT
<213> ORGANISM: Yarrowia lipoytica

<400> SEQUENCE: 78

```
Met Ile Ser Pro Asn Leu Thr Ala Asn Val Glu Ile Asp Gly Lys Gln
1               5                   10                  15

Tyr Asn Thr Phe Thr Glu Pro Pro Lys Ala Leu Ala Gly Glu Arg Ala
            20                  25                  30

Lys Val Lys Phe Pro Ile Lys Asp Met Thr Glu Phe Leu His Gly Gly
        35                  40                  45

Glu Glu Asn Val Thr Met Ile Glu Arg Leu Met Thr Glu Leu Glu Arg
    50                  55                  60

Asp Pro Val Leu Asn Val Ser Gly Asp Tyr Asp Met Pro Lys Glu Gln
65                  70                  75                  80

Leu Arg Glu Thr Ala Val Ala Arg Ile Ala Ala Leu Ser Gly His Trp
                85                  90                  95

Lys Lys Asp Thr Glu Lys Glu Ala Leu Leu Arg Ser Gln Leu His Gly
            100                 105                 110

Ile Val Asp Met Gly Thr Arg Ile Arg Leu Gly Val His Thr Gly Leu
        115                 120                 125

Phe Met Gly Ala Ile Arg Gly Ser Gly Thr Lys Glu Gln Tyr Asp Tyr
    130                 135                 140

Trp Val Arg Lys Gly Ala Ala Asp Val Lys Gly Phe Tyr Gly Cys Phe
145                 150                 155                 160

Ala Met Thr Glu Leu Gly His Gly Ser Asn Val Ala Gly Leu Glu Thr
                165                 170                 175

Thr Ala Thr Tyr Ile Gln Asp Thr Asp Glu Phe Ile Ile Asn Thr Pro
            180                 185                 190
```

-continued

Asn Thr Gly Ala Thr Lys Trp Trp Ile Gly Ala Ala His Ser Ala
            195                 200                 205

Thr His Thr Ala Cys Phe Ala Arg Leu Leu Val Asp Gly Lys Asp Tyr
210                 215                 220

Gly Val Lys Ile Phe Val Val Gln Leu Arg Asp Val Ser Ser His Ser
225                 230                 235                 240

Leu Met Pro Gly Ile Ala Leu Gly Asp Ile Gly Lys Lys Met Gly Arg
                245                 250                 255

Asp Ala Ile Asp Asn Gly Trp Ile Gln Phe Thr Asn Val Arg Ile Pro
            260                 265                 270

Arg Gln Asn Met Leu Met Lys Tyr Ala Lys Val Ser Ser Thr Gly Lys
        275                 280                 285

Val Ser Gln Pro Pro Leu Ala Gln Leu Thr Tyr Gly Ala Leu Ile Gly
    290                 295                 300

Gly Arg Val Thr Met Ile Ala Asp Ser Phe Phe Val Ser Gln Arg Phe
305                 310                 315                 320

Ile Thr Ile Ala Leu Arg Tyr Ala Cys Val Arg Arg Gln Phe Gly Thr
                325                 330                 335

Thr Pro Gly Gln Pro Glu Thr Lys Ile Ile Asp Tyr Pro Tyr His Gln
            340                 345                 350

Arg Arg Leu Leu Pro Leu Leu Ala Phe Thr Tyr Ala Met Lys Met Ala
        355                 360                 365

Ala Asp Gln Ser Gln Ile Gln Tyr Asp Gln Thr Thr Asp Leu Leu Gln
    370                 375                 380

Thr Ile Asp Pro Lys Asp Lys Gly Ala Leu Gly Lys Ala Ile Val Asp
385                 390                 395                 400

Leu Lys Glu Leu Phe Ala Ser Ser Ala Gly Leu Lys Ala Phe Thr Thr
                405                 410                 415

Trp Thr Cys Ala Asn Ile Ile Asp Gln Cys Arg Gln Ala Cys Gly Gly
            420                 425                 430

His Gly Tyr Ser Gly Tyr Asn Gly Phe Gly Gln Ala Tyr Ala Asp Trp
        435                 440                 445

Val Val Gln Cys Thr Trp Glu Gly Asp Asn Asn Val Leu Cys Leu Ser
    450                 455                 460

Met Gly Arg Gly Leu Ile Gln Ser Cys Leu Gly His Arg Lys Gly Lys
465                 470                 475                 480

Pro Leu Gly Ser Ser Val Gly Tyr Leu Ala Asn Lys Gly Leu Glu Gln
                485                 490                 495

Ala Thr Leu Ser Gly Arg Asp Leu Lys Asp Pro Lys Val Leu Ile Glu
            500                 505                 510

Ala Trp Glu Lys Val Ala Asn Gly Ala Ile Gln Arg Ala Thr Asp Lys
        515                 520                 525

Phe Val Glu Leu Thr Lys Gly Gly Leu Ser Pro Asp Gln Ala Phe Glu
    530                 535                 540

Glu Leu Ser Gln Gln Arg Phe Gln Cys Ala Lys Ile His Thr Arg Lys
545                 550                 555                 560

His Leu Val Thr Ala Phe Tyr Glu Arg Ile Asn Ala Ser Ala Lys Ala
                565                 570                 575

Asp Val Lys Pro Tyr Leu Ile Asn Leu Ala Asn Leu Phe Thr Leu Trp
            580                 585                 590

Ser Ile Glu Glu Asp Ser Gly Leu Phe Leu Arg Glu Gly Phe Leu Gln
        595                 600                 605

Pro Lys Asp Ile Asp Gln Val Thr Glu Leu Val Asn His Tyr Cys Lys

```
                610               615               620
Glu Val Arg Asp Gln Val Ala Gly Tyr Thr Asp Ala Phe Gly Leu Ser
625                 630                 635                 640

Asp Trp Phe Ile Asn Ala Pro Ile Gly Asn Tyr Asp Gly Asp Val Tyr
                645                 650                 655

Lys His Tyr Phe Ala Lys Val Asn Gln Gln Asn Pro Ala Gln Asn Pro
                660                 665                 670

Arg Pro Pro Tyr Tyr Glu Ser Thr Leu Arg Pro Phe Leu Phe Arg Glu
            675                 680                 685

Asp Glu Asp Asp Asp Ile Cys Glu Leu Asp Glu Glu
            690                 695                 700

<210> SEQ ID NO 79
<211> LENGTH: 5552
<212> TYPE: DNA
<213> ORGANISM: Artificial Sequence
<220> FEATURE:
<223> OTHER INFORMATION: plasmid

<400> SEQUENCE: 79
```

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcggggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagttagtg | ttttttgttgg | ttttttatttg | 420 |
| atttgttggt | ttaatatttta | ttttattttta | atatttttattt | tattttatttt | caattaatta | 480 |
| ttttatttat | ttgcttaaat | caaatatttt | ggaccaataa | aaaccgacac | agttttcaga | 540 |
| catgtttgta | gctcatatgt | atcaggtgtg | gttgtggggt | atcaaagccg | aggttggcaa | 600 |
| attttactgg | ggccttcaga | acggtaaaaa | tagaccaatc | agaattctga | aaagcacatc | 660 |
| ttgatctcct | cattgcgggg | agtccaacgg | tggtcttatt | cccccgaatt | tcccgctcaa | 720 |
| tatcgttcca | gaccgacccg | gacacagtgc | ttaacgccgt | tccgaaactc | taccgcagat | 780 |
| atgctccaac | ggactgggct | gcatagatgt | gatcctcggc | ttggagaaat | ggataaaagc | 840 |
| cggccaaaaa | aaagcggaa | aaaagcggaa | aaaagagaa | aaaaaatcgc | aaaatcggaa | 900 |
| aaataggggg | aaaagacgca | aaaacgcaag | gaggggggag | tatatgacac | tgataagcaa | 960 |
| gctcacaacg | gttcctctta | ttttttttcct | catcttctgc | ctaggttccc | aaaatcccag | 1020 |
| atgcttctct | ccagtgccaa | aagtaagtac | cccacaggtt | ttcggccgaa | aattccacgt | 1080 |
| gcagcaacgt | cgtgtggggt | gttaaaatgt | gggggggga | ccaggacaag | aggctcttgt | 1140 |
| gggagccgaa | tgagagcaca | aagcgggcgg | gtgtgataag | gcattttttg | cccattttcc | 1200 |
| cttctcctgt | ctctccgacg | gtgatggcgt | tgtgcgtcct | ctatttctttt | ttattttcttt | 1260 |
| ttgtttttatt | tctctgacta | ccgatttggt | ttgatttcct | caaccccaca | caaataagct | 1320 |
| cgggccgagg | aatatatata | tacacggaca | cagtcgccct | gtggcaacaa | cgtcactacc | 1380 |
| tctacgatac | acacaataac | ttcgtataat | gtatgctata | cgaagttata | tgccctccta | 1440 |
| cgaagctcga | gctaacgtcc | acaagtccgc | ctttgccgct | cgagtgctca | agctcgtggc | 1500 |
| agccaagaaa | accaacctgt | gtgcttctct | ggatgttacc | accaccaagg | agctcattga | 1560 |

```
gcttgccgat aaggtcggac cttatgtgtg catgatcaaa acccatatcg acatcattga    1620
cgacttcacc tacgccggca ctgtgctccc cctcaaggaa cttgctctta agcacggttt    1680
cttcctgttc gaggacagaa agttcgcaga tattggcaac actgtcaagc accagtaccg    1740
gtgtcaccga atcgccgagt ggtccgatat caccaacgcc cacggtgtac ccggaaccgg    1800
aatcattgct ggcctgcgag ctggtgccga ggaaactgtc tctgaacaga agaaggagga    1860
cgtctctgac tacgagaact cccagtacaa ggagttccta gtcccctctc caacgagaa    1920 gctggccaga ggtctgctca tgctggccga gctgtcttgc aagggctctc tggccactgg    1980
cgagtactcc aagcagacca ttgagcttgc ccgatccgac cccgagtttg tggttggctt    2040
cattgcccag aaccgaccta agggcgactc tgaggactgg cttattctga ccccggggt    2100 gggtcttgac gacaagggag acgctctcgg acagcagtac cgaactgttg aggatgtcat    2160
gtctaccgga acggatatca taattgtcgg ccgaggtctg tacggccaga accgagatcc    2220
tattgaggag gccaagcgat accagaaggc tggctgggag gcttaccaga gattaactg    2280 ttagataact tcgtataatg tatgctatac gaagttatat ggagcgtgtg ttctgagtcg    2340
atgttttcta tggagttgtg agtgttagta gacatgatgg gtttatatat gatgaatgaa    2400
tagatgtgat tttgatttgc acgatggaat tgagaacttt gtaaacgtac atgggaatgt    2460
atgaatgtgg gggttttgtg actggataac tgacggtcag tggacgccgt tgttcaaata    2520
tccaagagat gcgagaaact ttgggtcaag tgaacatgtc ctctctgttc aagtaaacca    2580
tcaactatgg gtagtatatt tagtaaggac aggagttgag agaggaaagt tgccattctt    2640
tggagtccca gaaacgtatt ttcgcgttcc aagatcaaat tagtagagta atacgggcac    2700
gggaatccat tcatagtctc aattttccca taggtgtgct acaaggtgtt gagatgtggt    2760
acagtaccac catgattcga gataaagagc ccagaagtca ttgatgaggt caagaaatac    2820
acagatctac agctcaatac aatgaatatc ttctttcata ttcttcaggt gacaccaagg    2880
gtgtctattt tccccagaaa tgcgtgaaaa ggcgcgtgtg tagcgtggag tatgggttcg    2940
gttggcgtat ccttcatata tcgacgaaat agtagggcaa gagatgacaa aaagtatcta    3000
tatgtagaca cgctagaata tggatttgat tggtataaat tcatttattg cgtgtctcac    3060
aaatactctc gataagttgg ggttaaactg gagatggaac aatgtcgata tctcgacata    3120
ttttgatatt tgtactgttg atagtgataa aaagtagacc gttcgaatct cgacaaggag    3180
aagagtccaa tgaaataggt tccatcatca ttcgtcatag ttaaacgccg ctggttgcca    3240
ttactatccg tcttgactac aaccccaact cagcctagac cacagcgaag agaatcagtt    3300
tggagaccga aaatgagcgg cgtaatcatg gtcatagctg tttcctgtgt gaaattgtta    3360
tccgctcaca attccacaca acatacgagc cggaagcata aagtgtaaag cctggggtgc    3420
ctaatgagtg agctaactca cattaattgc gttgcgctca ctgcccgctt ccagtcggg    3480 aaacctgtcg tgccagctgc attaatgaat cggccaacgc gcgggagag gcggtttgcg    3540 tattgggcgc tcttccgctt cctcgctcac tgactcgctg cgctcggtcg ttcggctgcg    3600
gcgagcggta tcagctcact caaaggcggt aatacggtta ccacagaat caggggataa    3660 cgcaggaaag aacatgtgag caaaaggcca gcaaaggcc aggaaccgta aaaaggccgc    3720
gttgctggcg tttttccata ggctccgccc cctgacgag catcacaaaa atcgacgctc    3780
aagtcagagg tggcgaaacc cgacaggact ataaagatac caggcgtttc ccctggaag    3840 ctccctcgtg cgctctcctg ttccgaccct gccgcttacc ggatacctgt ccgcctttct    3900
cccttcggga agcgtggcgc tttctcatag ctcacgctgt aggtatctca gttcggtgta    3960
```

-continued

```
ggtcgttcgc tccaagctgg gctgtgtgca cgaaccccc gttcagcccg accgctgcgc        4020
cttatccggt aactatcgtc ttgagtccaa cccggtaaga cacgacttat cgccactggc        4080
agcagccact ggtaacagga ttagcagagc gaggtatgta ggcggtgcta cagagttctt        4140
gaagtggtgg cctaactacg gctacactag aagaacagta tttggtatct gcgctctgct        4200
gaagccagtt accttcggaa aaagagttgg tagctcttga tccggcaaac aaaccaccgc        4260
tggtagcggt ggtttttttg tttgcaagca gcagattacg cgcagaaaaa aaggatctca        4320
agaagatcct ttgatctttt ctacggggtc tgacgctcag tggaacgaaa actcacgtta        4380
agggattttg gtcatgagat tatcaaaaag gatcttcacc tagatccttt taaattaaaa        4440
atgaagtttt aaatcaatct aaagtatata tgagtaaact tggtctgaca gttaccaatg        4500
cttaatcagt gaggcaccta tctcagcgat ctgtctattt cgttcatcca tagttgcctg        4560
actccccgtc gtgtagataa ctacgatacg ggagggctta ccatctggcc ccagtgctgc        4620
aatgataccg cgagacccac gctcaccggc tccagattta tcagcaataa accagccagc        4680
cggaagggcc gagcgcagaa gtggtcctgc aactttatcc gcctccatcc agtctattaa        4740
ttgttgccgg gaagctagag taagtagttc gccagttaat agtttgcgca acgttgttgc        4800
cattgctaca ggcatcgtgg tgtcacgctc gtcgtttggt atggcttcat tcagctccgg        4860
ttcccaacga tcaaggcgag ttacatgatc ccccatgttg tgcaaaaaag cggttagctc        4920
cttcggtcct ccgatcgttg tcagaagtaa gttggccgca gtgttatcac tcatggttat        4980
ggcagcactg cataattctc ttactgtcat gccatccgta agatgctttt ctgtgactgg        5040
tgagtactca accaagtcat tctgagaata gtgtatgcgg cgaccgagtt gctcttgccc        5100
ggcgtcaata cgggataata ccgcgccaca tagcagaact ttaaaagtgc tcatcattgg        5160
aaaacgttct cggggcgaaa actctcaag gatcttaccg ctgttgagat ccagttcgat        5220
gtaacccact cgtgcaccca actgatcttc agcatctttt actttcacca gcgtttctgg        5280
gtgagcaaaa acaggaaggc aaaatgccgc aaaaaaggga ataagggcga cacggaaatg        5340
ttgaatactc atactcttcc tttttcaata ttattgaagc atttatcagg gttattgtct        5400
catgagcgga tacatatttg aatgtattta gaaaaataaa caaataggg ttccgcgcac        5460 atttccccga aaagtgccac ctgacgtcta agaaaccatt attatcatga cattaaccta        5520
taaaaatagg cgtatcacga ggccctttcg tc                                      5552
```

<210> SEQ ID NO 80
<211> LENGTH: 4400
<212> TYPE: DNA
<213> ORGANISM: Artificial Sequence
<220> FEATURE:
<223> OTHER INFORMATION: plasmid

<400> SEQUENCE: 80

```
tcgcgcgttt cggtgatgac ggtgaaaacc tctgacacat gcagctcccg gagacggtca         60
cagcttgtct gtaagcggat gccgggagca gacaagcccg tcagggcgcg tcagcgggtg        120
ttggcgggtg tcggggctgg cttaactatg cggcatcaga gcagattgta ctgagagtgc        180
accatatgcg gtgtgaaata ccgcacagat gcgtaaggag aaaataccgc atcaggcgcc        240
attcgccatt caggctgcgc aactgttggg aagggcgatc ggtgcgggcc tcttcgctat        300
tacgccagct ggcgaaaggg ggatgtgctg caaggcgatt aagttgggta acgccagggt        360
tttcccagtc acgacgttgt aaaacgacgg ccagtgaatt cgagctcggt acctcgcgaa        420
```

```
tgcatctaat aacttcgtat aatgtatgct atacgaagtt ataccctcct tgacagtctt    480
gacgtgcgca gctcaggggc atgatgtgac tgtcgcccgt acatttagcc catacatccc    540
catgtataat catttgcatc catacatttt gatggccgca cggcgcgaag caaaaattac    600
ggctcctcgc tgcagacctg cgagcaggga acgctcccc tcacagacgc gttgaattgt     660
ccccacgccg cgcccctgta gagaaatata aaaggttagg atttgccact gaggttcttc    720
tttcatatac ttccttttaa aatcttgcta ggatacagtt ctcacatcac atccgaacat    780
aaacaaccat gggtaaaaag cctgaactca ccgcgacgtc tgtcgagaag tttctgatcg    840
aaaagttcga cagcgtctcc gacctgatgc agctctcgga gggcgaagaa tctcgtgctt    900
tcagcttcga tgtaggaggg cgtggatatg tcctgcgggt aaatagctgc gccgatggtt    960
tctacaaaga tcgttatgtt tatcggcact ttgcatcggc cgcgctcccg attccggaag   1020
tgcttgacat tggggaattc agcgagagcc tgacctattg catctcccgc cgtgcacagg   1080
gtgtcacgtt gcaagacctg cctgaaaccg aactgcccgc tgttctgcag ccggtcgcgg   1140
aggccatgga tgcgatcgct gcggccgatc ttagccagac gagcgggttc ggcccattcg   1200
gaccgcaagg aatcggtcaa tacactacat ggcgtgattt catatgcgcg attgctgatc   1260
cccatgtgta tcactggcaa actgtgatgg acgacaccgt cagtgcgtcc gtcgcgcagg   1320
ctctcgatga gctgatgctt tgggccgagg actgccccga agtccggcac tcgtgcacg    1380 cggatttcgg ctccaacaat gtcctgacgg acaatggccg cataacagcg gtcattgact   1440
ggagcgaggc gatgttcggg gattcccaat acgaggtcgc caacatcttc ttctggaggc   1500
cgtggttggc ttgtatggag cagcagacgc gctacttcga gcggaggcat ccggagcttg   1560
caggatcgcc gcggctccgg gcgtatatgc tccgcattgg tcttgaccaa ctctatcaga   1620
gcttggttga cggcaatttc gatgatgcag cttgggcgca gggtcgatgc gacgcaatcg   1680
tccgatccgg agccgggact gtcgggcgta cacaaatcgc ccgcagaagc gcggccgtct   1740
ggaccgatgg ctgtgtagaa gtactcgccg atagtggaaa ccgacgcccc agcactcgtc   1800
cgagggcaaa ggaataatca gtactgacaa taaaaagatt cttgttttca agaacttgtc   1860
atttgtatag ttttttttata ttgtagttgt tctattttaa tcaaatgtta gcgtgattta   1920
tatttttttt cgcctcgaca tcatctgccc agatgcgaag ttaagtgcgc agaaagtaat   1980
atcatgcgtc aatcgtatgt gaatgctggt cgctatactg ctgtcgattc gatactaacg   2040
ccgccatcca gtttaaacga ggggtaccga gatatcctgc agcggccgcg ataacttcgt   2100
ataatgtatg ctatacgaag ttatggatcc cgggcccgtc gactgcagag gcctgcatgc   2160
aagcttggcg taatcatggt catagctgtt tcctgtgtga aattgttatc cgctcacaat   2220
tccacacaac atacgagccg gaagcataaa gtgtaaagcc tggggtgcct aatgagtgag   2280
ctaactcaca ttaattgcgt tgcgctcact gcccgctttc cagtcgggaa acctgtcgtg   2340
ccagctgcat taatgaatcg gccaacgcgc ggggagaggc ggtttgcgta ttgggcgctc   2400
ttccgcttcc tcgctcactg actcgctgcg ctcggtcgtt cggctgcggc gagcggtatc   2460
agctcactca aaggcggtaa tacggttatc cacagaatca ggggataacg caggaaagaa   2520
catgtgagca aaaggccagc aaaaggccag gaaccgtaaa aaggccgcgt tgctggcgtt   2580
tttccatagg ctccgccccc ctgacgagca tcacaaaaat cgacgctcaa gtcagaggtg   2640
gcgaaacccg acaggactat aaagatacca ggcgtttccc cctggaagct ccctcgtgcg   2700
ctctcctgtt ccgaccctgc cgcttaccgg atacctgtcc gcctttctcc cttcgggaag   2760
cgtggcgctt tctcatagct cacgctgtag gtatctcagt tcggtgtagg tcgttcgctc   2820
```

-continued

```
caagctgggc tgtgtgcacg aaccccccgt tcagcccgac cgctgcgcct tatccggtaa    2880
ctatcgtctt gagtccaacc cggtaagaca cgacttatcg ccactggcag cagccactgg    2940
taacaggatt agcagagcga ggtatgtagg cggtgctaca gagttcttga agtggtggcc    3000
taactacggc tacactagaa gaacagtatt tggtatctgc gctctgctga agccagttac    3060
cttcggaaaa agagttggta gctcttgatc cggcaaacaa accaccgctg gtagcggtgg    3120
tttttttgtt tgcaagcagc agattacgcg cagaaaaaaa ggatctcaag aagatccttt    3180
gatcttttct acggggtctg acgctcagtg aacgaaaac  tcacgttaag ggattttggt    3240
catgagatta tcaaaaagga tcttcaccta gatccttta  aattaaaaat gaagttttaa    3300
atcaatctaa agtatatatg agtaaacttg gtctgacagt taccaatgct taatcagtga    3360
ggcacctatc tcagcgatct gtctatttcg ttcatccata gttgcctgac tccccgtcgt    3420
gtagataact acgatacggg agggcttacc atctggcccc agtgctgcaa tgataccgcg    3480
agacccacgc tcaccggctc cagatttatc agcaataaac cagccagccg gaagggccga    3540
gcgcagaagt ggtcctgcaa ctttatccgc ctccatccag tctattaatt gttgccggga    3600
agctagagta agtagttcgc cagttaatag tttgcgcaac gttgttgcca ttgctacagg    3660
catcgtggtg tcacgctcgt cgtttggtat ggcttcattc agctccggtt cccaacgatc    3720
aaggcgagtt acatgatccc ccatgttgtg caaaaaagcg gttagctcct tcggtcctcc    3780
gatcgttgtc agaagtaagt tggccgcagt gttatcactc atggttatgg cagcactgca    3840
taattctctt actgtcatgc catccgtaag atgcttttct gtgactggtg agtactcaac    3900
caagtcattc tgagaatagt gtatgcggcg accgagttgc tcttgcccgg cgtcaatacg    3960
ggataatacc gcgccacata gcagaacttt aaaagtgctc atcattggaa acgttcttc    4020 ggggcgaaaa ctctcaagga tcttaccgct gttgagatcc agttcgatgt aacccactcg    4080
tgcacccaac tgatcttcag catcttttac tttcaccagc gtttctgggt gagcaaaaac    4140
aggaaggcaa aatgccgcaa aaaagggaat aagggcgaca cggaaatgtt gaatactcat    4200
actcttcctt tttcaatatt attgaagcat ttatcagggt tattgtctca tgagcggata    4260
catatttgaa tgtatttaga aaaataaaca aataggggtt ccgcgcacat ttccccgaaa    4320
agtgccacct gacgtctaag aaaccattat tatcatgaca ttaacctata aaaataggcg    4380
tatcacgagg ccctttcgtc                                                4400
```

<210> SEQ ID NO 81
<211> LENGTH: 39
<212> TYPE: DNA
<213> ORGANISM: Artificial Sequence
<220> FEATURE:
<223> OTHER INFORMATION: primer

<400> SEQUENCE: 81
gctatacgaa gttataccct ccttgacagt cttgacgtg                             39

<210> SEQ ID NO 82
<211> LENGTH: 35
<212> TYPE: DNA
<213> ORGANISM: Artificial Sequence
<220> FEATURE:
<223> OTHER INFORMATION: primer

<400> SEQUENCE: 82
attatacgaa gttatcgcgg ccgctgcagg atatc                                 35

<210> SEQ ID NO 83
<211> LENGTH: 29
<212> TYPE: DNA
<213> ORGANISM: Artificial Sequence
<220> FEATURE:
<223> OTHER INFORMATION: primer

<400> SEQUENCE: 83
gggaggctta ccagaagatt aactgttag                               29

<210> SEQ ID NO 84
<211> LENGTH: 25
<212> TYPE: DNA
<213> ORGANISM: Artificial Sequence
<220> FEATURE:
<223> OTHER INFORMATION: primer

<400> SEQUENCE: 84
cgagcttcgt aggagggcat ataac                                   25

<210> SEQ ID NO 85
<211> LENGTH: 23
<212> TYPE: DNA
<213> ORGANISM: Artificial Sequence
<220> FEATURE:
<223> OTHER INFORMATION: primer

<400> SEQUENCE: 85
cctcttcgct attacgccag ctg                                     23

<210> SEQ ID NO 86
<211> LENGTH: 26
<212> TYPE: DNA
<213> ORGANISM: Artificial Sequence
<220> FEATURE:
<223> OTHER INFORMATION: primer

<400> SEQUENCE: 86
cccaggcttt acactttatg cttccg                                  26

<210> SEQ ID NO 87
<211> LENGTH: 6325
<212> TYPE: DNA
<213> ORGANISM: Artificial Sequence
<220> FEATURE:
<223> OTHER INFORMATION: plasmid

<400> SEQUENCE: 87
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtagtcg ttttttgttgg ttttatttg     420 atttgttggt ttaatattta ttttatttta atatttattt tatttatttt caattaatta     480 tttatttat tgcttaaat caaatatttt ggaccaataa aaccgacac agttttcaga     540 catgtttgta gctcatatgt atcaggtgtg gttgtgggt atcaaagccg aggttggcaa     600 atttactgg ggccttcaga acggtaaaaa tagaccaatc agaattctga aaagcacatc     660

```
ttgatctcct cattgcgggg agtccaacgg tggtcttatt cccccgaatt tcccgctcaa      720
tatcgttcca gaccgacccg gacacagtgc ttaacgccgt tccgaaactc taccgcagat      780
atgctccaac ggactgggct gcatagatgt gatcctcggc ttggagaaat ggataaaagc      840
cggccaaaaa aaaagcggaa aaaagcggaa aaaaagagaa aaaaaatcgc aaaatcggaa      900
aaataggggg aaaagacgca aaacgcaag gaggggggag tatatgacac tgataagcaa      960
gctcacaacg gttcctctta ttttttttcct catcttctgc ctaggttccc aaaatcccag    1020
atgcttctct ccagtgccaa agtaagtac cccacaggtt tcggccgaa aattccacgt       1080 gcagcaacgt cgtgtggggt gttaaaatgt gggggggga ccaggacaag aggctcttgt      1140
gggagccgaa tgagagcaca aagcgggcgg gtgtgataag ggcattttg cccattttcc      1200 cttctcctgt ctctccgacg gtgatggcgt tgtgcgtcct ctatttcttt ttatttcttt     1260
ttgttttatt tctctgacta ccgatttggt ttgatttcct caaccccaca caaataagct     1320
cgggccgagg aatatatata tacacggaca cagtcgccct gtggacaaca cgtcactacc    1380
tctacgatac acacaataac ttcgtataat gtatgctata cgaagttata ccctccttga    1440
cagtcttgac gtgcgcagct cagggggcatg atgtgactgt cgcccgtaca tttagcccat   1500
acatccccat gtataatcat ttgcatccat acattttgat ggccgcacgg cgcgaagcaa    1560
aaattacggc tcctcgctgc agacctgcga gcagggaaac gctcccctca cagacgcgtt    1620
gaattgtccc cacgccgcgc ccctgtagag aaatataaaa ggttaggatt tgccactgag    1680
gttcttcttt catatacttc cttttaaaat cttgctagga tacagttctc acatcacatc    1740
cgaacataaa caaccatggg taaaaagcct gaactcaccg cgacgtctgt cgagaagttt    1800
ctgatcgaaa agttcgacag cgtctccgac ctgatgcagc tctcggaggg cgaagaatct   1860
cgtgctttca gcttcgatgt aggagggcgt ggatatgtcc tgcgggtaaa tagctgcgcc    1920 gatggttct acaaagatcg ttatgtttat cggcactttg catcggccgc gctcccgatt     1980
ccggaagtgc ttgacattgg ggaattcagc gagagcctga cctattgcat ctcccgccgt   2040
gcacagggtg tcacgttgca agacctgcct gaaaccgaac tgcccgctgt tctgcagccg   2100
gtcgcggagg ccatggatgc gatcgctgcg gccgatctta gccagacgag cgggttcggc    2160
ccattcggac cgcaaggaat cggtcaatac actacatggc gtgatttcat atgcgcgatt    2220
gctgatcccc atgtgtatca ctggcaaact gtgatggacg acaccgtcag tgcgtccgtc    2280
gcgcaggctc tcgatgagct gatgctttgg gccgaggact gccccgaagt ccggcacctc    2340
gtgcacgcgg atttcggctc caacaatgtc ctgacggaca atggccgcat aacagcggtc    2400
attgactgga gcgaggcgat gttcggggat tcccaatacg aggtcgccaa catcttcttc    2460
tggaggccgt ggttggcttg tatggagcag cagacgcgct acttcgagcg gaggcatccg    2520
gagcttgcag gatcgccgcg gctccgggcg tatatgctcc gcattggtct tgaccaactc    2580
tatcagagct tggttgacgg caatttcgat gatgcagctt gggcgcaggg tcgatgcgac    2640
gcaatcgtcc gatccggagc cgggactgtc gggcgtacac aaatcgcccg cagaagcgcg    2700
gccgtctgga ccgatggctg tgtagaagta ctcgccgata gtggaaaccg acgccccagc    2760
actcgtccga gggcaaagga ataatcagta ctgacaataa aaagattctt gttttcaaga    2820
acttgtcatt tgtatagttt ttttatattg tagttgttct attttaatca aatgttagcg    2880
tgatttatat tttttttcgc ctcgacatca tctgcccaga tgcgaagtta agtgcgcaga    2940
aagtaatatc atgcgtcaat cgtatgtgaa tgctggtcgc tatactgctg tcgattcgat    3000
```

```
actaacgccg ccatccagtt taaacgaggg gtaccgagat atcctgcagc ggccgcgata    3060
acttcgtata atgtatgcta tacgaagtta tatggagcgt gtgttctgag tcgatgtttt    3120
ctatggagtt gtgagtgtta gtagacatga tgggtttata tatgatgaat gaatagatgt    3180
gattttgatt tgcacgatgg aattgagaac tttgtaaacg tacatgggaa tgtatgaatg    3240
tgggggtttt gtgactggat aactgacggt cagtggacgc cgttgttcaa atatccaaga    3300
gatgcgagaa actttgggtc aagtgaacat gtcctctctg ttcaagtaaa ccatcaacta    3360
tgggtagtat atttagtaag gacaggagtt gagagaggaa agttgccatt ctttggagtc    3420
ccagaaacgt attttcgcgt tccaagatca aattagtaga gtaatacggg cacgggaatc    3480
cattcatagt ctcaattttc ccataggtgt gctacaaggt gttgagatgt ggtacagtac    3540
caccatgatt cgagataaag agcccagaag tcattgatga ggtcaagaaa tacacagatc    3600
tacagctcaa tacaatgaat atcttctttc atattcttca ggtgacacca agggtgtcta    3660
ttttccccag aaatgcgtga aaaggcgcgt gtgtagcgtg gagtatgggt tcggttggcg    3720
tatccttcat atatcgacga aatagtaggg caagagatga caaaaagtat ctatatgtag    3780
acagcgtaga atatggattt gattggtata aattcattta ttgcgtgtct cacaaatact    3840
ctcgataagt tgggggttaaa ctggagatgg aacaatgtcg atatctcgac atattttgat    3900
atttgtactg ttgatagtga taaaaagtag accgttcgaa tctcgacaag gagaagagtc    3960
caatgaaata ggttccatca tcattcgtca tagttaaacg ccgctggttg ccattactat    4020
ccgtcttgac tacaaccca actcagccta gaccacagcg aagagaatca gtttggagac    4080
cgaaaatgag cggcgtaatc atggtcatag ctgtttcctg tgtgaaattg ttatccgctc    4140
acaattccac acaacatacg agccggaagc ataaagtgta aagcctgggg tgcctaatga    4200
gtgagctaac tcacattaat tgcgttgcgc tcactgcccg ctttccagtc gggaaacctg    4260
tcgtgccagc tgcattaatg aatcggccaa cgcgcgggga gaggcggttt gcgtattggg    4320
cgctcttccg cttcctcgct cactgactcg ctgcgctcgg tcgttcggct gcggcgagcg    4380
gtatcagctc actcaaaggc ggtaatacgg ttatccacag aatcagggga taacgcagga    4440
aagaacatgt gagcaaaagg ccagcaaaag gccaggaacc gtaaaaaggc cgcgttgctg    4500
gcgtttttcc ataggctccg ccccccctgac gagcatcaca aaaatcgacg ctcaagtcag    4560
aggtggcgaa acccgacagg actataaaga taccaggcgt ttccccctgg aagctccctc    4620
gtgcgctctc ctgttccgac cctgccgctt accggatacc tgtccgcctt tctcccttcg    4680
ggaagcgtgg cgctttctca tagctcacgc tgtaggtatc tcagttcggt gtaggtcgtt    4740
cgctccaagc tgggctgtgt gcacgaaccc cccgttcagc ccgaccgctg cgccttatcc    4800
ggtaactatc gtcttgagtc aacccggta  agacacgact tatcgccact ggcagcagcc    4860
actggtaaca ggattagcag agcgaggtat gtaggcggtg ctacagagtt cttgaagtgg    4920
tggcctaact acggctacac tagaagaaca gtatttggta tctgcgctct gctgaagcca    4980
gttaccttcg gaaaaagagt tggtagctct tgatccggca acaaaccac cgctggtagc    5040 ggtggttttt ttgtttgcaa gcagcagatt acgcgcagaa aaaaaggatc tcaagaagat    5100
cctttgatct tttctacggg gtctgacgct cagtggaacg aaaactcacg ttaagggatt    5160
ttggtcatga gattatcaaa aaggatcttc acctagatcc ttttaaatta aaaatgaagt    5220
tttaaatcaa tctaaagtat atatgagtaa acttggtctg acagttacca atgcttaatc    5280
agtgaggcac ctatctcagc gatctgtcta tttcgttcat ccatagttgc ctgactcccc    5340
gtcgtgtaga taactacgat acgggagggc ttaccatctg gccccagtgc tgcaatgata    5400
```

-continued

```
ccgcgagacc cacgctcacc ggctccagat ttatcagcaa taaaccagcc agccggaagg    5460
gccgagcgca gaagtggtcc tgcaacttta tccgcctcca tccagtctat taattgttgc    5520
cgggaagcta gagtaagtag ttcgccagtt aatagtttgc gcaacgttgt tgccattgct    5580
acaggcatcg tggtgtcacg ctcgtcgttt ggtatggctt cattcagctc cggttcccaa    5640
cgatcaaggc gagttacatg atcccccatg ttgtgcaaaa aagcggttag ctccttcggt    5700
cctccgatcg ttgtcagaag taagttggcc gcagtgttat cactcatggt tatggcagca    5760
ctgcataatt ctcttactgt catgccatcc gtaagatgct tttctgtgac tggtgagtac    5820
tcaaccaagt cattctgaga atagtgtatg cggcgaccga gttgctcttg cccggcgtca    5880
atacgggata taccgcgcc acatagcaga actttaaaag tgctcatcat tggaaaacgt    5940
tcttcggggc gaaaactctc aaggatctta ccgctgttga gatccagttc gatgtaaccc    6000
actcgtgcac ccaactgatc ttcagcatct tttactttca ccagcgtttc tgggtgagca    6060
aaaacaggaa ggcaaaatgc cgcaaaaaag gaataagggc gacacggaaa atgttgaata    6120
ctcatactct tcctttttca atattattga agcatttatc agggttattg tctcatgagc    6180
ggatacatat ttgaatgtat ttagaaaaat aaacaaatag gggttccgcg cacatttccc    6240
cgaaaagtgc cacctgacgt ctaagaaacc attattatca tgacattaac ctataaaaat    6300
aggcgtatca cgaggccctt tcgtc                                          6325
```

<210> SEQ ID NO 88
<211> LENGTH: 34
<212> TYPE: DNA
<213> ORGANISM: Artificial Sequence
<220> FEATURE:
<223> OTHER INFORMATION: primer

<400> SEQUENCE: 88

```
tagtgttttt gttggttttt atttgatttg ttgg                                34
```

<210> SEQ ID NO 89
<211> LENGTH: 29
<212> TYPE: DNA
<213> ORGANISM: Artificial Sequence
<220> FEATURE:
<223> OTHER INFORMATION: primer

<400> SEQUENCE: 89

```
gctcattttc ggtctccaaa ctgattctc                                      29
```

<210> SEQ ID NO 90
<211> LENGTH: 23
<212> TYPE: DNA
<213> ORGANISM: Artificial Sequence
<220> FEATURE:
<223> OTHER INFORMATION: primer

<400> SEQUENCE: 90

```
gaacggttcg acccagtcac gtg                                            23
```

<210> SEQ ID NO 91
<211> LENGTH: 24
<212> TYPE: DNA
<213> ORGANISM: Artificial Sequence
<220> FEATURE:
<223> OTHER INFORMATION: primer

```
<400> SEQUENCE: 91
accctccttg acagtcttga cgtg                                              24
```

METHOD OF PRODUCING 13-HYDROXY-9(Z)-OCTADECENOIC ACID

This application is a Continuation of, and claims priority under 35 U.S.C. § 120 to, International Application No. PCT/JP2019/015013, filed Apr. 4, 2019, and claims priority therethrough under 35 U.S.C. § 119 to Japanese Patent Application No. 2018-074191, filed Apr. 6, 2018, the entireties of which are incorporated by reference herein. Also, the Sequence Listing filed electronically herewith is hereby incorporated by reference (File name: 2020-09-28T_US-620_Seq_List; File size: 147 KB; Date recorded: Sep. 28, 2020).

BACKGROUND

Technical Field

The present invention relates to a method of producing 13-hydroxy-9(Z)-octadecenoic acid.

Background Art

δ-Decalactone is useful as a perfume. δ-Decalactone can be produced from 13-hydroxy-9(Z)-octadecenoic acid (13-HOD) (Patent Literature 1, Non-patent Literatures 2 and 5). Therefore 13-HOD is useful as an intermediate of producing δ-decalactone.

Patent Literature 1 describes a method of producing 13-HOD from linoleic acid using linoleate 13-hydratase (13-LAH) from *Lactobacillus acidophilus*, and a method of producing δ-decalactone from 13-HOD using *Waltomyces lipofer*. Non-patent Literature 1 describes a method of producing 13-HOD using *Escherichia coli* introduced with 13-LAH. Non-patent Literature 2 describes a method of producing δ-decalactone from linoleic acid through 13-HOD. Non-patent Literature 3 describes an evolutionary lineage of LAH, and also describes that 13-LAH was found in *L. acidophilus*. Non-patent Literature 4 describes that 13-LAH was found from *L. acidophilus* and a catalytic function of 13-LAH for a conversion reaction from linoleic acid to 13-HOD was identified. Non-patent Literature 5 describes an outline of decalactone production.

PATENT LITERATURES

Patent Literature 1: Korean Patent Application Publication KR 1020150098497A

NON-PATENT LITERATURES

Non-patent Literature 1: J Park et al., J. Biotechnol., 208, 1-10 (2015)
Non-patent Literature 2: H Oh et al., Adv. Synth. Catal., 357, 408-416 (2015)
Non-patent Literature 3: Y Y Chen et al., Front Microbiol., 7, e1561 (2016)
Non-patent Literature 4: K Kim et al., Biotech. Bioeng. 112, 2206-2213 (2015)
Non-patent Literature 5: Alina Swizdor et al., Int. J. Mol. Sci., 13, 16514-16543 (2012).

SUMMARY

It is an aspect of the present invention to provide methods of producing 13-HOD and δ-decalactone with enhanced productivity. 13-LAH has been found to have an enzyme activity that is superior to that of 13-LAH from *L. acidophilus*.

It is an aspect of the present invention to provide a method of producing 13-hydroxy-9(Z)-octadecenoic acid, comprising producing 13-hydroxy-9(Z)-octadecenoic acid from linoleic acid in the presence of a transformed microorganism that produces a protein selected from the group consisting of: (A) a protein comprising an amino acid sequence selected from the group consisting of SEQ ID NOs: 4, 5, 8 to 10, 13, and 14; (B) a protein comprising an amino acid sequence containing one or several amino acid substitutions, deletions, insertions or additions in the amino acid sequence selected from the group consisting of SEQ ID NOs: 4, 5, 8 to 10, 13, and 14, and having a linoleate 13-hydratase activity; and (C) a protein comprising an amino acid sequence having 90% or more identity to the amino acid sequence selected from the group consisting of SEQ ID NOs: 4, 5, 8 to 10, 13, and 14, and having a linoleate 13-hydratase activity.

It is a further aspect of the present invention to provide the method as described above, wherein said protein is: (A') a protein comprising an amino acid sequence selected from the group consisting of SEQ ID NOs: 8, 9, 13, and 14; (B') a protein comprising an amino acid sequence containing one or several amino acid substitutions, deletions, insertions or additions in the amino acid sequence selected from the group consisting of SEQ ID NOs: 8, 9, 13, and 14, and having a linoleate 13-hydratase activity; or (C') a protein comprising an amino acid sequence having 90% or more identity to the amino acid sequence selected from the group consisting of SEQ ID NOs: 8, 9, 13, and 14, and having a linoleate 13-hydratase activity.

It is a further aspect of the present invention to provide the method as described above, wherein said identity is 95% or more.

It is a further aspect of the present invention to provide the method as described above, wherein said protein is linoleate 13-hydratase from a microorganism selected from the group consisting of *Lactobacillus gallinarum*, *Lactobacillus crispatus*, *Lactobacillus hamsteri*, *Lactobacillus gasseri*, *Pediococcus claussenii*, *Streptococcus mutans*, and *Streptococcus equinus*.

It is a further aspect of the present invention to provide the method as described above, wherein said protein is linoleate 13-hydratase from a microorganism selected from the group consisting of *Lactobacillus hamsteri*, *Lactobacillus gasseri*, *Streptococcus mutans*, and *Streptococcus equinus*.

It is a further aspect of the present invention to provide the method as described above, wherein said transformed microorganism is a microorganism comprising an expression unit containing a polynucleotide encoding said protein and a promoter operably linked thereto.

It is a further aspect of the present invention to provide the method as described above, wherein said transformed microorganism is a bacterium belonging to the genus *Escherichia*.

It is a further aspect of the present invention to provide the method as described above, wherein said transformed microorganism is *Escherichia coli*.

It is a further aspect of the present invention to provide a method for producing δ-decalactone, comprising: (i) producing 13-hydroxy-9(Z)-octadecenoic acid from linoleic acid in the presence of a transformed microorganism that produces a protein selected from the group consisting of: (A) a protein comprising an amino acid sequence selected from the group consisting of SEQ ID NOs: 4, 5, 8 to 10, 13, and 14; (B) a protein comprising an amino acid sequence containing one or several amino acid substitutions, deletions, insertions or additions in the amino acid sequence selected from the group consisting of SEQ ID NOs: 4, 5, 8 to 10, 13, and 14, and having a linoleate 13-hydratase activity; and (C) a protein comprising an amino acid sequence having 90% or more identity to the amino acid sequence selected from the group consisting of SEQ ID NOs: 4, 5, 8 to 10, 13, and 14, and having a linoleate 13-hydratase activity; and (ii) producing δ-decalactone from 13-hydroxy-9(Z)-octadecenoic acid.

It is a further aspect of the present invention to provide the method as described above, wherein (ii) is performed in the presence of a microorganism having a β oxidation activity.

It is a further aspect of the present invention to provide the method as described above, wherein said microorganism having the β oxidation activity is a microorganism having lowered aldehyde oxidase activity compared to an activity of a wild type enzyme.

It is a further aspect of the present invention to provide the method as described above, wherein said microorganism having the β oxidation activity is *Yarrowia lipoytica*.

13-hydroxy-9(Z)-octadecenoic acid can efficiently be produced by biological methods as described herein. Furthermore, according to the method as described herein, δ-decalactone can efficiently be produced by biological methods.

DETAILED DESCRIPTION

Figure 1:
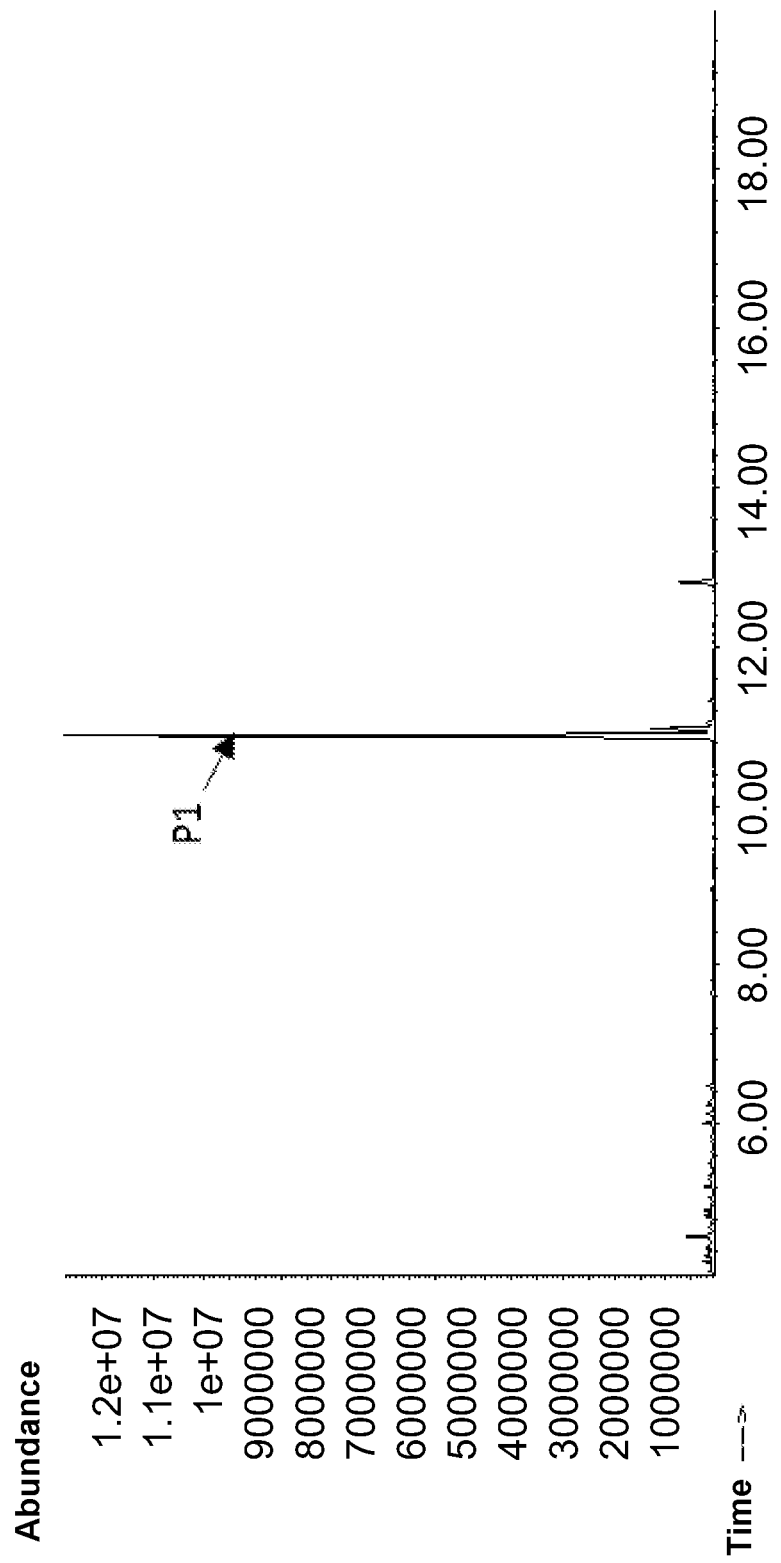
FIG. 1 shows an MS (mass spectroscopy) chromatogram obtained from a reaction solution of BLR(DE3)/pET-22b(+)Km$^R$ strain.

The present invention provides a method of producing 13-hydroxy-9(Z)-octadecenoic acid. The method as described herein includes steps of producing 13-hydroxy-9(Z)-octadecenoic acid from linoleic acid in the presence of a transformed microorganism that produces a protein such as:

(A) a protein having an amino acid sequence of SEQ ID NO: 4, 5, 8 to 10, 13, or 14, particularly of SEQ ID NOs: 8, 9, 13, or 14;

(B) a protein having an amino acid sequence containing one or several amino acid substitutions, deletions, insertions or additions in the amino acid sequence of SEQ ID NO: 4, 5, 8 to 10, 13, or 14, particularly of SEQ ID NO: 8, 9, 13, or 14, and having a linoleate 13-hydratase activity; and (C) a protein having an amino acid sequence having 90% or more identity to the amino acid sequence of SEQ ID NOs: 4, 5, 8 to 10, 13, or 14, particularly of SEQ ID NO: 8, 9, 13, or 14, and having a linoleate 13-hydratase activity.

In the protein (B), one or several amino acid residues can be modified by one, two, three, or four mutations such as substitutions, deletions, insertions, or additions of amino acid residues. The mutations of the amino acid residues may be introduced into one region in an amino acid sequence, or may be introduced into multiple different regions in the amino acid sequence. The term "one or several" refers to the number that does not greatly impair an activity of a protein. The number represented by the term "one or several" is, for example, 1 to 60, 1 to 50, 1 to 40, 1 to 30, 1 to 20, 1 to 10, or 1 to 5 (e.g., 1, 2, 3, 4 or 5).

The percent identity to protein (C) is 90% or more. The identity may be 91% or more, 92% or more, 93% or more, 94% or more, 95% or more, 96% or more, 97% or more, 98% or more, or 99% or more. The calculation of a percent identity of a polypeptide (protein) can be carried out by the algorithm blastp. More specifically, the calculation of a percent identity of a polypeptide can be carried out by the algorithm blastp in the default settings of Scoring Parameters (Matrix: BLOSUM62; Gap Costs: Existence=11 Extension=1; Compositional Adjustments: Conditional compositional score matrix adjustment) provided by National Center for Biotechnology Information (NCBI). The calculation of a percent identity of a polynucleotide (gene) can be carried out by the algorithm blastn. More specifically, the calculation of a percent identity of a polynucleotide can be carried out by the algorithm blastn in the default settings of Scoring Parameters (Match/Mismatch Scores=1, −2; Gap Costs=Linear) provided by NCBI.

The "linoleate 13-hydratase activity" refers to an activity that converts linoleic acid to 13-hydroxy-9(Z)-octadecenoic acid (13-HOD). The proteins (B) and (C) may each have, for example, 60% or more, 70% or more, 80% or more, 85% or more, 90% or more, 94% or more, 96% or more, 98% or more, or equivalent (i.e., 100%) activity based on an activity of a protein having a corresponding amino acid sequence of SEQ ID NOs: 4, 5, 8 to 10, 13, or 14, particularly a protein having only a corresponding amino acid sequence, when the activity is measured under a certain measurement condition. The following condition can be employed as such a certain measurement condition.

A transformed microorganism that expresses a target protein (e.g., *Escherichia coli* BLR(DE3) strain transformed with a vector where DNA including a nucleotide sequence encoding the target protein was incorporated into pET-22b (+)) is cultured by preculture (e.g., cultured in 3 mL SOC medium at 37° C. for 16 to 24 hours) and main culture (e.g., 0.5 mL of the preculture medium is cultured in 50 mL SOC medium at 37° C. for 2 hours); isopropyl-β-thiogalactopyranoside (IPTG) is added to the culture, which is then cultured (e.g., at 16° C. for 22 to 24 hours); microbial cells are collected from the obtained culture medium in a certain amount (e.g., 4 mL), and washed (e.g., twice with 0.8 M NaCl); the microbial cells are suspended in a linolenic acid-containing conversion reaction solution (e.g., 100 mL citrate/phosphate buffer (pH 6.0), Tween 20 at a final concentration of 25 wt %, linolenic acid at a final concentration of 50 g/L) in a certain amount (e.g., 1 mL); the conversion reaction solution is reacted under a certain condition (37° C., shaking at 120 rpm, 5 hours); the conversion reaction solution in a certain amount (e.g., 0.2 mL) is extracted with an organic solvent (e.g., 0.6 mL of ethyl acetate); 60 µL of a derivatization reagent (e.g., BSA+TMCS, 5:1) is added to an organic solvent layer in a certain amount (e.g., 30 µL) and the mixture is left to stand at room temperature for 2 hours to silylate fatty acids, and peaks of silylated linolenic acid and silylated 13-HOD are measured to evaluate the linoleate 13-hydratase activity.

In the proteins (B) and (C), mutations may be introduced into sites in a catalytic domain and sites other than the catalytic domain as long as target properties can be retained. A position of an amino acid residue that can retain the target property and to which the mutation may be introduced is evident to a person skilled in the art. Specifically, a person skilled in the art can recognize correlation between structures and functions by (1) comparing amino acid sequences of multiple proteins having a similar type of property, (2) revealing relatively conserved regions and relatively not conserved regions, and then (3) predicting regions capable of playing a functionally important role and regions incapable of playing a functionally important role from the relatively conserved regions and the relatively not conserved regions, respectively. Therefore, a person skilled in the art can identify the position of the amino acid residue to which the mutation may be introduced in the amino acid sequence of the chosen protein.

When an amino acid residue is mutated by substitution, the substitution of the amino acid residue may be conservative substitution. The term "conservative substitution" refers to substitution of a certain amino acid residue with an amino acid residue having a similar side chain. Families of amino acid residues having the similar side chain are well-known in the art. For example, such families include amino acids having a basic side chain (e.g., lysine, arginine, histidine), amino acids having an acidic side chain (e.g., aspartic acid, glutamic acid), amino acids having an uncharged polar side chain (e.g., asparagine, glutamine, serine, threonine, tyrosine, cysteine), amino acids having a non-polar side chain (e.g., glycine, alanine, valine, leucine, isoleucine, proline, phenylalanine, methionine, tryptophan), amino acids having a position branched side chain (e.g., threonine, valine, isoleucine), amino acids having an aromatic side chain (e.g., tyrosine, phenylalanine, tryptophan, histidine), amino acids having a hydroxyl group (e.g., alcoholic, phenolic)-containing side chain (e.g., serine, threonine, tyrosine), and amino acids having a sulfur-containing side chain (e.g., cysteine, methionine). Preferably, the conservative substitution of amino acids may be the substitution between aspartic acid and glutamic acid, the substitution between arginine and lysine and histidine, the substitution between tryptophan and phenylalanine, the substitution between phenylalanine and valine, the substitution between leucine and isoleucine and alanine, and the substitution between glycine and alanine.

The transformed microorganism used for the method as described herein can have an enhanced linoleate 13-hydratase activity compared to a transformed microorganism that produces linoleate 13-hydratase from *Lactobacillus acidophilus* (a protein having an amino acid sequence of SEQ ID NO:1). Specifically, the transformed microorganism used for the method can have the linoleate 13-hydratase activity that exceeds 1.0 time, and may have the linoleate 13-hydratase activity that is, for example, 1.01 times or higher, 1.1 times or higher, 1.2 times or higher, 1.3 times or higher, 1.4 times or higher, or 2 times or higher based on the activity from the transformed microorganism that produces the protein having the amino acid sequence of SEQ ID NO:1.

The protein produced by the transformed microorganism used for the method may also be a fusion protein linked to a heterogeneous portion through a peptide bond. Such a heterogeneous portion includes, for example, peptide components that make purification of a target protein easy (e.g., tag portions including histidine tag and Strep-tag II; proteins utilized for the purification of the target protein including glutathione-S-transferase, maltose binding protein and mutants thereof), peptide components that enhance solubility of the target protein (e.g., Nus-tag), peptide components that work as a chaperon (e.g., trigger factor), peptide components having another function (e.g., a full length protein or parts thereof), and linkers.

The protein produced by the transformed microorganism used for the method can be linoleate 13-hydratase from a microorganism such as *Lactobacillus gallinarum*, *Lactobacillus crispatus*, *Lactobacillus hamsteri*, *Lactobacillus gasseri*, *Pediococcus claussenii*, *Streptococcus mutans*, and *Streptococcus equinus*, or particularly linoleate 13-hydratase from a microorganism such as *Lactobacillus hamsteri*, *Lactobacillus gasseri*, *Streptococcus mutans*, and *Streptococcus equinus*.

The transformed microorganism may be, for example, a microorganism that includes an expression unit containing a polynucleotide encoding the above-described protein and a promoter operably linked thereto. The term "transformation" can mean not only introduction of a polynucleotide to a host cell but also modification of genome in the host cell.

The polynucleotide encoding the above-described protein may be a polynucleotide as follows:

(a) a polynucleotide having a nucleotide sequence of SEQ ID NO:18, 19, 22 to 24, 27, or 28, particularly of SEQ ID NO: 22, 23, 27, or 28;

(b) a polynucleotide that hybridizes with a polynucleotide consisting of a nucleotide sequence complementary to the nucleotide sequence of SEQ ID NOs:18, 19, 22 to 24, 27, or 28, particularly of SEQ ID No: 22, 23, 27, or 28 under a stringent condition, and encodes a protein having a linoleate 13-hydratase activity;

(c) a polynucleotide having a nucleotide sequence having 90% or more identity to the nucleotide sequence of SEQ ID NO:18, 19, 22 to 24, 27, or 28, particularly of SEQ ID NO: 22, 23, 27, or 28, and encoding a protein having a linoleate 13-hydratase activity; and (d) a degenerate mutant of the polynucleotide as described in (a) to (c) above.

The above polynucleotide may be DNA or RNA. The nucleotide sequences of SEQ ID NOs:18, 19, 22 to 24, 27, and 28 collectively encode the amino acid sequence of SEQ ID NO:30. The nucleotide sequence of SEQ ID NO:31 encodes amino acid sequences of SEQ ID NOs: 4, 5, 8 to 10, 13, and 14, respectively.

In the above polynucleotide (b), the term "stringent condition" refers to a condition where a so-called specific hybrid is formed and a non-specific hybrid is not formed. For example, the stringent condition includes hybridization at about 45° C. in 6×SSC (sodium chloride/sodium citrate) followed by washing once or twice or more at 50 to 56° C. in 0.2×SSC and 0.1% SDS.

The identity % in the above polynucleotide (c) may be 90% or more, 91% or more, 92% or more, 93% or more, 94% or more, 95% or more, 96% or more, 97% or more, 98% or more, or 99% or more.

In the above polynucleotide (d), the term "degenerate mutant" refers to a polynucleotide mutant in which at least one codon encoding a given amino acid residue in a polynucleotide before mutation has been changed to another codon encoding the same amino acid residue. Such a degenerate mutant is a mutant based on a silent mutation, and thus a protein encoded by the degenerate mutant is the same as a protein encoded by a polynucleotide before the mutation.

The degenerate mutant is a polynucleotide mutant in which a codon is changed to adapt to a codon usage of a host cell to which it is to be introduced. When a certain gene is expressed in a heterogeneous host cell (e.g., microorganism), due to difference in codon usage, corresponding tRNA molecular species is sometimes not sufficiently supplied to result in a reduced translation efficiency and/or incorrect translation (e.g., termination of translation). For example, a low frequency of codon usage shown in Table 1 is known in *Escherichia coli*.

TABLE 1

Low frequency of codon usage in *Escherichia coli*

| Amino acid residue | Codon | Low frequency codon |
|---|---|---|
| Arg | AGG/AGA/CGG/CGA/CGU/CGC | AGG/AGA/CGG/CGA |
| Gly | GGG/GGA/GGU/GGC | GGA |
| Ile | AUA/AUU/AUC | AUA |
| Leu | UUG/UUA/CUG/CUA/CUU/CUC | CUA |
| Pro | CCG/CCA/CCU/CCC | CCC |

Therefore, it is possible to use a degenerate mutant that adapts to a codon usage of a host cell as described later. For example, the degenerate mutants may be those in which a codon(s) encoding one or more amino acid residues such as an arginine residue, a glycine residue, an isoleucine residue, a leucine residue, and a proline residue has been changed. More specifically, the degenerate mutants may be those in which one or more codons of low codon usages (e.g., AGG, AGA, CGG, CGA, GGA, AUA, CUA and CCC) have been changed. The degenerate mutant may include changes of one or more, such as one, two, three, four or five, codons such as the following:

i) change of at least one codon of four codons encoding Arg (AGG, AGA, CGG and CGA) to another codon that encodes Arg (CGU or CGC);

ii) change of one codon encoding Gly (GGA) to another codon encoding Gly (GGG, GGU or GGC);

iii) change of one codon encoding Ile (AUA) to another codon encoding Ile (AUU or AUC);

(iv) change of one codon encoding Leu (CUA) to another codon encoding Leu (UUG, UUA, CUG, CUU or CUC); and (v) change of one codon encoding Pro (CCC) to another codon encoding Pro (CCG, CCA or CCU).

When the degenerate mutant is RNA, a nucleotide residue "U" should be used as described above, but when the degenerate mutant is DNA, "T" in place of the nucleotide residue "U" should be utilized. The number of mutations of nucleotide residues for adapting the codon usage in a host cell is not particularly limited as long as the nucleotide residues encode the same protein before and after the mutation, and for example is 1 to 400, 1 to 300, 1 to 200, or 1 to 100.

A low frequency codon can easily be identified based on a type of any host cell and genome sequence information by utilizing known technology in the art. Therefore, the degenerate mutant may include the change of a low frequency codon to a non-low frequency codon (e.g., high frequency codon). Methods of designing mutants by taking account of not only the low frequency codons but also factors such as compatibility to a genomic GC content of a production bacterium strain have been described (Alan Villalobos et al., Gene Designer: a synthetic biology tool for constructing artificial DNA segments, BMC Bioinformatics. 2006 Jun. 6; 7:285). Thus, such methods may be utilized. In this way, the mutants described above can appropriately be made depending on a type of any host cell (e.g., a microorganism as described herein) into which it can be introduced.

The term "expression unit" refers to a minimum unit including a given polynucleotide to be expressed as a protein and a promoter operably linked thereto and enabling transcription of the polynucleotide and further production of the protein encoded by the polynucleotide. The expression unit may further include elements such as a terminator, a ribosome binding site, and a drug resistant gene. The expression unit may be DNA or RNA, but is preferably DNA. The expression unit may be homologous (i.e., inherent) or heterologous (i.e., non-inherent) to a host cell. The expression unit may also be an expression unit including one polynucleotide to be expressed as a protein and a promoter operably linked thereto (i.e., an expression unit enabling expression of monocistronic mRNA) or an expression unit including a plurality of polynucleotides, for example, 2 or more, 3 or more, 4 or more, 5 or more, 10 or more polynucleotides, and promoters operably linked thereto (i.e., an expression unit enabling expression of polycistronic mRNA). The expression unit can be included in a genomic region (e.g., a natural genomic region that is a natural locus in which the polynucleotide encoding the above protein inherently occurs or a non-natural genomic region that is not the natural locus) or a non-genomic region (e.g., intracellularly) in a microorganism (host cell). The expression unit may be included at one or two or more (e.g., 1, 2, 3, 4 or 5) different positions in the genomic region. Specific forms of the expression unit included in the non-genomic region include, for example, plasmids, viral vectors and artificial chromosomes.

A promoter that constitutes the expression unit is not particularly limited as long as it can allow to express a protein encoded by a polynucleotide linked downstream thereto in a host cell. For example, a promoter may be homologous or heterologous to a host cell, but is preferably heterologous. For example, constitutive or inducible promoters commonly used for the production of recombinant proteins can be used. Such a promoter includes, for example, PhoA promoter, PhoC promoter, T7 promoter, T5 promoter, T3 promoter, lac promoter, trp promoter, trc promoter, tac promoter, PR promoter, PL promoter, SP6 promoter, arabinose inducible promoter, cold shock promoter, and tetracycline inducible promoter. A promoter having a potent transcription activity in a host cell can be used. The promoter having the potent transcription activity in the host cell includes, for example, promoters of genes highly expressed in host cells and promoters from viruses.

Host cells used as the transformed microorganism include, for example, bacteria such as bacteria belonging to Enterobacteriaceae, and fungi. The bacteria may be gram positive bacteria or gram negative bacteria. The gram positive bacteria include, for example, bacteria in the genera *Bacillus* and *Corynebacterium*. *Bacillus subtilis* is a particular example as the bacterium in the genus *Bacillus*. *Corynebacterium glutamicum* is a particular example as the bacterium in the genus *Corynebacterium*. The gram negative bacteria include, for example, bacteria in genera *Escherichia* and *Pantoea*. *Escherichia coli* is a particular example as the bacterium in the genus *Escherichia*. *Pantoea ananatis* is a particular example as the bacterium in the genus *Pantoea*. Microorganisms in genera *Saccharomyces*, *Schizosaccharomyces*, *Yarrowia*, *Waltomyces* (also referred to as genus *Lipomyces*) are a particular example as fungi. *Saccharomyces cerevisiae* is a particular example as the microorganism in the genus *Saccharomyces*. *Schizosaccharomyces pombe* is a particular example as the microorganism in the genus *Schizosaccharomyces*. *Yarrowia lipoytica* is a particular example as the microorganism in the genus *Yarrowia*. *Waltomyces lipofer* (also referred to as *Lipomyces lipofer*) is a particular example as the microorganism in the genus *Waltomyces* (genus *Lipomyces*).

The transformed microorganism can be made by any known method in the art. For example, the transformed microorganism as described above can be made by a method using an expression vector (e.g., a competent cell method, an electroporation method) or genome modification technology. When the expression vector is an integrative vector that produces homologous recombination with genomic DNA of a host cell, an expression unit can be integrated into the genomic DNA of the host cell by transformation. On the other hand, when the expression vector is a non-integrative vector that does not produce homologous recombination with genomic DNA of a host cell, the expression unit is not integrated into the genomic DNA of the host cell by transformation, and can remain as a an expression vector and exist independently from the genomic DNA. Alternatively, according to genome-editing technology (e.g., CRISPR/Cas System, Transcription Activator-Like Effector Nucleases (TALEN)), it is possible to integrate the expression unit into the genomic DNA of the host cell and modify the expression unit inherently present in the host cell.

An expression vector may further include elements such as a terminator, a ribosome binding site and a drug resistant gene that function in a host cell as an expression unit, in addition to the expression unit described above. The drug resistant genes include, for example, genes resistant to drugs such as tetracycline, ampicillin, kanamycin, hygromycin, and phosphinothricin.

An expression vector may also further include a region capable of homologous recombination with genome DNA of a host cell for the homologous recombination with the genome of the host cell. For example, the expression vector may be designed so that an expression unit contained therein is located between a pair of homologous regions (e.g., homologous homology arm, loxP, FRT to a certain sequence in the genome of the host cell). A genomic region (target of a homologous region) of a host cell to which an expression unit is to be introduced is not particularly limited, and may be a locus of a gene highly expressed in amount in the host cell.

An expression vector may be a plasmid, a viral vector, a phage, or an artificial chromosome. The expression vector may be an integrative vector or a non-integrative vector. The integrative vector may be a vector that is entirely integrated into the genome of the host cell. Alternatively, the integrative vector may be a vector, only a part (e.g., an expression unit) of which is integrated into the genome of the host cell. The expression vector may further be a DNA vector or an RNA vector (e.g., a retrovirus vector). The expression vector may also be a commonly used expression vector. Such an expression vector includes, for example, pUC (e.g., pUC19, Linoleic pUC18), pSTV, pBR (e.g., pBR322), pHSG (e.g., pHSG299, pHSG298, pHSG399, pHSG398), RSF (e.g., RSF1010), pACYC (e.g., pACYC177, pACYC184), pMW (e.g., pMW119, pMW118, pMW219, pMW218), pQE (e.g., pQE30), and derivatives thereof.

Linoleic acid that is a substrate used in the method as described herein can be added to a reaction system including the above 13-LAH (i.e., in the presence of a transformed microorganism producing the above 13-LAH, e.g., a culture medium including the transformed microorganism producing the above 13-LAH). Alternatively, linoleic acid produced in the reaction system can also be utilized as the substrate in the method as described herein.

When the method is performed by culturing the above transformed microorganism, those described above can be used as culture media. The culture media can contain a carbon source. The carbon source includes, for example, carbohydrate such as monosaccharides, disaccharides, oligosaccharides, and polysaccharides; invert sugar obtained by hydrolysis of sucrose; glycerol; compounds having one carbon atom (hereinafter referred to as C1 compounds) such as methanol, formaldehyde, formic acid, carbon monoxide and carbon dioxide; oils such as corn oil, palm oil and soybean oil; acetate; animal oils and fats; animal oils; fatty acids such as saturated fatty acids and unsaturated fatty acids; lipids; phospholipids; glycerolipid; glycerin fatty acid esters such as monoglyceride, diglyceride and triglyceride; polypeptides such as microbial proteins and vegetable proteins; reproducible carbon sources such as hydrolyzed biomass carbon sources; yeast extracts; or combinations thereof. Ammonium salts such as ammonium sulfate, ammonium chloride and ammonium phosphate, organic nitrogen such as hydrolyzed soybeans, ammonia gas and ammonia water can be used as nitrogen sources. As organic micronutrients, it is desirable to contain requirement substances such as vitamin B1 and L-homoserine or yeast extracts in an appropriate amount. In addition to them, potassium phosphate, magnesium sulfate, iron ion, manganese ion, and the like are added in small amounts if necessary. The media may be either natural media or synthesized media as long as the medium contains the carbon source, nitrogen source, inorganic ions and if necessary, other organic trace components.

The culture conditions of the transformed microorganism are not particularly limited, and standard cell culture conditions can be used. A culture temperature can be 4 to 40° C. or 10 to 37° C. A pH value can be about 4 to 9. Also, the culture can be performed under an aerobic, anoxic, or anaerobic condition depending on nature of a host cell.

Any appropriate methods can be used as a culture method. Such a culture method includes, for example, a batch culture method, a feeding culture method, and a continuous culture method. When the expression of a certain protein produced by the transformed microorganism is under the control of an inducible promoter such as lac promoter, the expression of the protein may be induced by adding an inducer such as IPTG (isopropyl-β-thiogalactopyranoside) to the culture medium.

The production of 13-HOD can be confirmed appropriately. For example, such confirmation can be performed by extracting 13-HOD with an organic solvent from a reaction system and subjecting the extract to gas chromatography or mass spectroscopy. Also, 13-HOD can appropriately be collected and purified from the culture medium. For example, the collection and purification of 13-HOD include extraction and fractionation with organic solvents, and a method using an inclusion compound (method in which an inclusion complex of 13-HOD is made by contacting with an inclusion compound such as cyclodextrin and subsequently 13-HOD is dissociated from the inclusion complex). The collection and purification of 13-HOD may also be performed by a method of separating by precision distillation as is the case of common perfumes. The conformation of production of 13-HOD and the collection and purification of 13-HOD may reference to, for example, WO2016/029187, US Patent Application Publication No. 2012/0246767, Japanese Unexamined Patent Application Publication No. 2002-47239, and Xie et al., Food Chem., 2009; 117: 375-380.

In another embodiment, a method of producing δ-decalactone is described. The method of producing δ-decalactone of the present invention includes the following:

(i) producing 13-hydroxy-9(Z)-octadecenoic acid from linoleic acid in the presence of a transformed microorganism having a linoleate 13-hydratase activity enhanced as compared to a transformed microorganism producing linoleate 13-hydratase from *Lactobacillus acidophilus* (a protein having an amino acid sequence of SEQ ID NO:1); and (ii) producing δ-decalactone from 13-hydroxy-9(Z)-octadecenoic acid.

Respective conditions for producing the transformed microorganism and 13-hydroxy-9(Z)-octadecenoic acid in step (i) include those described above.

Step (ii) can be performed by any chemical or biological methods (e.g., Korean Patent Application Publication No. KR1020150098497A; H Oh et al., Adv. Synth. Catal., 357, 408-416 (2015); Alina Swizdor et al., Int. J. Mol. Sci., 13, 16514-16543 (2012))

In certain embodiments, step (ii) may be performed in the presence of a microorganism having β oxidation activity.

Microorganisms having the β oxidation activity include, for example, microorganisms in the genera *Yarrowia*, *Waltomyces* (also referred to as the genus *Lipomyces*), *Saccharomyces*, and *Schizosaccharomyces*. *Yarrowia lipoytica* is a particular example as the microorganism in the genus *Yarrowia*. *Waltomyces lipofer* (also referred to as *Lipomyces lipofer*) is a particular example as the microorganism in the genus *Waltomyces* (*Lipomyces*). *Saccharomyces cerevisiae* is a particular example as the microorganism in the genus *Saccharomyces*. *Schizosaccharomyces pombe* is a particular example as the microorganism in the genus *Schizosaccharomyces*.

In order to increase an ability of producing δ-decalactone, the microorganism having the β oxidation activity may be a microorganism having a lower aldehyde oxidase activity compared to a wild type activity. The microorganism having the lower aldehyde oxidase activity compared to the wild type activity includes, for example, microorganisms modified to destroy one or more certain genes among a gene group encoding acetyl-CoA oxidase or reduce the function of acetyl-CoA oxidase. When the microorganism is *Y. lipoytica*, it is preferred to modify so as to destroy a gene encoding acetyl-CoA oxidase 3 (AOX3) that exhibits high substrate affinity for short chain fatty acids among 6 genes encoding acetyl-CoA oxidase or reduce the function of that enzyme.

The microorganism having the lower aldehyde oxidase activity compared to the wild type enzyme can be made by a method utilizing homologous recombination with the genomic DNA of the microorganism or the genome modification technology. The method of utilizing the homologous recombination includes, for example, a method of exogenously introducing into a microorganism a gene fragment (e.g., DNA fragment) having homologous regions before and after a target gene (e.g., acetyl-CoA oxidase gene) and replacing a target gene corresponding portion with a marker gene (e.g., gene resistant to a drug, such as tetracycline, ampicillin, kanamycin, hygromycin, phosphinothricin) (e.g., a competent cell method, an electroporation method). The genome modification technology includes genome-editing technology (e.g., CRISPR/Cas System, Transcription Activator-Like Effector Nucleases (TALEN)). The aldehyde oxidase activity can be measured according to a method described, for example, in Sakayu Shimizu et. al., Biochem. Biophys. Res. Commun., 91, 108-113 (1979).

13-Hydroxy-9(Z)-octadecenoic acid in step (ii) is supplied as a culture medium, a crude product or a purified product containing 13-hydroxy-9(Z)-octadecenoic acid obtained in step (i). When the culture medium obtained step (i) is used as a source of 13-hydroxy-9(Z)-octadecenoic acid, the transformed microorganism may be removed or may not be removed.

Step (ii) may be performed by inoculating the microorganism having the β oxidation activity preliminarily cultured in a medium into a culture medium containing 13-hydroxy-9(Z)-octadecenoic acid obtained in step (i), and culturing them. The microorganism to be inoculated to the culture medium may be prepared by culture in a general culture medium for microorganism (e.g., YPD medium) (preculture), subsequent culture in an inducible medium (e.g., medium containing oleic acid, arachidonic acid, stearic acid, myristic acid, palmitic acid, icosenoic acid or erucic acid) (inducible culture), and washing with buffer (e.g., phosphate buffer).

Conditions for the culture of the microorganism having the β oxidation activity (preculture, inducible culture, and culture in step (ii)) are not particularly limited, and standard cell culture conditions can be used. A culture temperature can be 4 to 40° C., or 10 to 37° C. A pH value can be about 4 to 9. Also, the culture can be performed under an aerobic, anoxic or anaerobic condition depending on the nature of the microorganism. Any appropriate method can be used as the culture method. Such a culture method includes, for example, a batch culture method, a feeding culture method and a continuous culture method.

An amount of produced δ-decalactone can be evaluated using gas chromatography (GC), a hydrogen flame ion detector (FID) and mass spectroscopy (MS).

The method of producing δ-decalactone may include collecting δ-decalactone. A method of collecting δ-decalactone includes, for example a solvent extraction process utilizing ethyl acetate, hexane, heptane, octane, decan, acetone and the like.

The method of producing δ-decalactone may further include purifying δ-decalactone. A method for purifying δ-decalactone includes, for example, methods using distillation, recrystallization, or various chromatographies.

EXAMPLES

Subsequently, the present invention is described in detail with reference to Examples, but the present invention is not limited to the following Examples.

Example 1: Construction of Expression Plasmids of Linoleate 13-Hydratase from Various Microorganisms <Search for Genes Encoding Linoleate 13-Hydratase>

Linoleate 13-hydratase (hereinafter abbreviated as 13-LAH) is known as an enzyme that hydrates a double bond at position Δ12 in linolenic acid to introduce a hydroxyl group at position C13 (US Patent Application Publication US20040197882A1). It has been reported that this enzyme is isolated from *Lactobacillus acidophilus* and produces 13-hydroxy-cis-9-octadecenoic acid (hereinafter abbreviated as 13-HOD) using linolenic acid as a substrate (Korean Patent Application Publication KR1020150098497A; Park et al., J. Biotechnol., 2015, 208: 1-10). An amino acid sequence of 13-LAH from *L. acidophilus* (hereinafter abbreviated as Laci13-LAH) is shown in SEQ ID NO:1. To newly isolate 13-LAH having a higher activity than Laci13-LAH, identity search utilizing the database was performed. Homology search was performed utilizing blastp (blast.ncbi.nlm.nih.gov/Blast.cgi) based on the amino acid sequence of *L. acidophilus* 13-LAH. As a result, 13 candidate proteins exhibiting 70% or more identity to this enzyme were extracted. The extracted candidate proteins are listed in Table 2.

TABLE 2

List of proteins exhibiting identity to 13-LAH from *L. acidophilus* (Laci13-LAH).

| Microorganism species | Annotation | Identity % to *L. acidophilus* | Amino acid sequence | Abbreviated name of gene (chemically synthesized nucleotide sequence) |
|---|---|---|---|---|
| *Lactobacillus acidophilus* | Linoleate 13-hydratase | — | SEQ ID NO: 1 | Laci13-LAH (SEQ ID NO: 15) |
| *Lactobacillus amylovorus* | Oleate hydratase | 94% | SEQ ID NO: 2 | Lamy13-LAH (SEQ ID NO: 16) |
| *Lactobacillus helveticus* | Oleate hydratase | 92% | SEQ ID NO: 3 | Lhel13-LAH (SEQ ID NO: 17) |
| *Lactobacillus gallinarum* | Oleate hydratase | 91% | SEQ ID NO: 4 | Lgal13-LAH (SEQ ID NO: 18) |
| *Lactobacillus crispatus* | Oleate hydratase | 90% | SEQ ID NO: 5 | Lcri13-L AH (SEQ ID NO: 19) |
| *Lactobacillus kefiranofaciens* | Oleate hydratase | 90% | SEQ ID NO: 6 | Lkef13-LAH (SEQ ID NO: 20) |
| *Lactobacillus intestinalis* | Oleate hydratase | 87% | SEQ ID NO: 7 | Lint13-LAH (SEQ ID NO: 21) |

TABLE 2-continued

List of proteins exhibiting identity to 13-LAH from *L. acidophilus* (Laci13-LAH).

| Microorganism species | Annotation | Identity % to *L. acidophilus* | Amino acid sequence | Abbreviated name of gene (chemically synthesized nucleotide sequence) |
|---|---|---|---|---|
| *Lactobacillus hamsteri* | Oleate hydratase | 85% | SEQ ID NO: 8 | Lham13-LAH (SEQ ID NO: 22) |
| *Lactobacillus gasseri* | Oleate hydratase | 80% | SEQ ID NO: 9 | Lgas13-LAH (SEQ ID NO: 23) |
| *Pediococcus claussenii* | Oleate hydratase | 72% | SEQ ID NO: 10 | Pcla13-LAH (SEQ ID NO: 24) |
| *Lactobacillus ruminis* | Oleate hydratase | 72% | SEQ ID NO: 11 | Lrum13-LAH (SEQ ID NO: 25) |
| *Streptococcus infantarius* | Oleate hydratase | 72% | SEQ ID NO: 12 | Sinf13-LAH (SEQ ID NO: 26) |
| *Streptococcus mutans* | Oleate hydratase | 72% | SEQ ID NO: 13 | Smut13-LAH (SEQ ID NO: 27) |
| *Streptococcus equinus* | Oleate hydratase | 72% | SEQ ID NO: 14 | Sequ13-LAH (SEQ ID NO: 28) |

<Chemical Synthesis of Genes Encoding Various 13-LAH>

Nucleotide sequences represented by SEQ ID NOs:15 to 28 optimized by codon usage of *E. coli* were synthesized by gene synthesis utilizing the artificial gene synthesis service provided by GenScript. The synthesized genes were cloned into pET-9a (from Novagen (Merck Millipore), Product Number 69431-3) at that company, and plasmids having introduced various 13-LAH genes, pET-9a-Laci_13-LAH, pET-9a-Lamy_13-LAH, pET-9a-Lhel_13-LAH, pET-9a-Lgal_13-LAH, pET-9a-Lcri_13-LAH, pET-9a-Lkef_13-LAH, pET-9a-Lint_13-LAH, pET-9a-Lham_13-LAH, pET-9a-Lgas_13-LAH, pET-9a-Pcla_13-LAH, pET-9a-Lrum_13-LAH, pET-9a-Sinf_13-LAH, pET-9a-Smut_13-LAH, and pET-9a-Sequ_13-LAH were obtained. For an abbreviated name of each gene, see Table 2.

<Construction of Expression Plasmid pET-22b(+)Km$^R$>

A plasmid pET-22b(+)Km$^R$ for expressing the genes of various 13-LAH was constructed by the following procedure. First, a drug marker of pET-22b(+) (from Novagen (Merck Millipore), Product Number 69744-3CN) was changed from ampicillin resistance to kanamycin resistance. A gene fragment of λattL-Km$^R$-λattR (International Publication No. 2008/090770) was amplified by PCR (PrimeSTAR GXL (registered trade name) DNA polymerase, 98° C. for 10 seconds, 55° C. for 15 seconds and 68° C. for 120 seconds, 30 cycles) using genomic DNA containing λattL-Km$^R$-λattR as a template and using primers Km-pET-F (SEQ ID NO:29) and Km-pET-R (SEQ ID NO:30). The obtained PCR product was purified using Wizard (registered trade name) SV Gel and PCR Clean-UP system (from Promega, Product Number A9281) to obtain a DNA fragment of a kanamycin resistant gene. Subsequently, a full length plasmid excluding an ampicillin resistant gene was amplified by PCR (PrimeSTAR GXL (registered trade name) DNA polymerase, 98° C. for 10 seconds, 54° C. for 15 seconds and 68° C. for 240 seconds, 40 cycles) using pET-22b(+) as the template and using primers pET22-Km-invF (SEQ ID NO:31) and pET22-Km-invR (SEQ ID NO:32). The obtained PCR product was purified using Wizard (registered trade name) SV Gel and PCR Clean-UP system (from Promega, Product Number A9281) as with above to obtain a DNA fragment of pET-22b(+). The kanamycin resistant gene was ligated to the gene fragment of pET-22b(+) using In-Fusion (registered trade name) HD cloning Kit (from Clontech, Product Number 639648) to use for transformation of *E coli* JM strain. The transformed *E. coli* strain was inoculated in LB agar medium (10 g/L NaCl, 10 g/L Bacto tryptone, 5 g/L Bacto yeast extract, Bacto agar 20 g/L), which was then cultured at 37° C. overnight to obtain transformants. Using the emerging transformant, colony PCR was performed using the primers represented by Km-pET-F (SEQ ID NO:29) and Km-pET-R (SEQ ID NO:30) to obtain pET-22b(+)-Km$^R$ where the drug marker of pET-22b(+) was changed from the ampicillin resistance to the kanamycin resistance. Sequences of the primers used for construction of pET-22b(+)-Km$^R$ are shown in Table 3.

TABLE 3

List of primers used for construction of pET-22b(+)Km$^R$

| Primer name | Nucleotide sequence (5'-3') | Nucleotide sequence number |
|---|---|---|
| Km-pET-F | 5'TGAAAAAGGAAGAGTTGAAGCCTGCTTTTT TATACTAAGTTGGC 3' | SEQ ID NO: 29 |
| Km-pET-R | 5'AACTTGGTCTGACAGCGCTCAAGTTAGTATA AAAAAGCTGAACGA 3' | SEQ ID NO: 30 |

TABLE 3-continued

List of primers used for construction of pET-22b(+)Km$^R$

| Primer name | Nucleotide sequence (5'-3') | Nucleotide sequence number |
|---|---|---|
| pET22-Km-invF | 5'ACTCTTCCTTTTTCAATATTATTGAAGC 3' | SEQ ID NO: 31 |
| pET22-Km-invR | 5'CTGTCAGACCAAGTTTACTCATATATAC 3' | SEQ ID NO: 32 |

<Construction of Plasmid for Expression of Various 13-LAH Utilizing pET-22b(+)-Km$^R$> pET-22b(+)-Km$^R$ was digested with restriction enzymes NdeI and EcoRI and then run on agarose gel electrophoresis. Subsequently, a DNA fragment of pET-22b(+)-Km$^R$ was cut out from the gel to obtain a purified DNA fragment using Wizard (registered trade name) SV Gel and PCR Clean-UP system (from Promega, Product Number A9281). A gene fragment of each 13-LAH was amplified by PCR (PrimeSTAR GXL (registered trade name), 98° C. for 10 seconds, 55° C. for 15 seconds and 68° C. for 120 seconds, 30 cycles) using the combination of primers shown in Table 4 and a plasmid to become the template. For example, a gene fragment of 13-LAH from *Lactobacillus amylovorus* (Lamy_13-LAH) was amplified by PCR using pET-9a-Lamy_13-LAH as the template DNA and the combination of primers represented by 13LAH1234578_F (SEQ ID NO:33) and 13LAH138_R (SEQ ID NO:34). The template DNA and the combinations of primers used for PCR are shown in Table 4. Subsequently, each resulting PCR product was purified using Wizard (registered trade name) SV Gel and PCR Clean-UP system (from Promega, Product Number A9281) to obtain a purified DNA fragment of each 13-LAH gene. The above purified DNA fragment of pET-22b(+)Km$^R$ was ligated to the purified DNA fragment of each 13-LAH gene using In-Fusion (registered trade name) HD cloning Kit (from Clontech, Product Number 639648), and the obtained DNA fragment was used to transform *E. coli* JM109 strain. Subsequently, microbial cells were inoculated to the LB agar medium containing 50 mg/mL kanamycin, and then cultured at 37° C. overnight to obtain transformants. Using the emerging transformant, colony PCR was performed using the combination of primers represented by T7P-F (nucleotide sequence: 5'TAATACGACTCAC-TATAGGG3' (SEQ ID NO:61) and T7T-R (nucleotide sequence: 5'GCTAGTTATTGCTCAGCGG3' (SEQ ID NO:62) to obtain an expression plasmid where each 13-LAH was introduced into pET-22b(+)Km$^R$.

TABLE 4

List of constructed plasmids and primers and templates used at that time

| Constructed plasmid | Primer name | Template DNA | Nucleotide sequence (5'-3') | Nucleotide sequence Number |
|---|---|---|---|---|
| Table 4-1 | | | | |
| pET-22b(+)Km$^R$-Lamy_13-LAH | 13LAH1234578_F | pET-9a-Lamy_13-LAH | 5'AAGAAGGAGATATACATATGCACTACAGCAACGGTAAC3' | SEQ ID NO: 33 |
| | 13LAH138_R | | 5'TGTCGACGGAGCTCGAATTCTTAGATCAGTTTATATTTCT3' | SEQ ID NO: 34 |
| pET-22b(+)Km$^R$-Lhel_13-LAH | 13LAH1234578_F | pET-9a-Lhel_13-LAH | 5'AAGAAGGAGATATACATATGCACTACAGCAACGGTAAC3' | SEQ ID NO: 35 |
| | 13LAH_R | | 5'TGTCGACGGAGCTCGAATTCTTAAATCAGTTTATATTCCT3' | SEQ ID NO: 36 |
| pET-22b(+)Km$^R$-Lgal_13-LAH | 13LAH1234578_F | pET-9a-Lgal_13-LAH | 5'AAGAAGGAGATATACATATGCACTACAGCAACGGTAAC3' | SEQ ID NO: 37 |
| | 13LAH138_R | | 5'TGTCGACGGAGCTCGAATTCTTAGATCAGTTTATATTTCT3' | SEQ ID NO: 38 |
| pET-22b(+)Km$^R$-Lcri_13-LAH | 13LAH1234578_F | pET-9a-Lcri_13-LAH | 5'AAGAAGGAGATATACATATGCACTACAGCAACGGTAAC3' | SEQ ID NO: 39 |
| | 13LAH45_R | | 5'TGTCGACGGAGCTCGAATTCTTAAATCAGTTTATATTTCT3' | SEQ ID NO: 40 |
| pET-22b(+)Km$^R$-Lkef_13- | 13LAH1234578_F | pET-9a-Lkef_13-LAH | 5'AAGAAGGAGATATACATATGCACTACAGCAACGGTAAC3' | SEQ ID NO: 41 |

TABLE 4-continued

List of constructed plasmids and primers and templates used at that time

| Constructed plasmid | Primer name | Template DNA | Nucleotide sequence (5'-3') | Nucleotide sequence Number |
|---|---|---|---|---|
| LAH | 13LAH45_R | | 5'TGTCGACGGAGCTCGAATTCTTAAATCAGTTTATATTTCT3' | SEQ ID NO: 42 |
| pET-22b(+)Km$^R$-Lint_13-LAH | 13LAH6_F<br>13LAH6_R | pET-9a-Lint_13-LAH | 5'AAGAAGGAGATATACATATGCTGGGTCTGACCAAGGAA3'<br>5'TGTCGACGGAGCTCGAATTCTTACATCAGTTTATACTGCT3' | SEQ ID NO: 43<br>SEQ ID NO: 44 |
| pET-22b(+)Km$^R$-Lham_13-LAH | 13LAH1234578_F<br>13LAH7_R | pET-9a-Lham_13-LAH | 5'AAGAAGGAGATATACATATGCACTACAGCAACGGTAAC3'<br>5'TGTCGACGGAGCT?CGAATTCTTACATCAGACGATATTCTT3' | SEQ ID NO: 45<br>SEQ ID NO: 46 |
| pET-22b(+)Km$^R$-Lgas_13-LAH | 13LAH1234578_F<br>13LAH138_R | pET-9a-Lgas_13-LAH | 5'AAGAAGGAGATATACATATGCACTACAGCAACGGTAAC3'<br>5'TGTCGACGGAGCTCGAATTCTTAGATCAGTTTATATTTCT3' | SEQ ID NO: 47<br>SEQ ID NO: 48 |
| pET-22b(+)Km$^R$-Pcla_13-LAH | 13LAH9_F<br>13LAH9_R | pET-9a-Pcla_13-LAH | 5'AAGAAGGAGATATACATATGTACTATAGCAACGGTAAC3'<br>5'TGTCGACGGAGCTCGAATTCTTACAGCAGGTGCGCGTTTT3' | SEQ ID NO: 49<br>SEQ ID NO: 50 |
| pET-22b(+)Km$^R$-Lrum_13-LAH | 13LAH10111213_F<br>13LAH10_R | pET-9a-Lrum_13-LAH | 5'AAGAAGGAGATATACATATGTACTATAGCAACGGCAAC3'<br>5'TGTCGACGGAGCTCGAATTCTTATTTGATCACGTGATACT3' | SEQ ID NO: 51<br>SEQ ID NO: 52 |

Table 4-2

| Constructed plasmid | Primer name | Template DNA | Nucleotide sequence (5'-3') | Nucleotide sequence Number |
|---|---|---|---|---|
| pET-22b(+)Km$^R$-Sinf_13-LAH | 13LAH10111213_F<br>13LAH1113_R | pET-9a-Sinf_13-LAH | 5'AAGAAGGAGATATACATATGTACTATAGCAACGGCAAC3'<br>5'TGTCGACGGAGCTCGAATTCTTACAGCAGGTGATACTCCT3' | SEQ ID NO: 51<br>SEQ ID NO: 54 |
| pET-22b(+)Km$^R$-Smut_13-LAH | 13LAH10111213_F<br>13LAH12_R | pET-9a-Smut_13-LAH | 5'AAGAAGGAGATATACATATGTACTATAGCAACGGCAAC3'<br>5'TGTCGACGGAGCTCGAATTCTTAAATCAGGTGATAATCTT3' | SEQ ID NO: 55<br>SEQ ID NO: 56 |
| pET-22b(+)Km$^R$-Sequ_13-LAH | 13LAH10111213_F<br>13LAH1113_R | pET-9a-Sequ_13-LAH | 5'AAGAAGGAGATATACATATGTACTATAGCAACGGCAAC3'<br>5'TGTCGACGGAGCTCGAATTCTTACAGCAGGTGATACTCCT3' | SEQ ID NO: 57<br>SEQ ID NO: 58 |
| pET-22b(+)Km$^R$-Laci_13-LAH | 13LAHE14_F<br>13LAHE14_R | pET-9a-Laci_13-LAH | 5'AAGAAGGAGATATACATATGCACTACAGCAGCGGCAA3'<br>5'TGTCGACGGAGCTCGAATTCTTAAACCAGCTTGTATTTCT3' | SEQ ID NO: 59<br>SEQ ID NO: 60 |

Example 2: Study on Producing 13-HOD from Linolenic Acid Using E. coli that Expresses Each 13-LAH <Construction of E. coli BLR(DE3) Strain that Expresses Each 13-LAH>

Electrocompetent cells were prepared from BLR(DE3) strain (from Merck Millipore, Product Number 69053) according to standard methods, and used to introduce each pET-22b(+)Km$^R$-XXXX_13-LAH (XXXX denotes each abbreviated name. see Table 4) therein by an electroporation method. Obtained transformants were inoculated to LB agar medium containing 50 mg/mL kanamycin, and then cultured at 37° C. overnight to obtain a transformant BLR(DE3)/pET-22b(+)Km$^R$-XXXX_13-LAH strain.

<Study on Producing 13-HOD from Linolenic Acid Using BLR(DE3)/pET-22b(+)Km$^R$-XXXX_13-LAH Strain>

BLR(DE3)/pET-22b(+)Km$^R$-XXXX_13-LAH strain obtained above was inoculated to 3 mL of SOC medium in a test tube, and cultured with shaking at 120 rpm and 37° C. for 16 to 24 hours to obtain precultured medium A. A composition of the SOC medium and a preparation method thereof are shown in Table 5. 0.5 mL of the precultured medium A was inoculated to 50 mL of the SOC medium in a 500 mL shaking flask, and cultured with shaking at 120 rpm and 37° C. for 2 hours. Subsequently, the culture temperature was lowered to 16° C. and 1 mM isopropyl-β-thiogalactopyranoside (IPTG) was added to induce the expression of a 13-LAH protein. After adding IPTG, the culture was continued for additional 22 to 24 hours, and 4 mL of the obtained culture medium was centrifuged to collect microbial cells. Subsequently, the microbial cells were washed twice with 0.8 M NaCl to use for a conversion reaction. The obtained microbial cells were suspended in 1 mL of a conversion reaction solution in 14 mL Falcon tube, and cultured with shaking at 120 rpm and 37° C. for 5 hours. A composition of the conversion reaction solution and a preparation method thereof are shown in Table 6.

TABLE 5

Composition of conversion reaction solution and preparation method thereof

| Composition | Amount of component |
|---|---|
| Stock solution A | 960 mL |
| 1M CaCl$_2$ | 10 mL |
| 1M MgSO$_4$ | 10 mL |
| 1M Glucose | 20 mL |

A stock solution A was prepared by the following procedure. 0.5 g of NaCl, 20 g of Bacto tryptone, 5 g of Bacto yeast extract, 0.186 g of KCl were dissolved in purified water, then diluted to 960 mL, and adjusted pH to 7.0 with NaOH. Subsequently the solution was sterilized by autoclave at 120° C. for 15 minutes. Solutions of 1M CaCl$_2$, 1 M MgSO$_4$ and 1 M glucose were prepared, respectively, and sterilized by filtrating through a 0.22 μm filter. 10 mL of 1M CaCl$_2$, 10 mL of 1 M MgSO$_4$ and 20 mL of 1 M glucose were added to 960 mL of cooled stock solution A, and then kanamycin at a final concentration of 50 mg/mL was added thereto to use as SOC medium.

TABLE 6

Composition of conversion reaction solution and preparation method thereof.

| Composition | Amount of component |
|---|---|
| Citrate/phosphate buffer (pH 6.0) | 100 mL |
| Tween20 | Final concentration 0.25 wt % |
| Linoleic acid | Final concentration 50 g/L |

Citrate/phosphate buffer was prepared by mixing 17.9 mL of 1 M citrate solution and 32.1 mL of 0.2 M disodium hydrogen phosphate-12 hydrate solution followed by adjusting pH to 6.0 with NaOH. Subsequently, the mixture was diluted to 100 mL with purified water, and sterilized by the autoclave at 120° C. for 15 minutes. Then, Tween 20 and linolenic acid sterilized under the same condition were added at final concentrations of 0.25 wt % and 50 g/L, respectively.

<Method of Extracting Fatty Acids from Reaction Solution and Component Analysis by GC-MS>

Extracts of fatty acids in a reaction solution were analyzed by the following procedure. 0.2 mL of the reaction solution after the conversion was placed in a 1.5 mL microtube with lock, then 0.6 mL of ethyl acetate was added thereto, and the mixture was mixed on a vortex for 10 seconds. This ethyl acetate solution was centrifuged at 15,000 rpm at 25° C. for 10 minutes, and an ethyl acetate layer at an upper layer was obtained as an analysis sample. Subsequently, in order to subject the fatty acids in the analysis sample to a silylation reaction, 60 μL of a derivatization reagent (BSA+TMCS, 5:1 (from SUPELCO, Product Number 33018) was added to 30 μL of the analysis sample, and the mixture was left standing at room temperature for 2 hours. This was used for GC-MS analysis. A condition of GC-MS analysis is shown below.

<GC-MS>

Apparatus: Agilent 5975C MSD and 7890A GC, autosampler: Gerstel MPS Autosampler (GC)

Injection amount: 1 μL, injection method: split 20:1, inlet temperature: 230° C., column: Agilent DB-1 ms, 30 m, 0.25 mm, 0.25 μm (Product Number 122-0132), column temperature program: starting at 25° C., rising temperature up to 160° C. at 25° C./min, then rising temperature up to 280° C. (kept for 2.5 min) at 5° C./min, carrier gas pressure: 9.954 psi (MS)

Interface temperature: 280° C., ion source temperature: 230° C., quadrupolar temperature: 150° C., ionization mode: EI: (electron energy: 70 eV), tuning: Etune, start time: 4 minutes, measurement mode: scan (20 to 500 m/Z).

Figure 2:
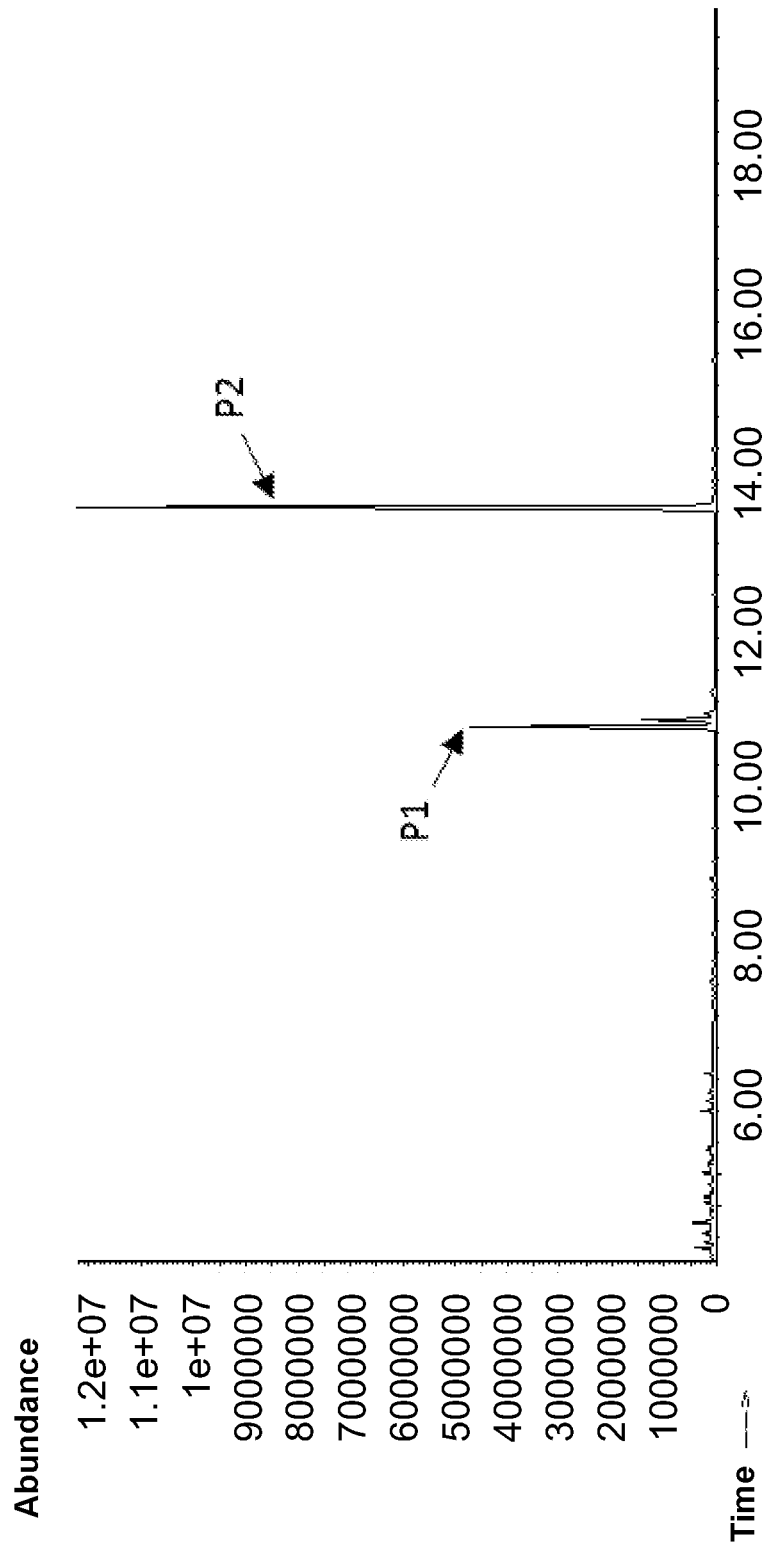
FIG. 2 shows an MS chromatogram obtained from a reaction solution of BLR(DE3)/pET-22b(+)Km$^R$-Laci_13-LAH strain.
Figure 3:
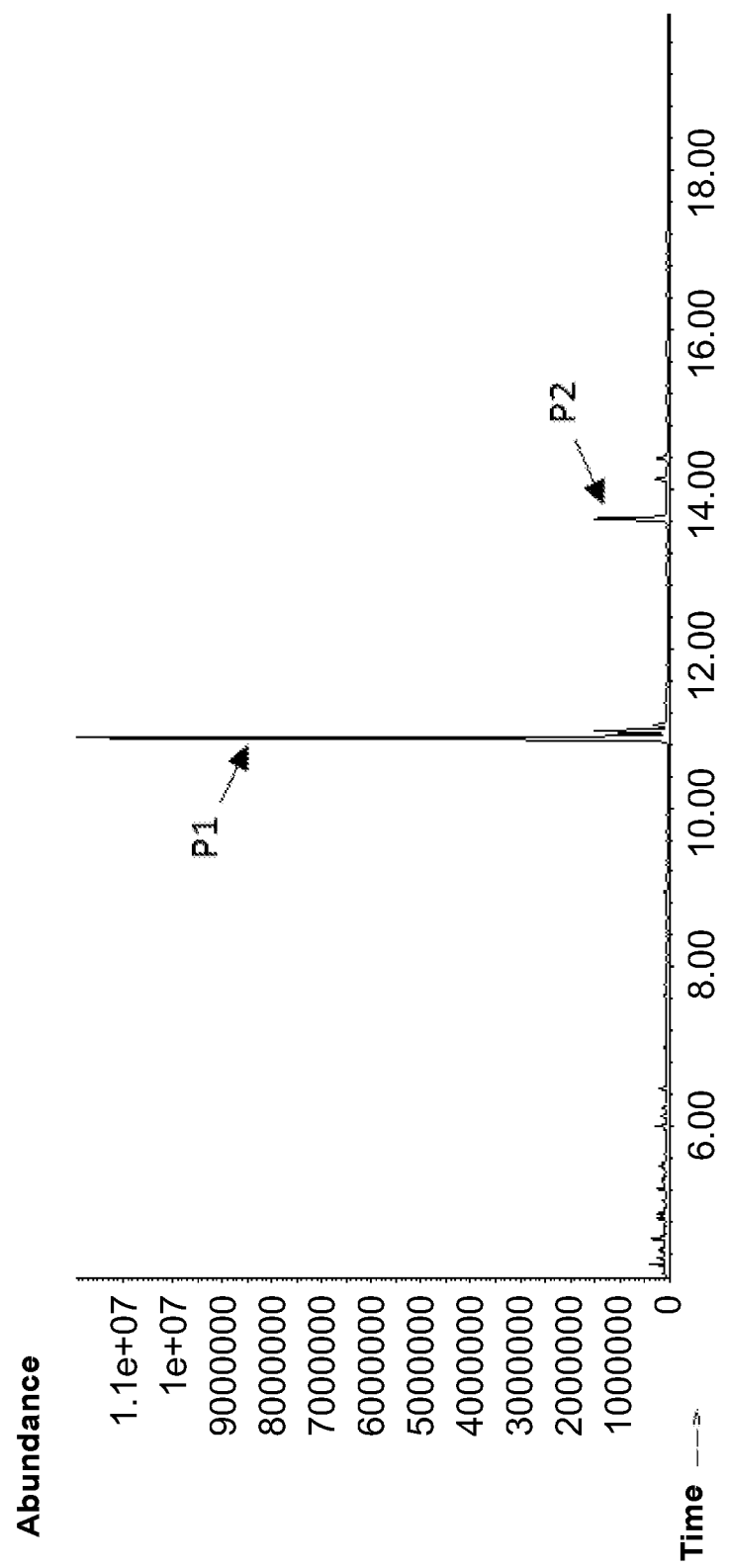
FIG. 3 shows an MS chromatogram obtained from a reaction solution of BLR(DE3)/pET-22b(+)Km$^R$-Lamy_13-LAH strain.
Figure 4:
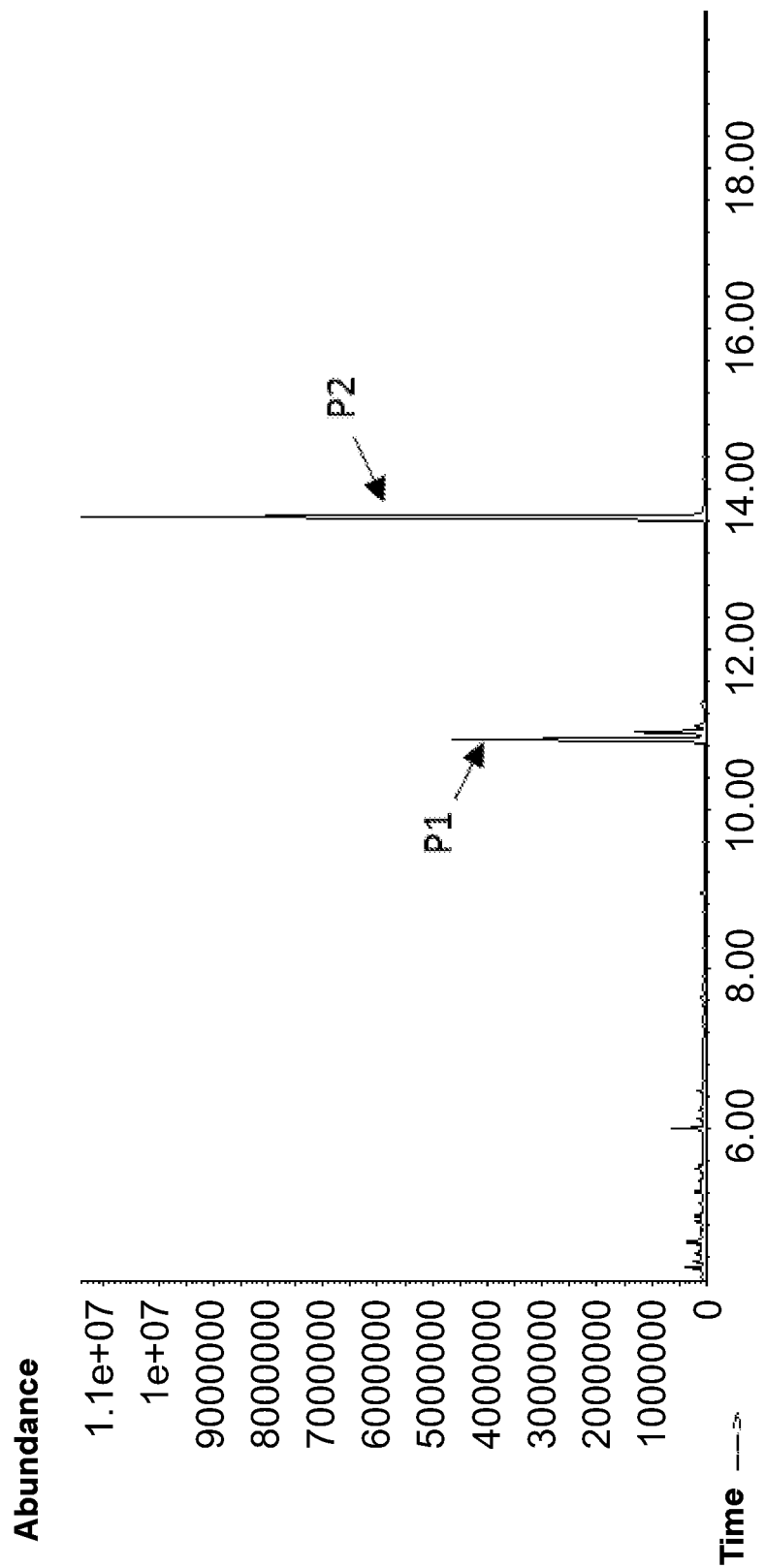
FIG. 4 shows an MS chromatogram obtained from a reaction solution of BLR(DE3)/pET-22b(+)Km$^R$-Lhel_13-LAH strain.
Figure 5:
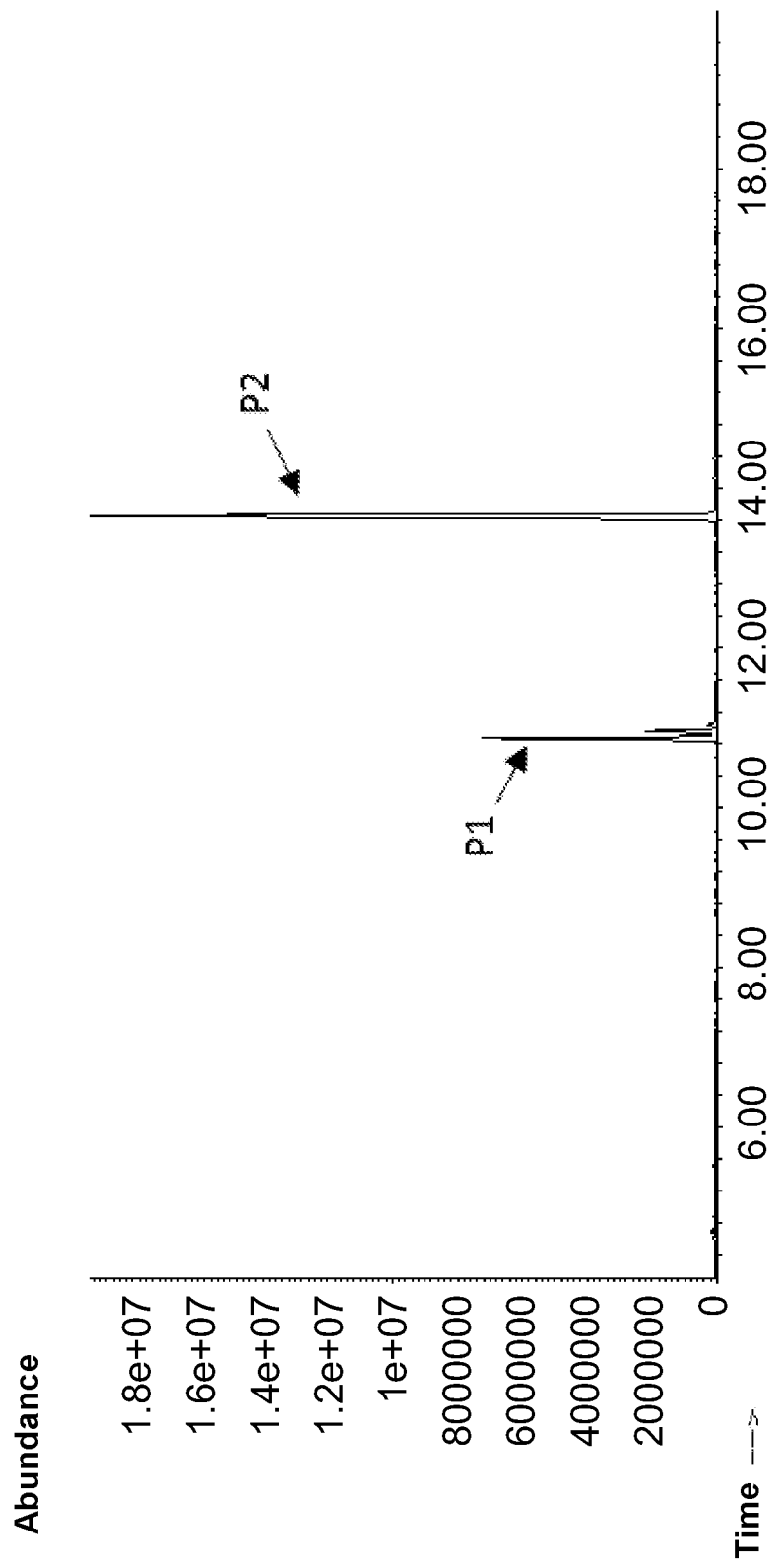
FIG. 5 shows an MS chromatogram obtained from a reaction solution of BLR(DE3)/pET-22b(+)Km$^R$-Lgal_13-LAH strain.
Figure 6:
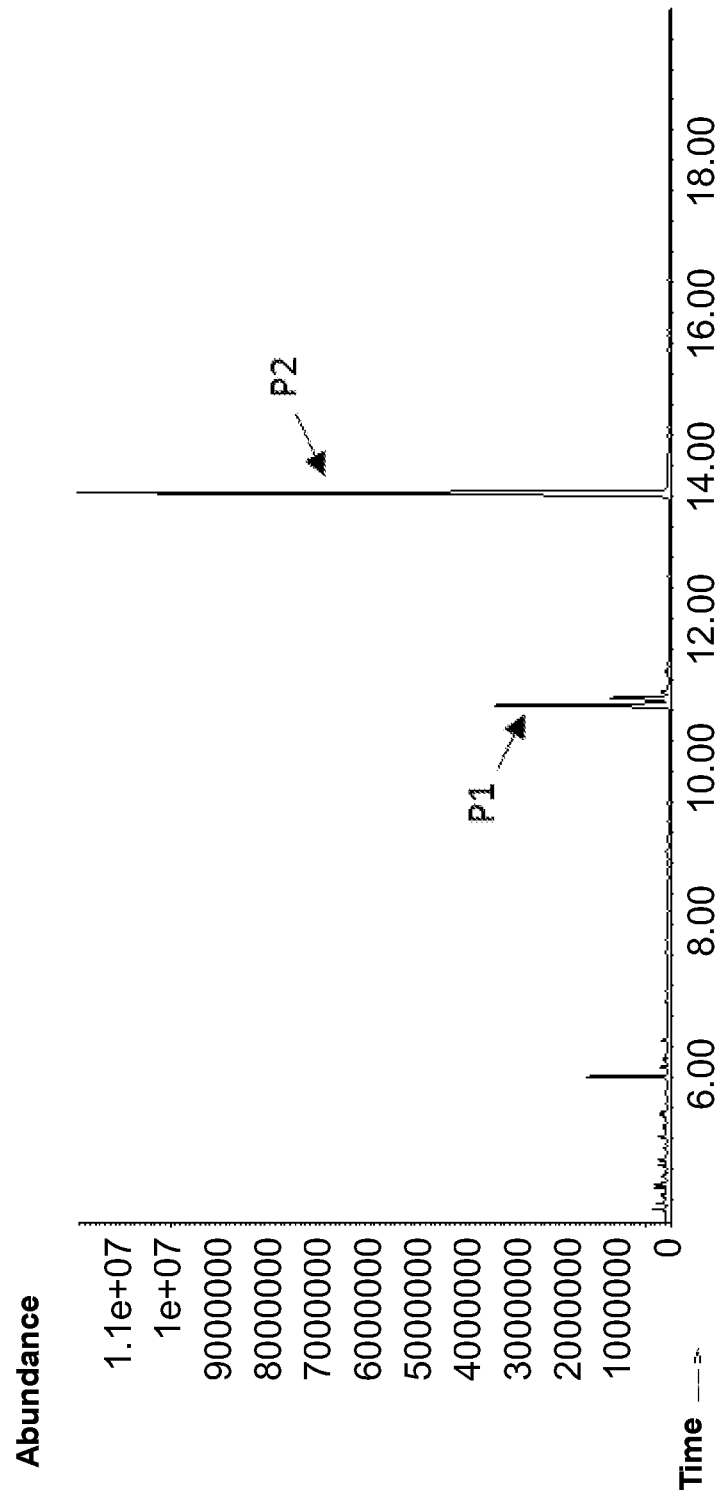
FIG. 6 shows an MS chromatogram obtained from a reaction solution of BLR(DE3)/pET-22b(+)Km$^R$-Lcri_13-LAH strain.
Figure 7:
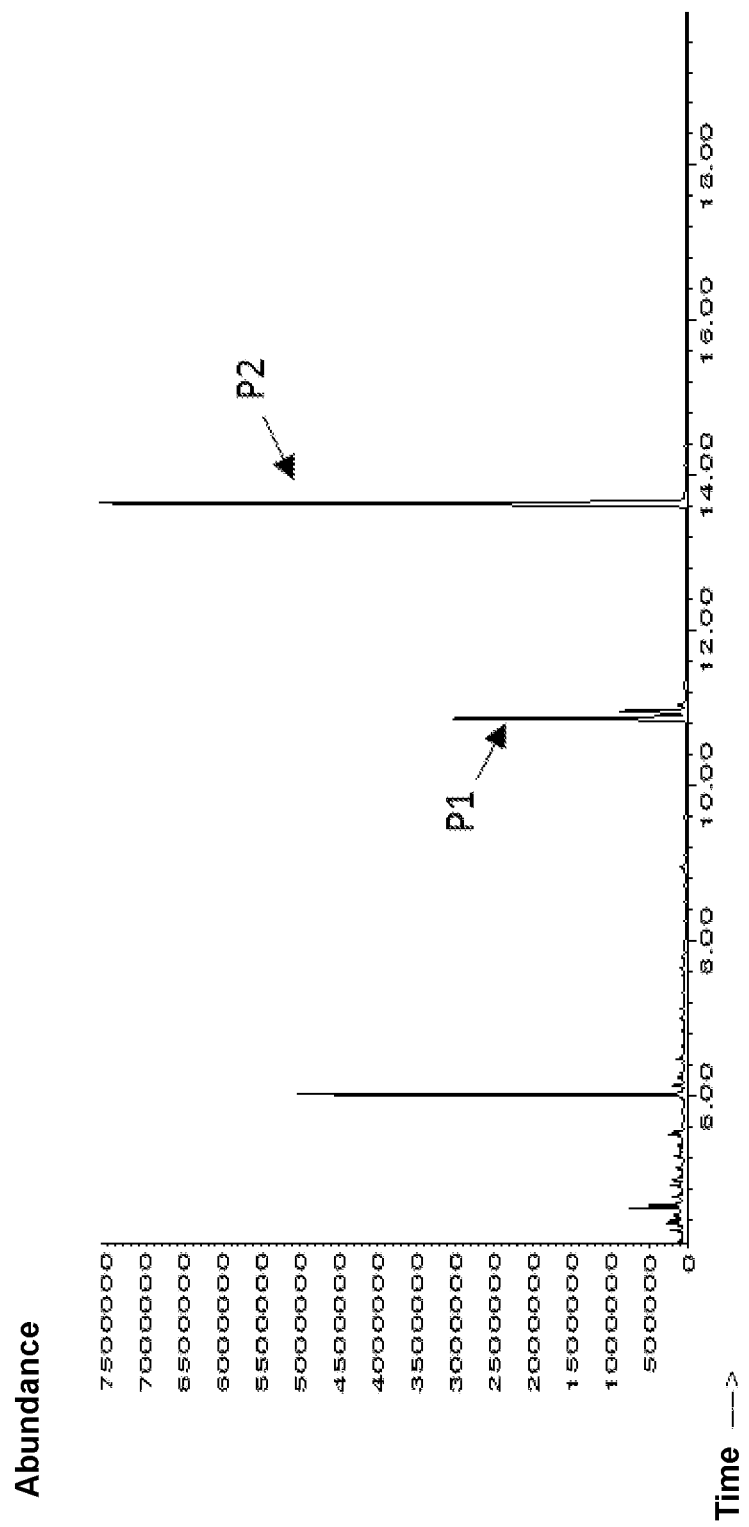
FIG. 7 shows an MS chromatogram obtained from a reaction solution of BLR(DE3)/pET-22b(+)Km$^R$-Lkef_13-LAH strain.
Figure 8:
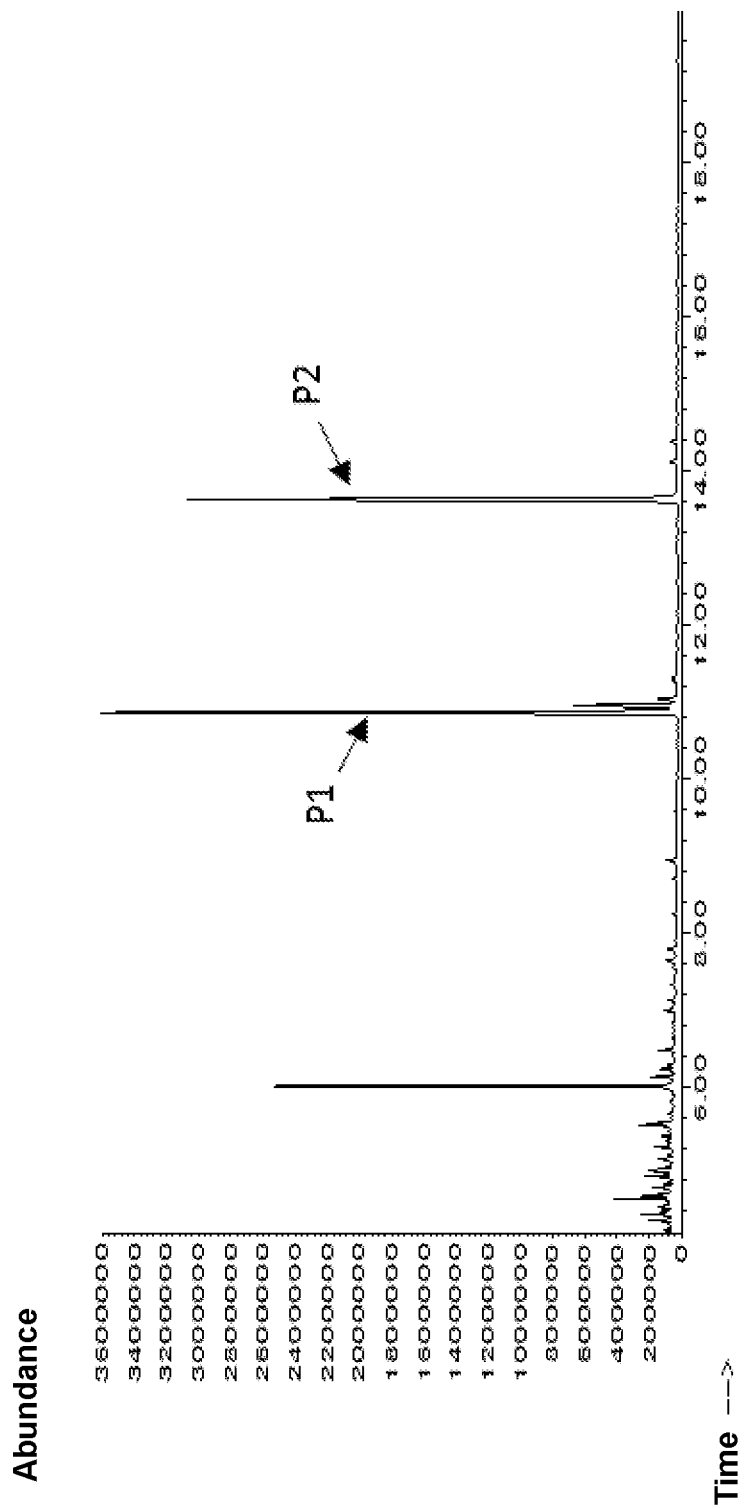
FIG. 8 shows an MS chromatogram obtained from a reaction solution of BLR(DE3)/pET-22b(+)Km$^R$-Lint_13-LAH strain.
Figure 9:
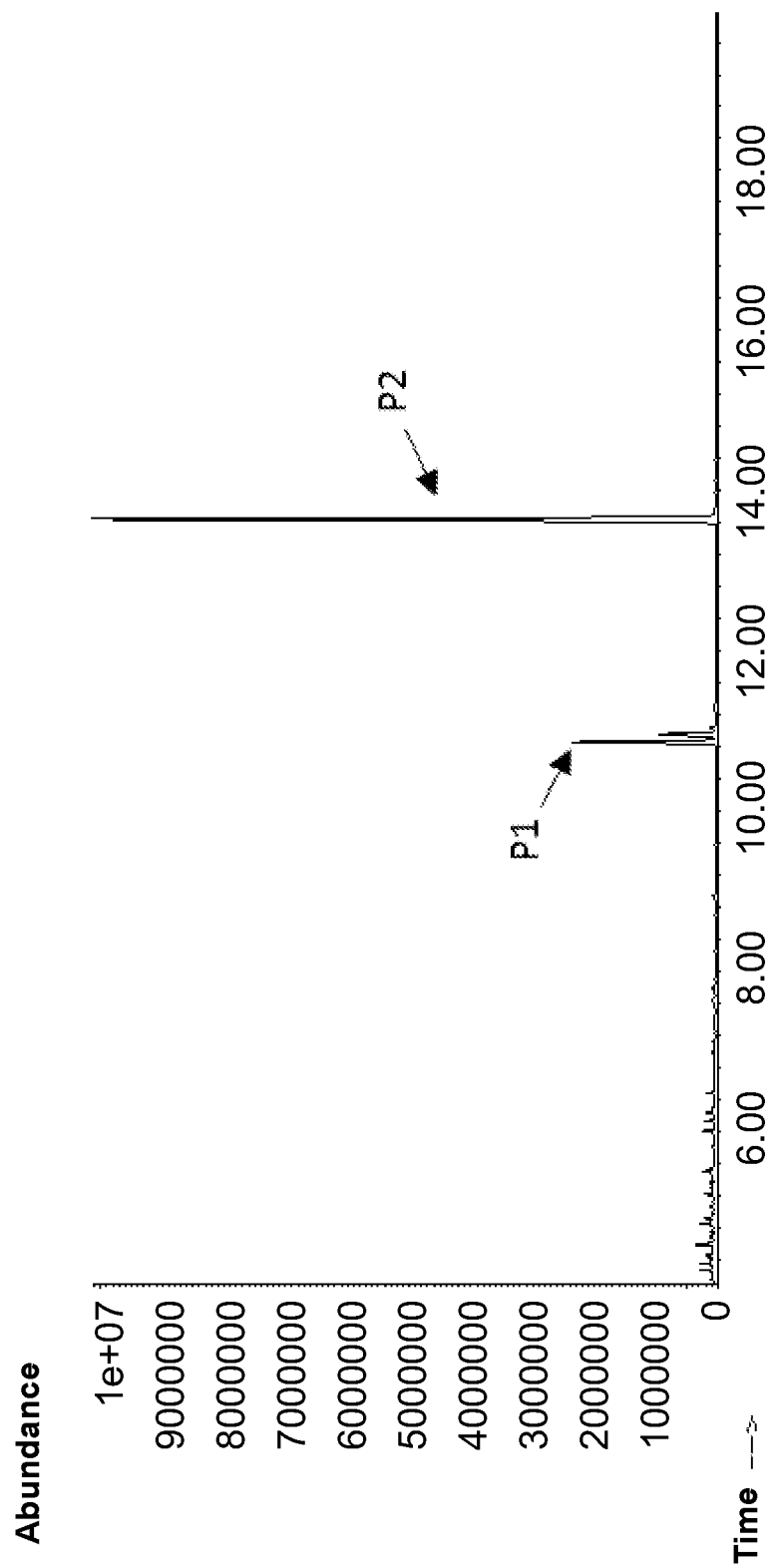
FIG. 9 shows an MS chromatogram obtained from a reaction solution of BLR(DE3)/pET-22b(+)Km$^R$-Lham_13-LAH strain.
Figure 10:
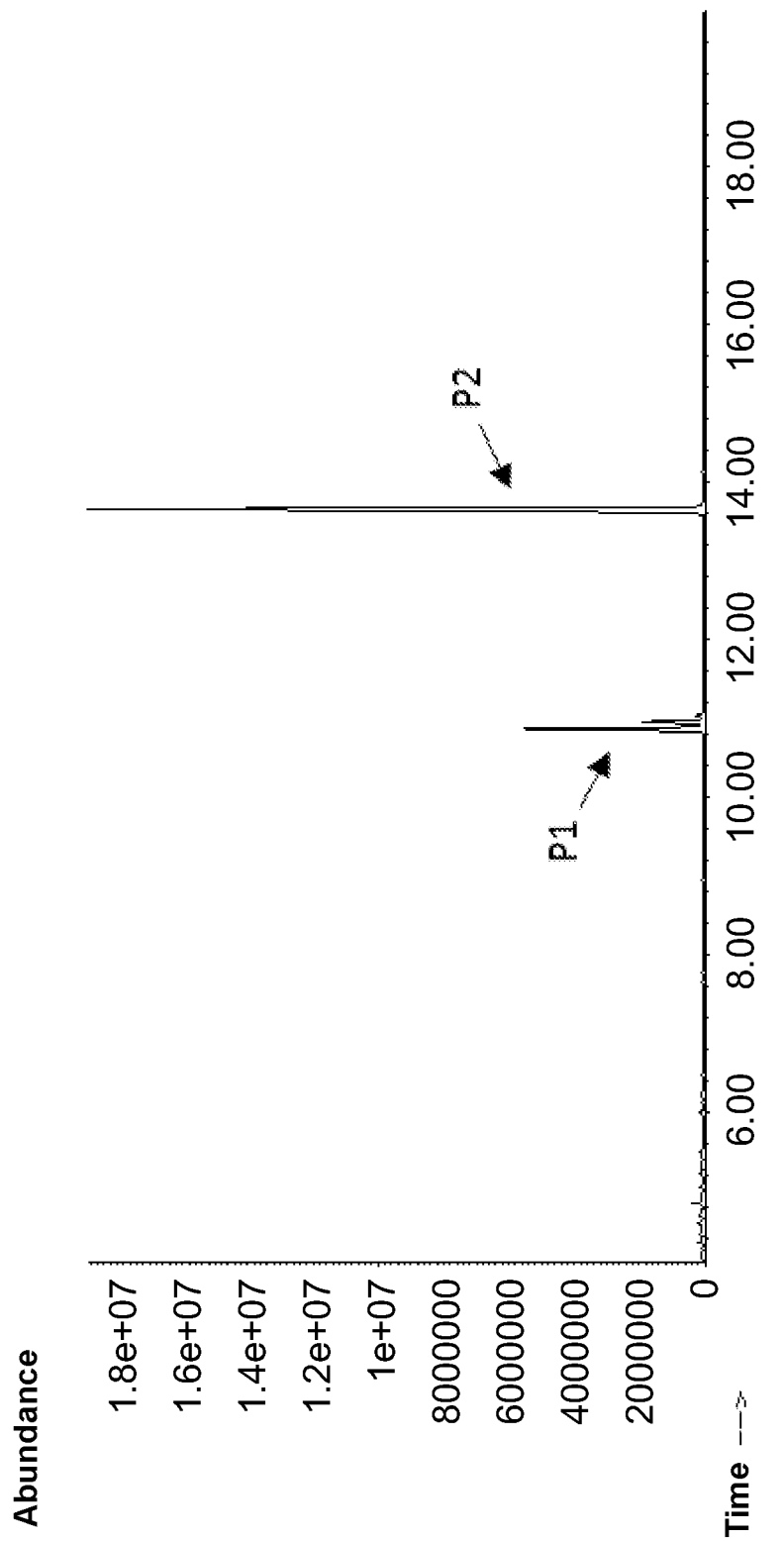
FIG. 10 shows an MS chromatogram obtained from a reaction solution of BLR(DE3)/pET-22b(+)Km$^R$-Lgas_13-LAH strain.
Figure 11:
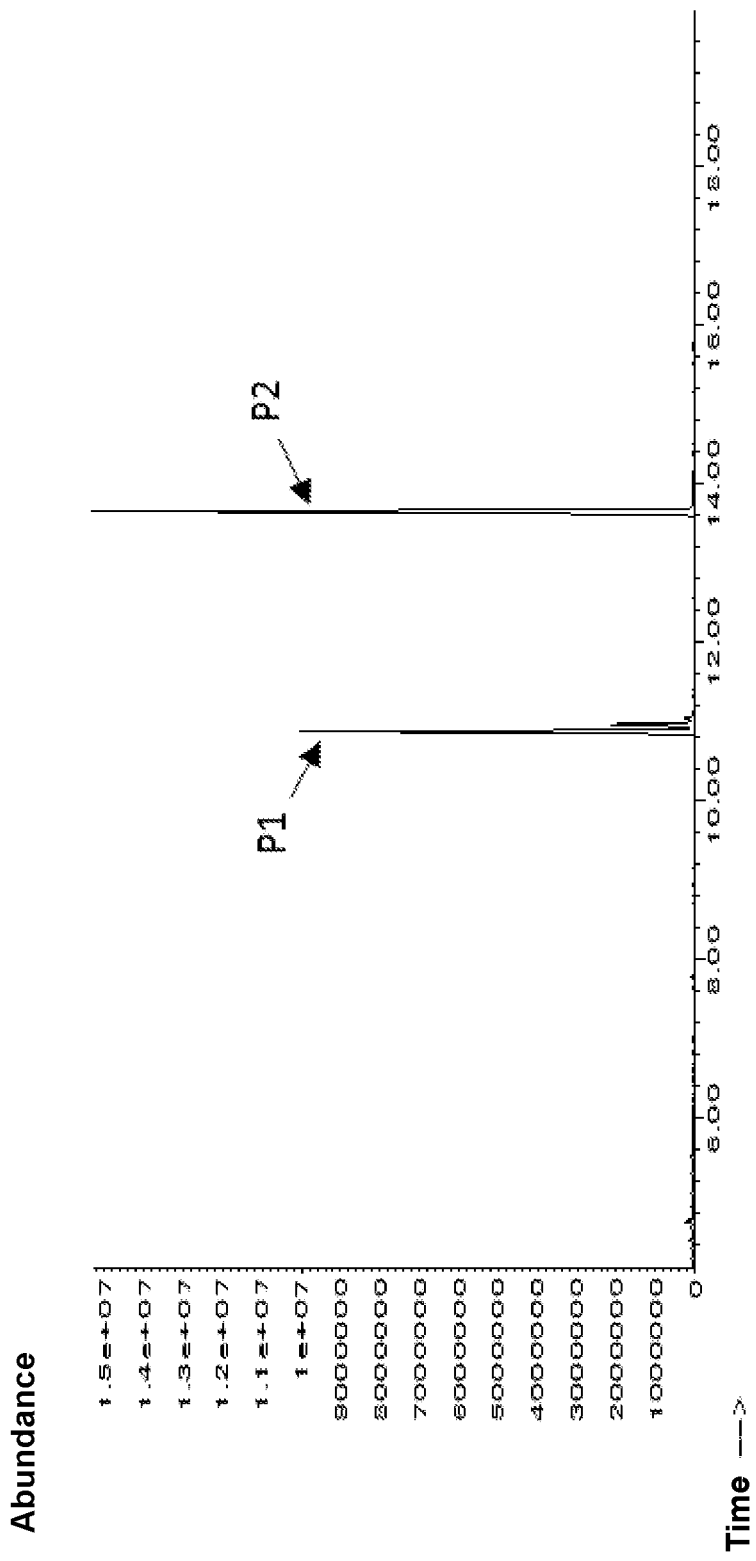
FIG. 11 shows an MS chromatogram obtained from a reaction solution of BLR(DE3)/pET-22b(+)Km$^R$-Pcla_13-LAH strain.
Figure 12:
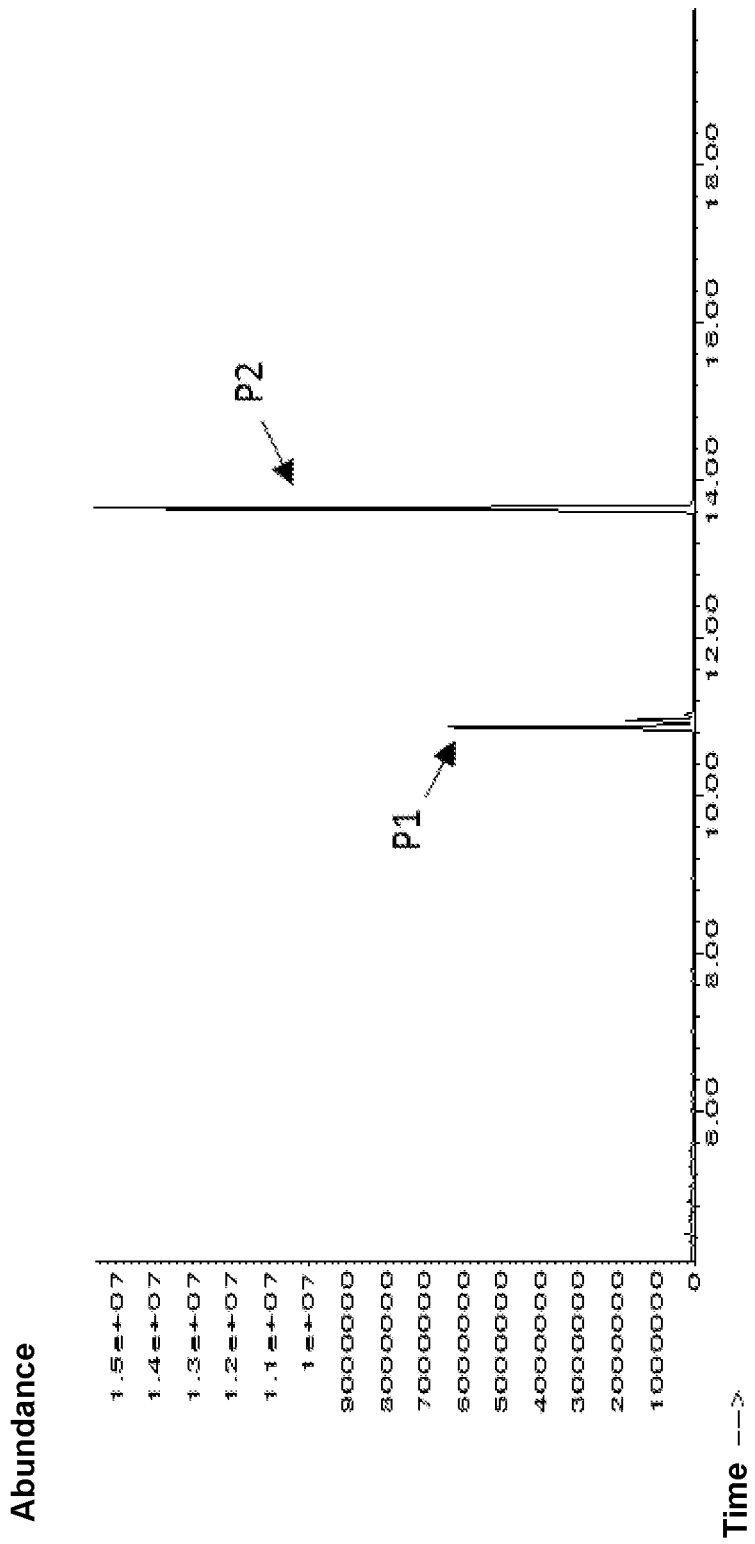
FIG. 12 shows an MS chromatogram obtained from a reaction solution of BLR(DE3)/pET-22b(+)Km$^R$-Lrum_13-LAH strain.
Figure 13:
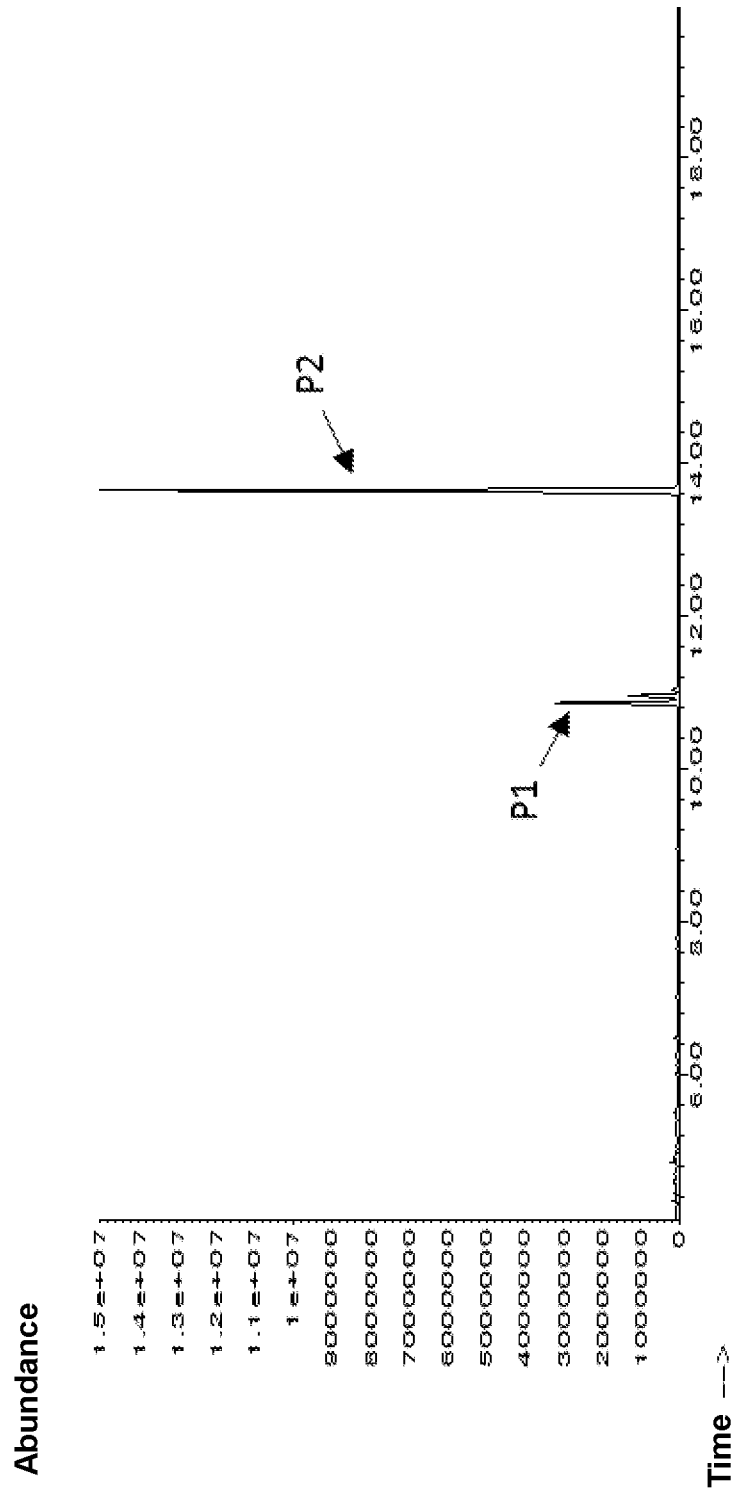
FIG. 13 shows an MS chromatogram obtained from a reaction solution of BLR(DE3)/pET-22b(+)Km$^R$-Sinf_13-LAH strain.
Figure 14:
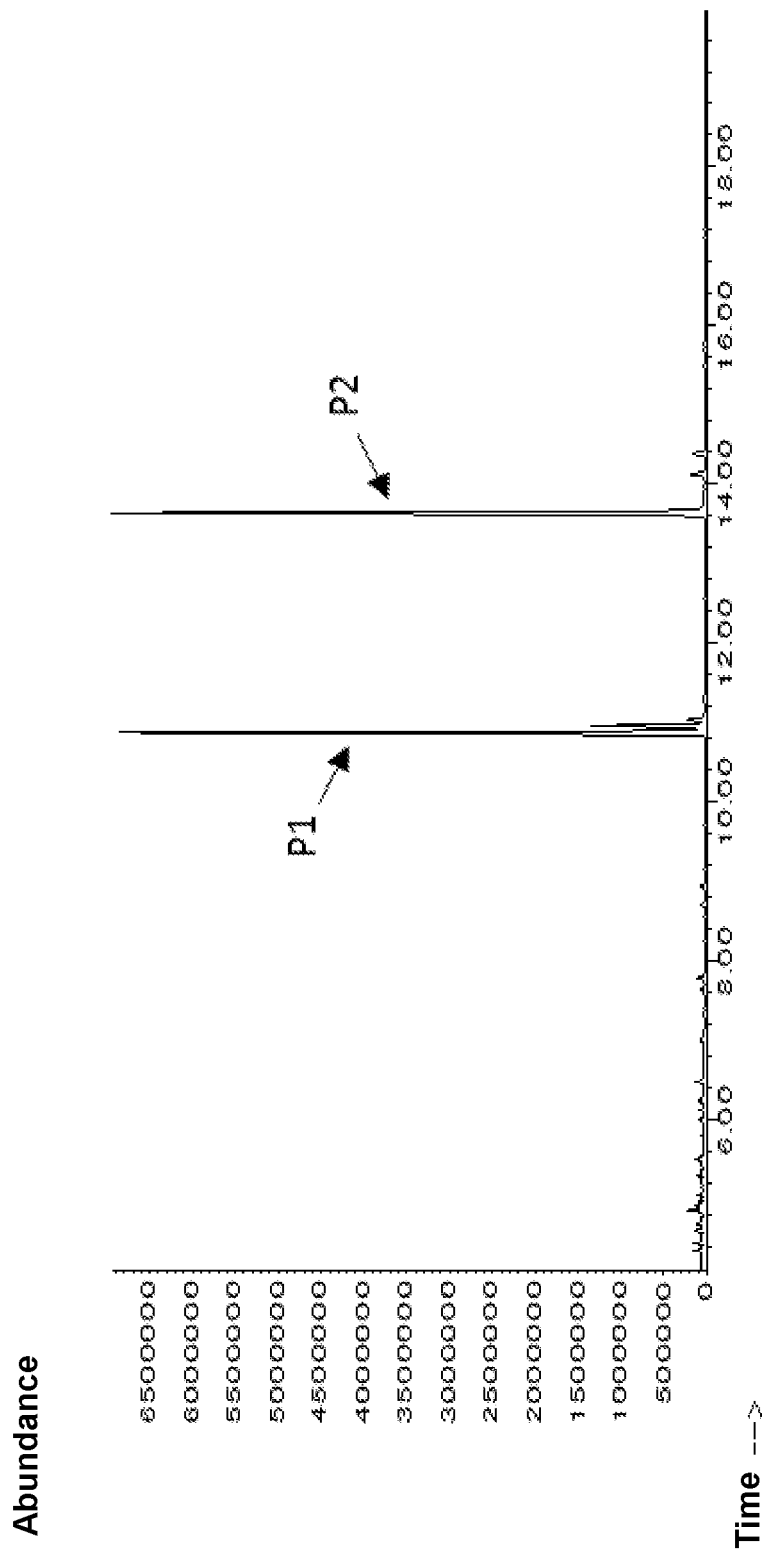
FIG. 14 shows an MS chromatogram obtained from a reaction solution of BLR(DE3)/pET-22b(+)Km$^R$-Smut_13-LAH strain.
Figure 15:
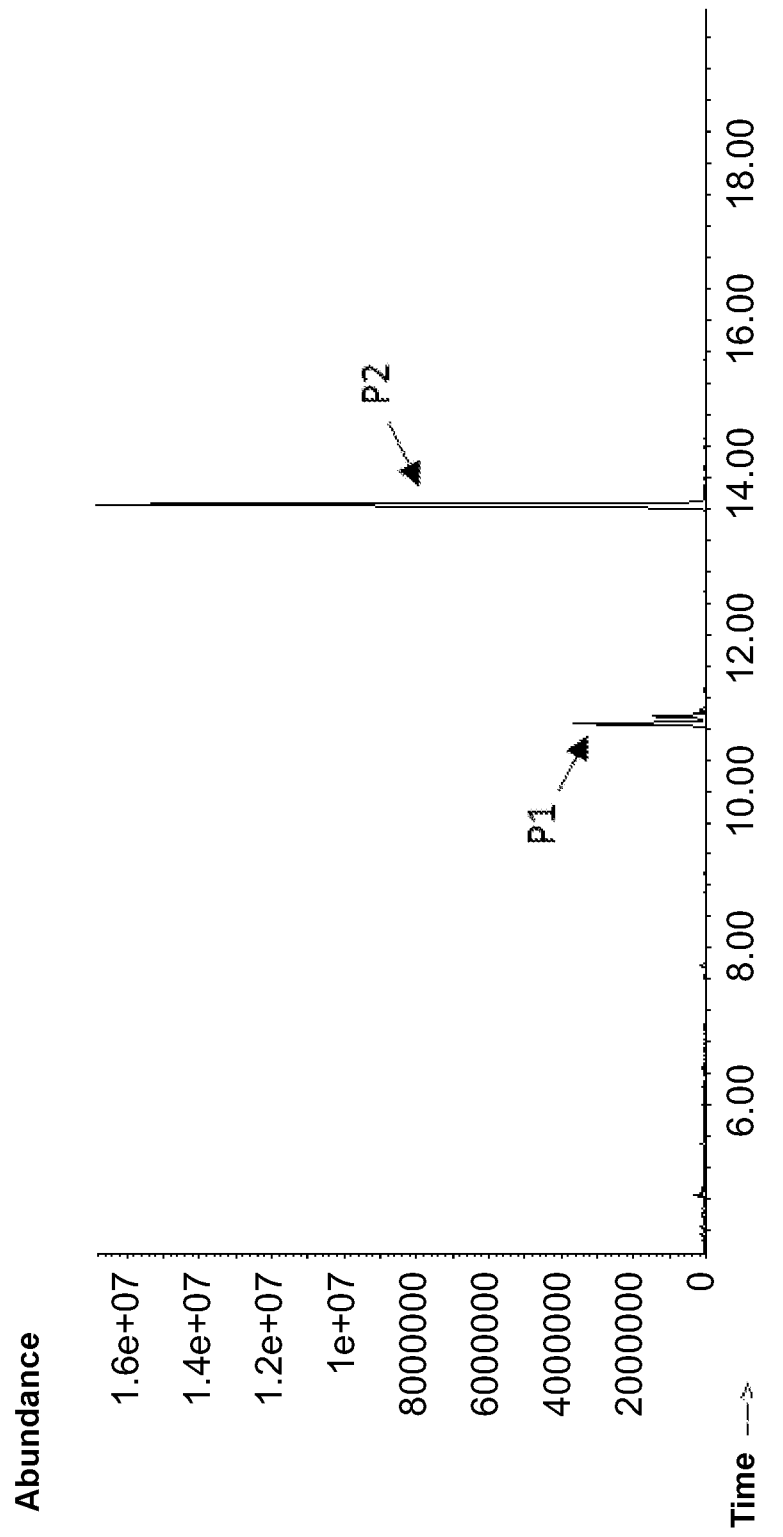
FIG. 15 shows an MS chromatogram obtained from a reaction solution of BLR(DE3)/pET-22b(+)Km$^R$-Sequ_13-LAH strain.
Figure 16:
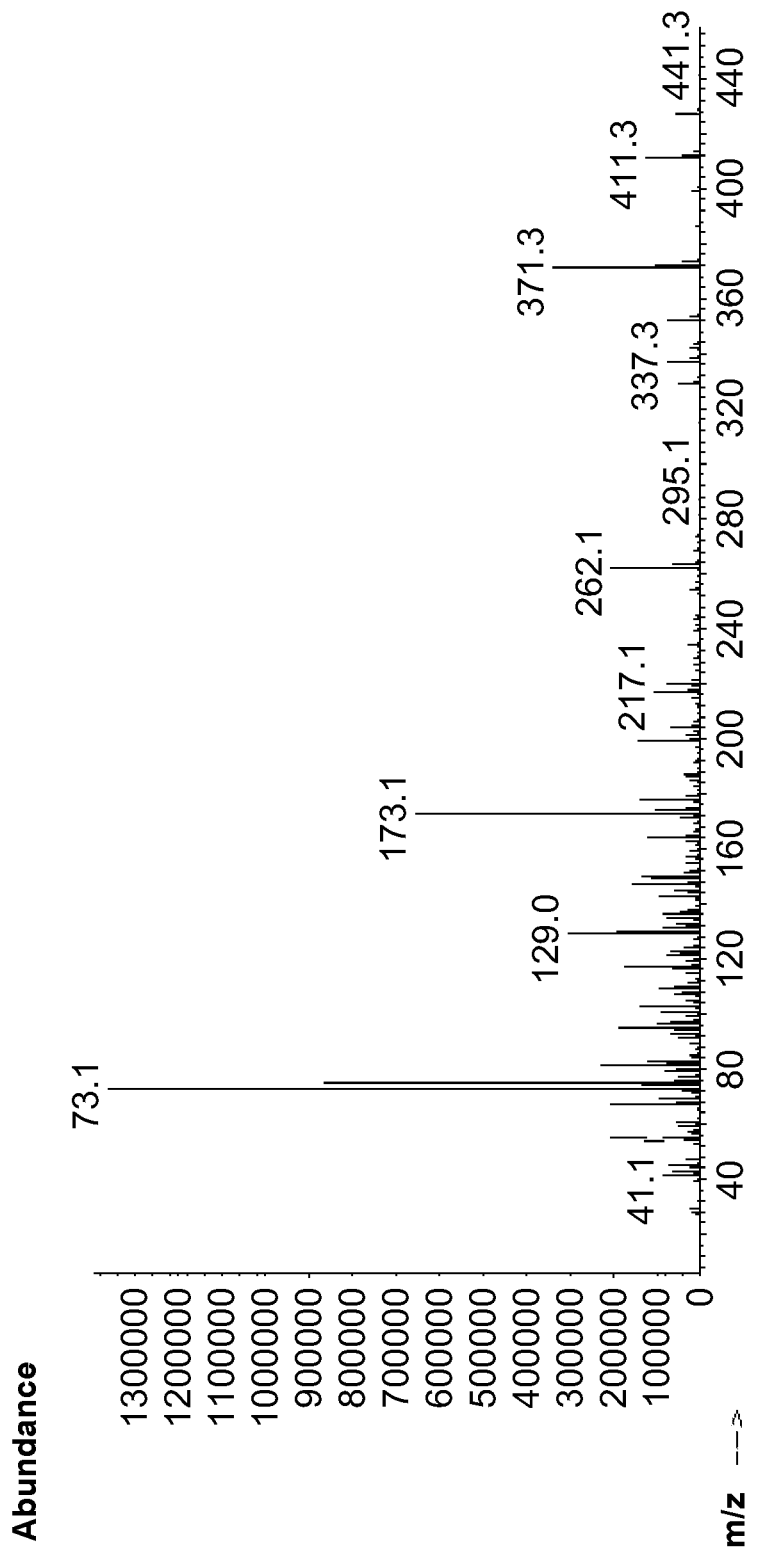
FIG. 16 shows an MS spectrum of P2 peaks obtained from a reaction solution of BLR(DE3)/pET-22b(+)Km$^R$-Laci_13-LAH strain.
Figure 17:
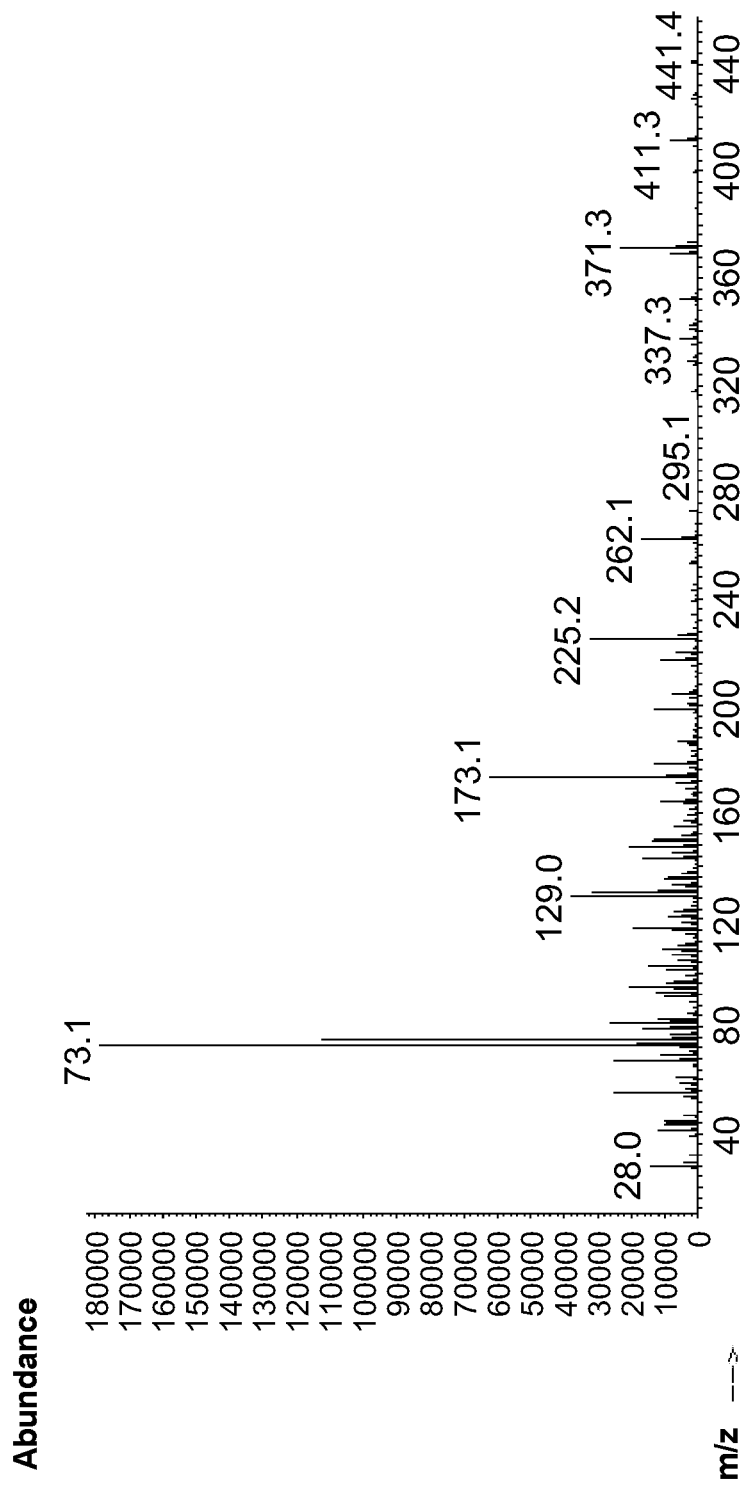
FIG. 17 shows an MS spectrum of P2 peaks obtained from a reaction solution of BLR(DE3)/pET-22b(+)Km$^R$-Lamy_13-LAH strain.
Figure 18:
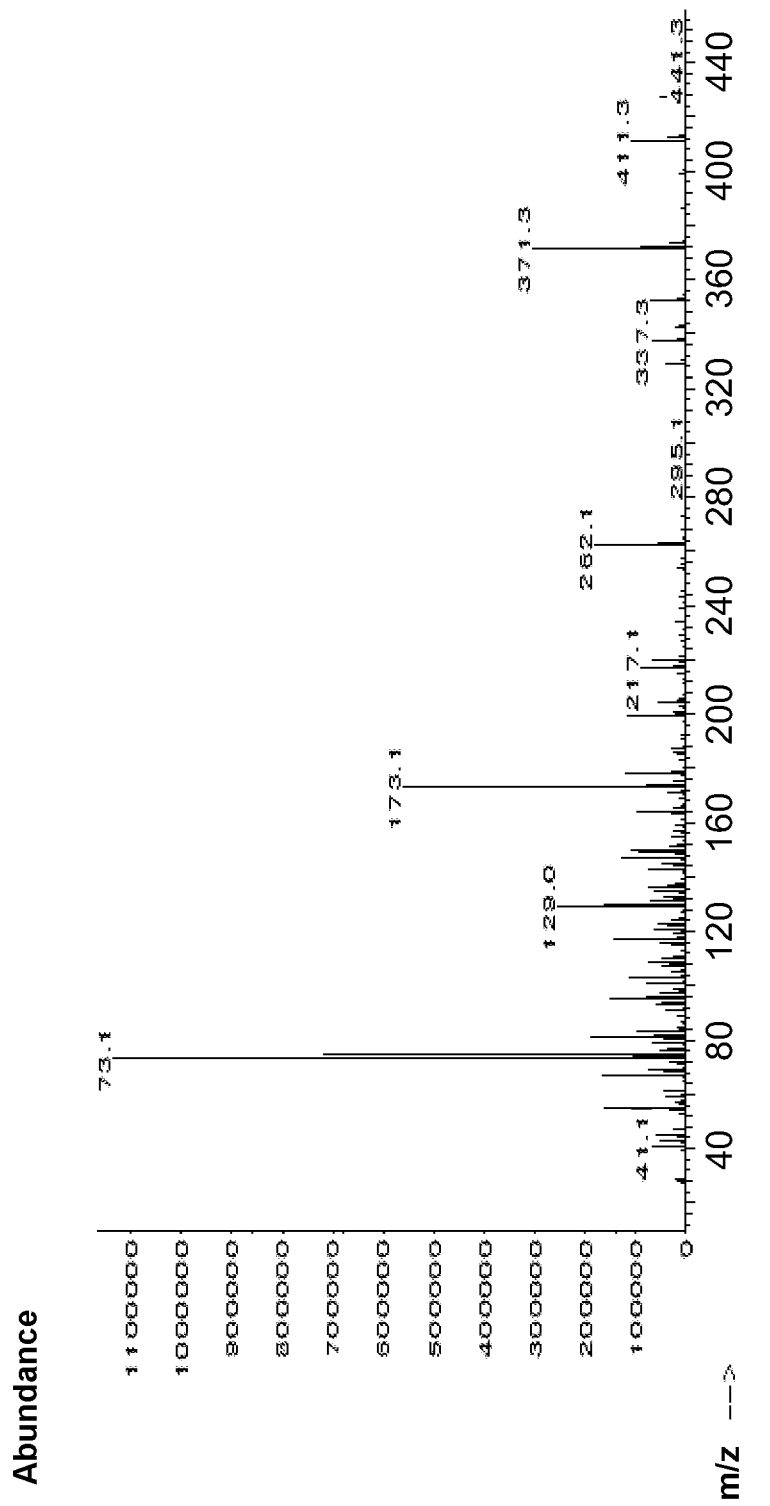
FIG. 18 shows an MS spectrum of P2 peaks obtained from a reaction solution of BLR(DE3)/pET-22b(+)Km$^R$-Lhel_13-LAH strain.
Figure 19:
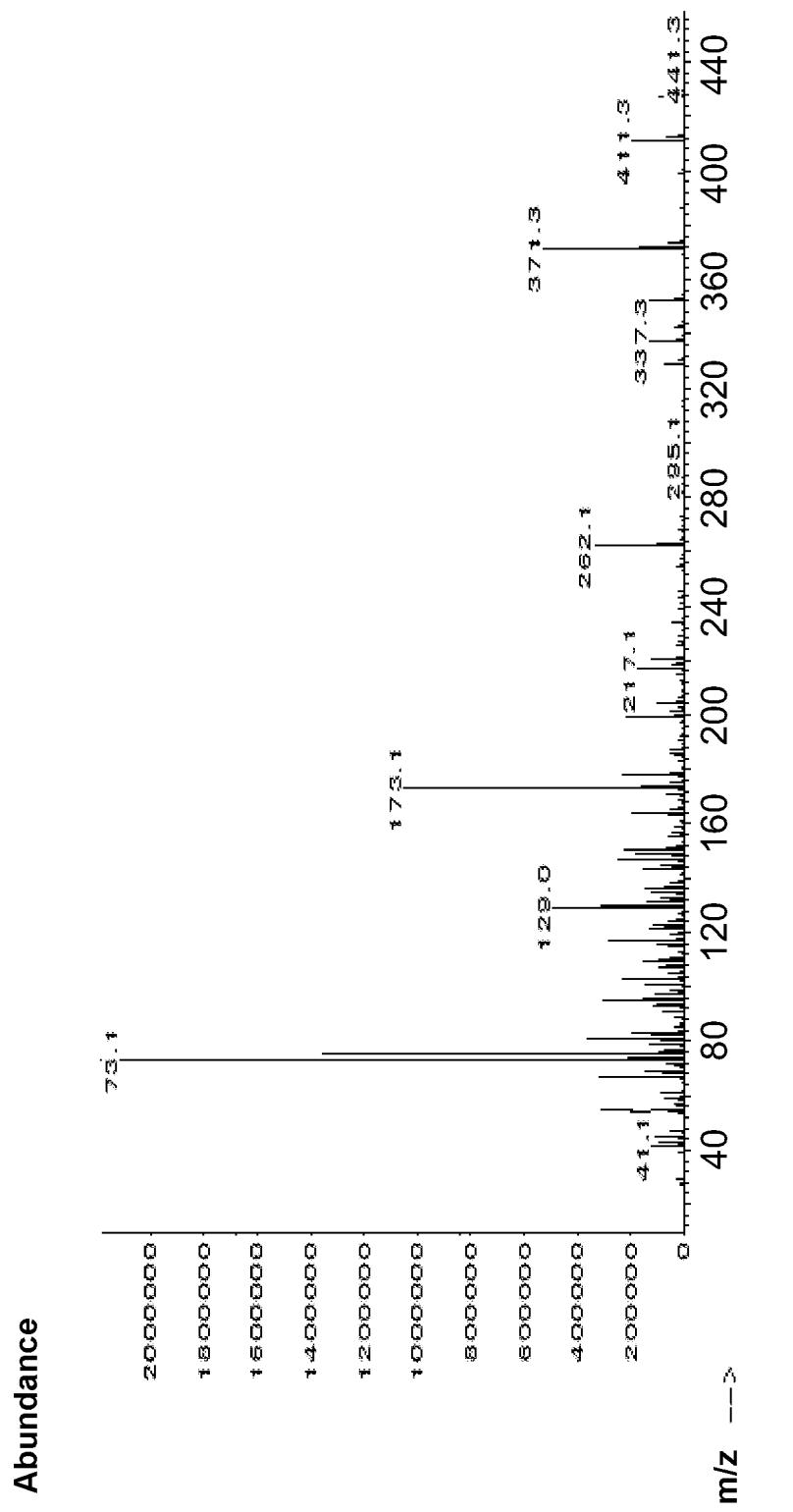
FIG. 19 shows an MS spectrum of P2 peaks obtained from a reaction solution of BLR(DE3)/pET-22b(+)Km$^R$-Lgal_13-LAH strain.
Figure 20:
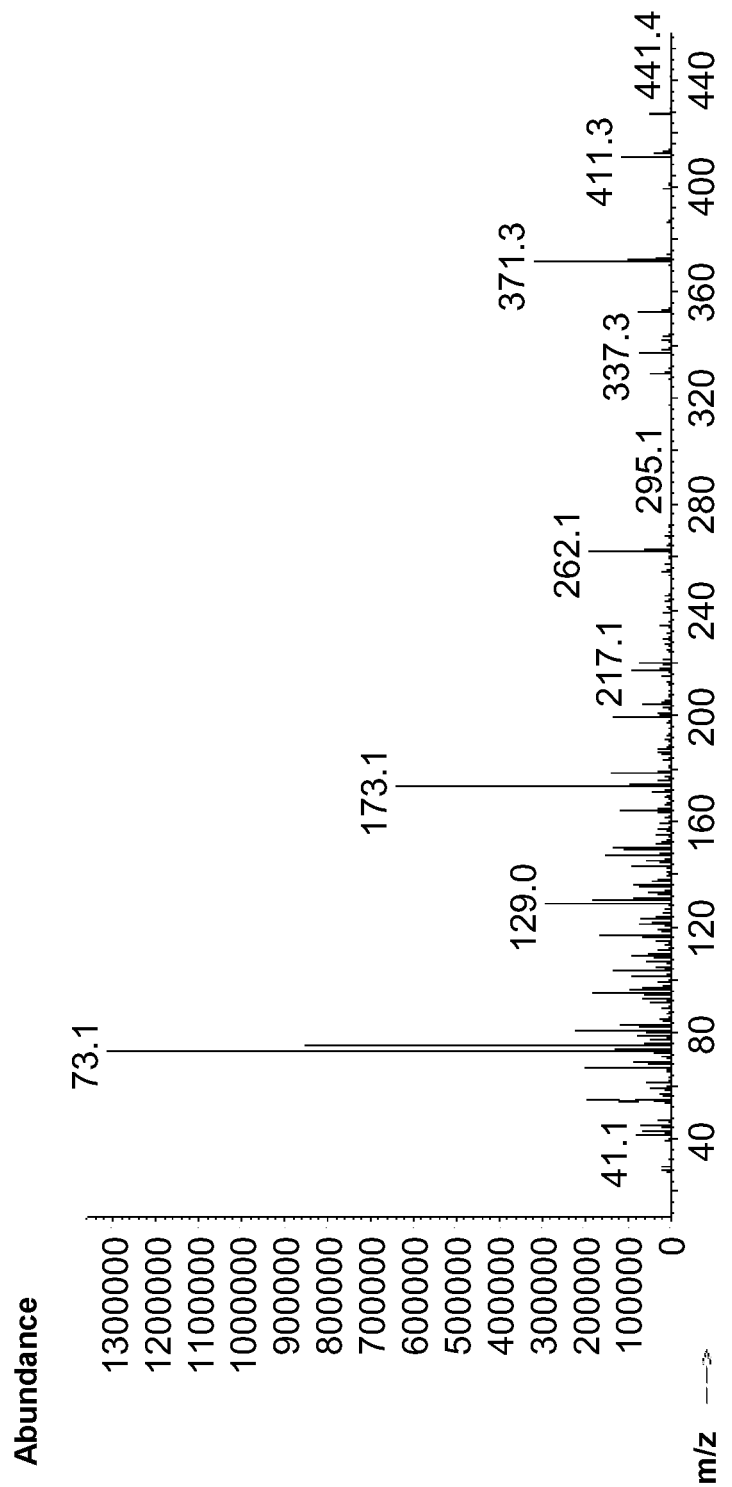
FIG. 20 shows an MS spectrum of P2 peaks obtained from a reaction solution of BLR(DE3)/pET-22b(+)Km$^R$-Lcri_13-LAH strain.
Figure 21:
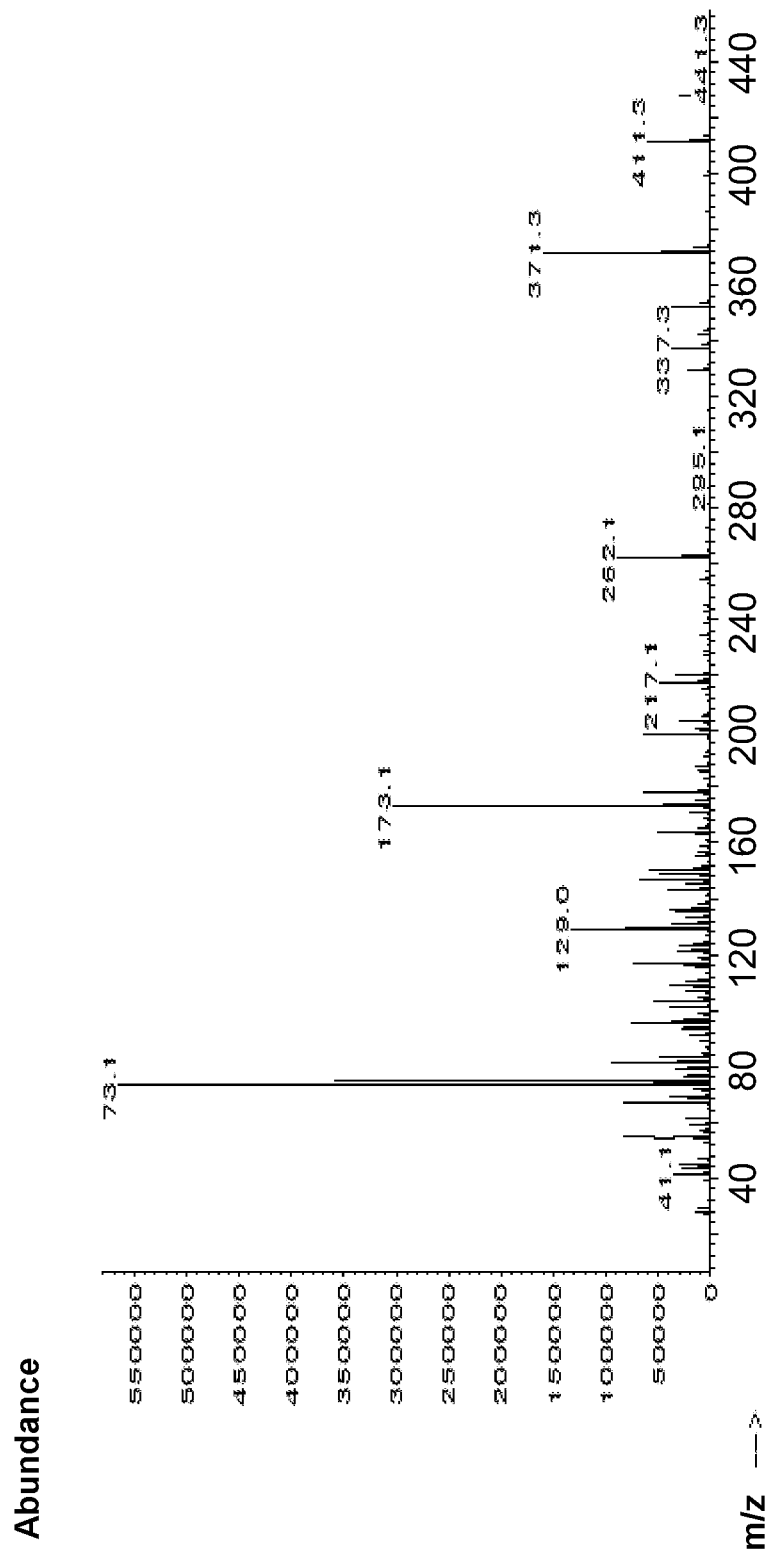
FIG. 21 shows an MS spectrum of P2 peaks obtained from a reaction solution of BLR(DE3)/pET-22b(+)Km$^R$-Lkef_13-LAH strain.
Figure 22:
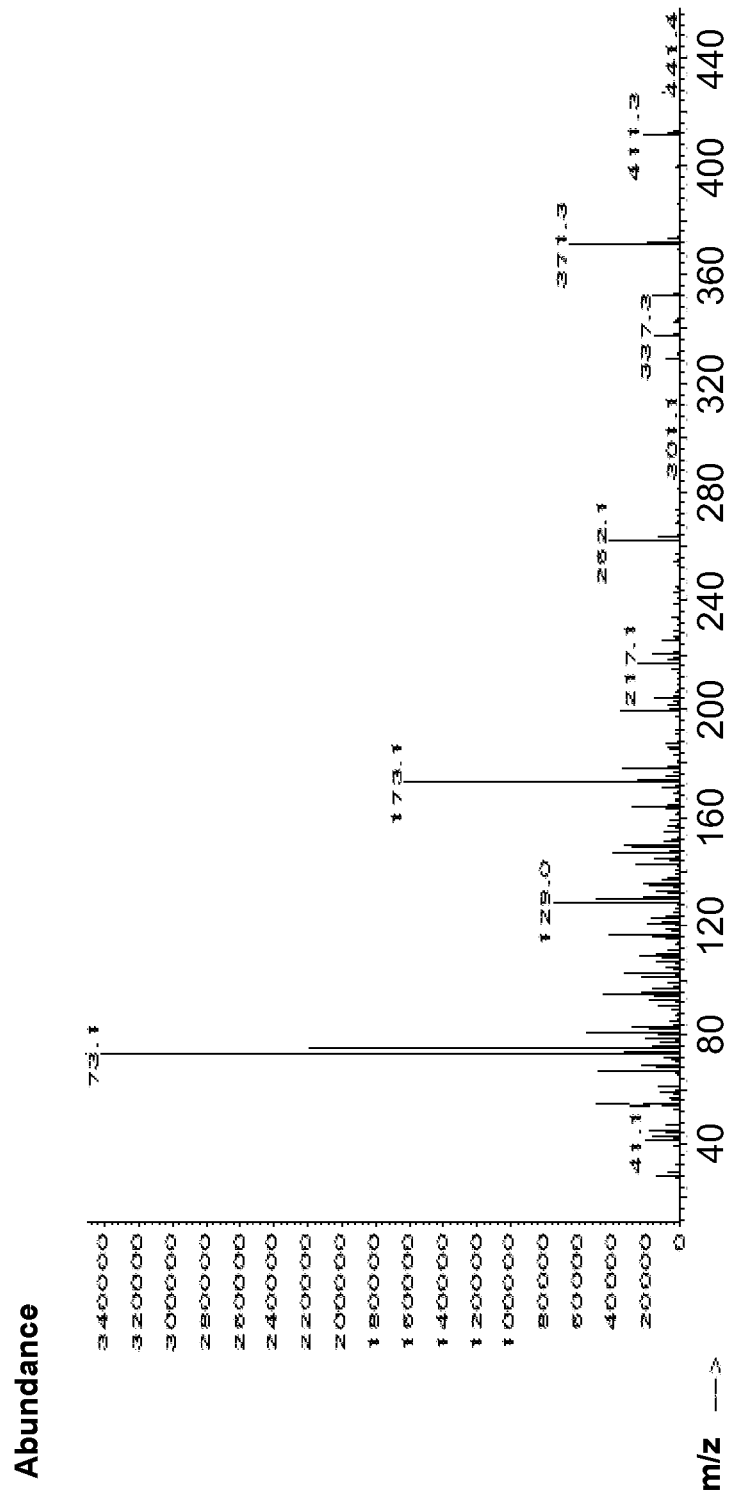
FIG. 22 shows an MS spectrum of P2 peaks obtained from a reaction solution of BLR(DE3)/pET-22b(+)Km$^R$-Lint_13-LAH strain.
Figure 23:
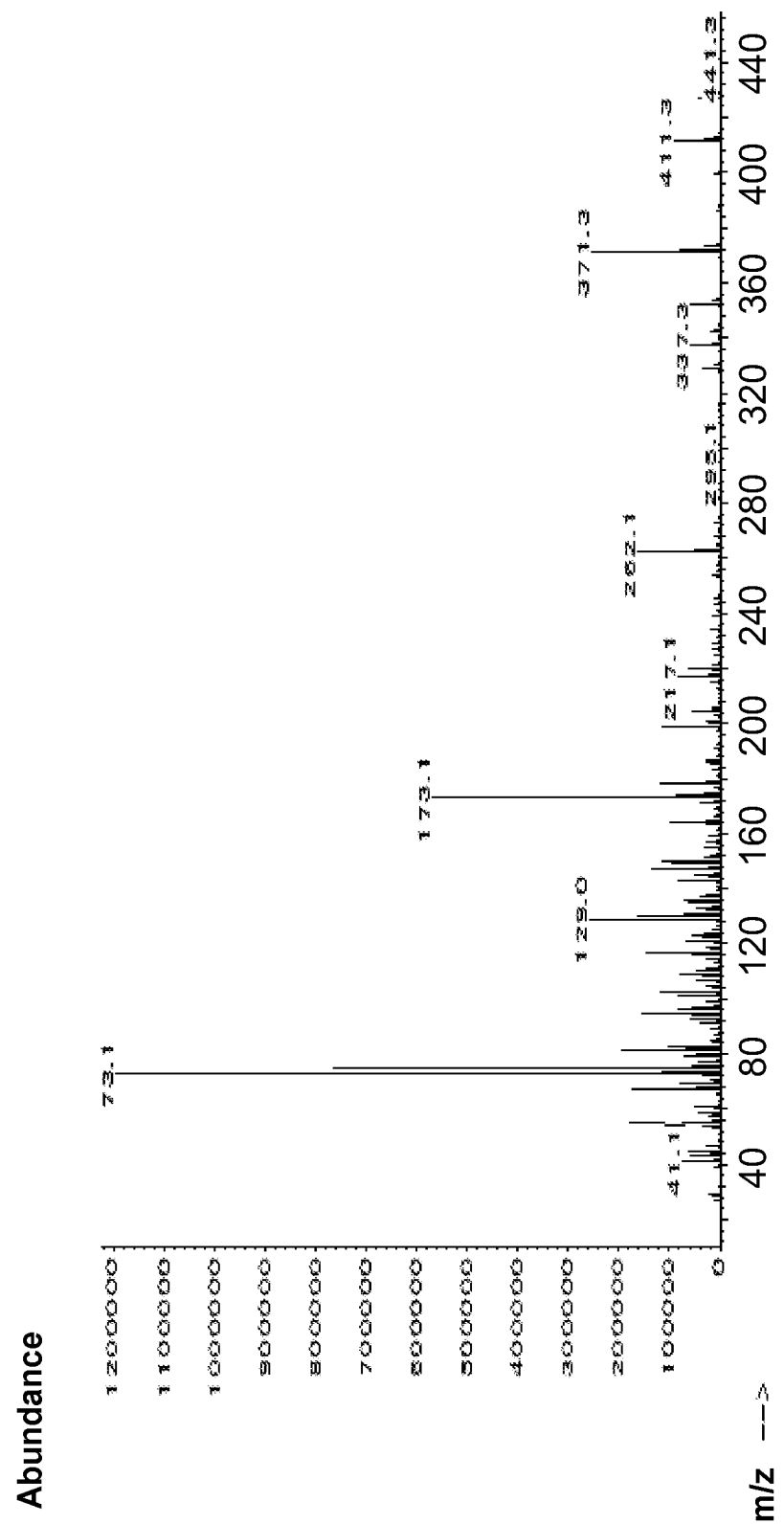
FIG. 23 shows an MS spectrum of P2 peaks obtained from a reaction solution of BLR(DE3)/pET-22b(+)Km$^R$-Lham_13-LAH strain.
Figure 24:
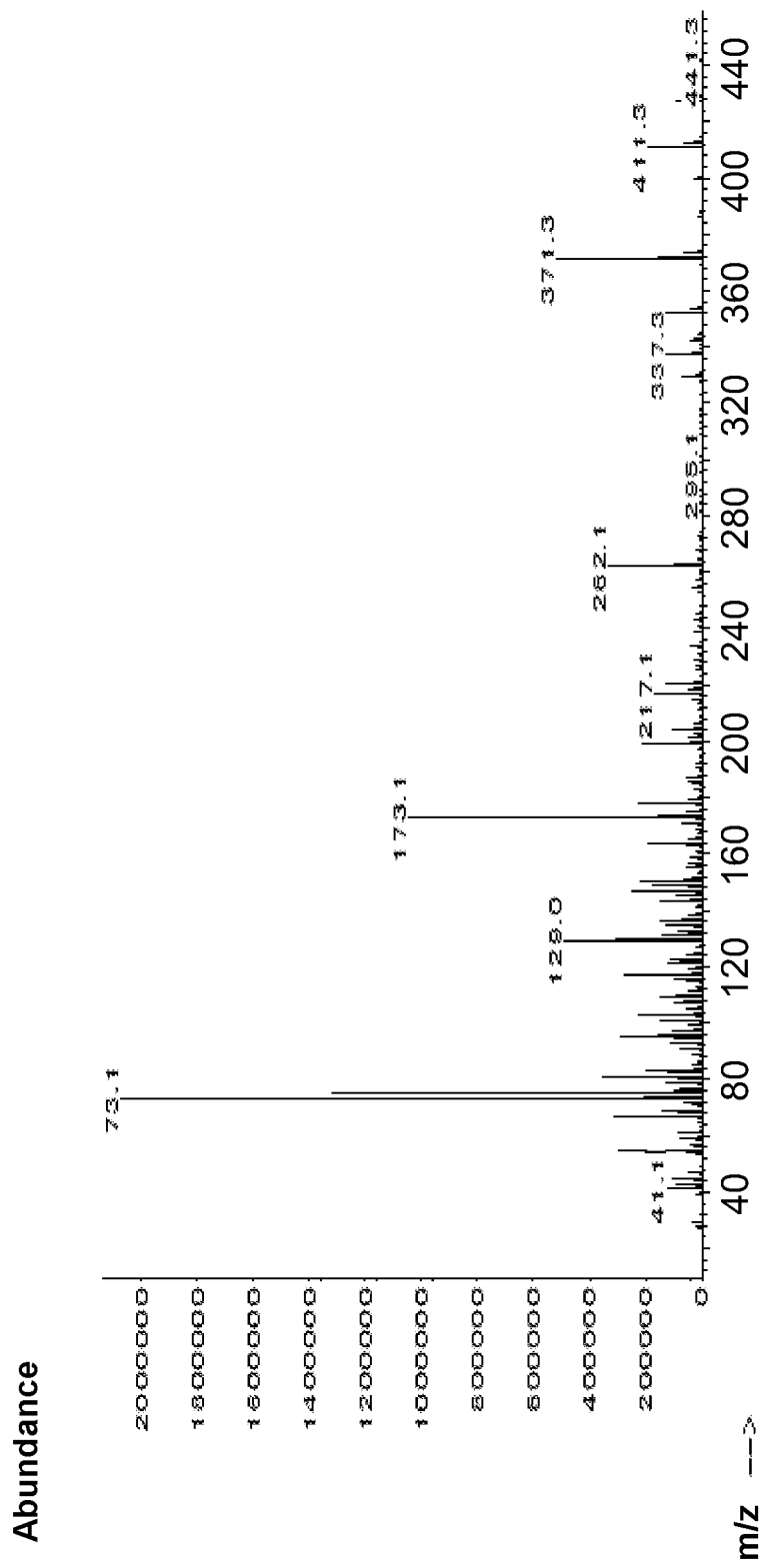
FIG. 24 shows an MS spectrum of P2 peaks obtained from a reaction solution of BLR(DE3)/pET-22b(+)Km$^R$-Lgas_13-LAH strain.
Figure 25:
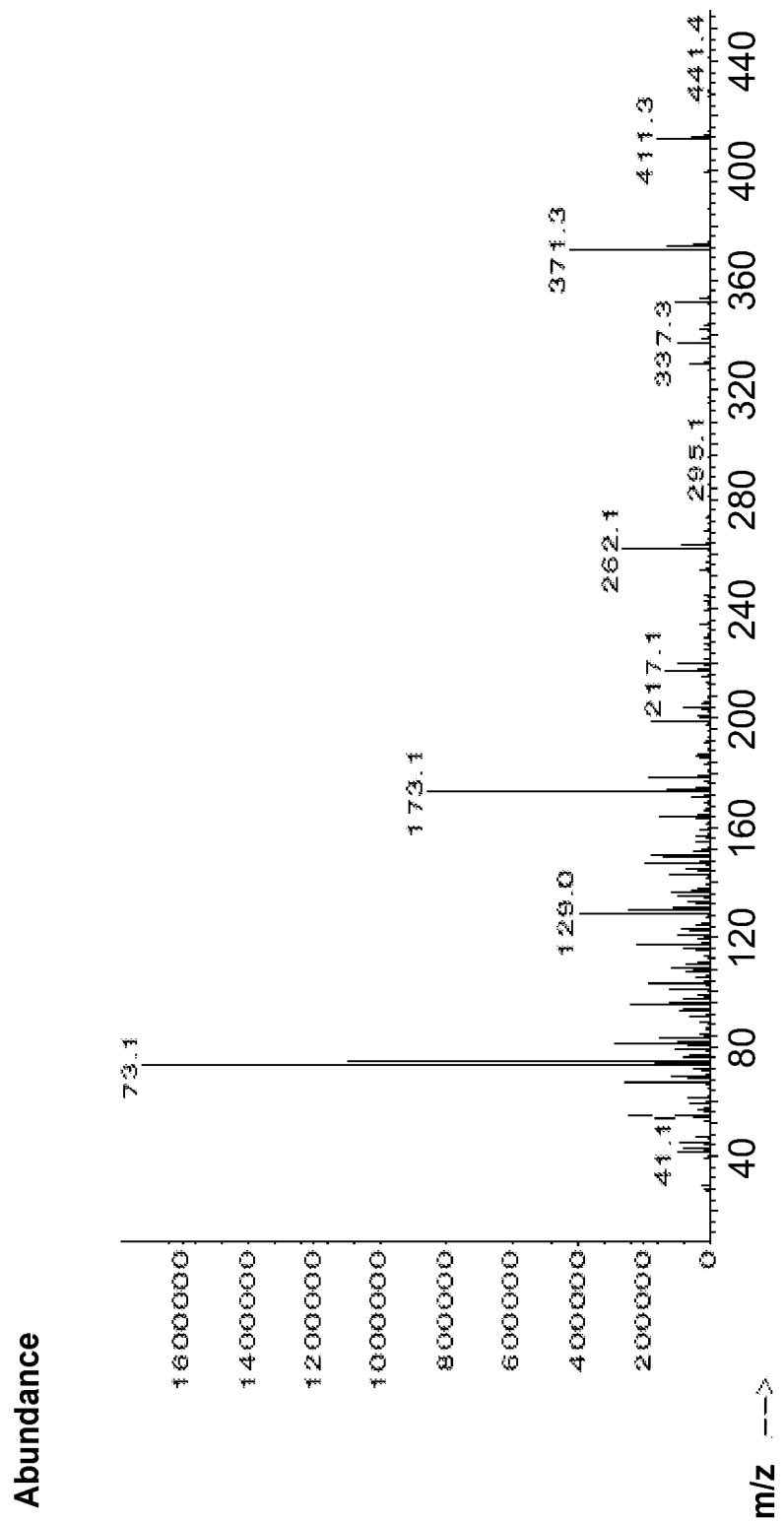
FIG. 25 shows an MS spectrum of P2 peaks obtained from a reaction solution of BLR(DE3)/pET-22b(+)Km$^R$-Pcla_13-LAH strain.
Figure 26:
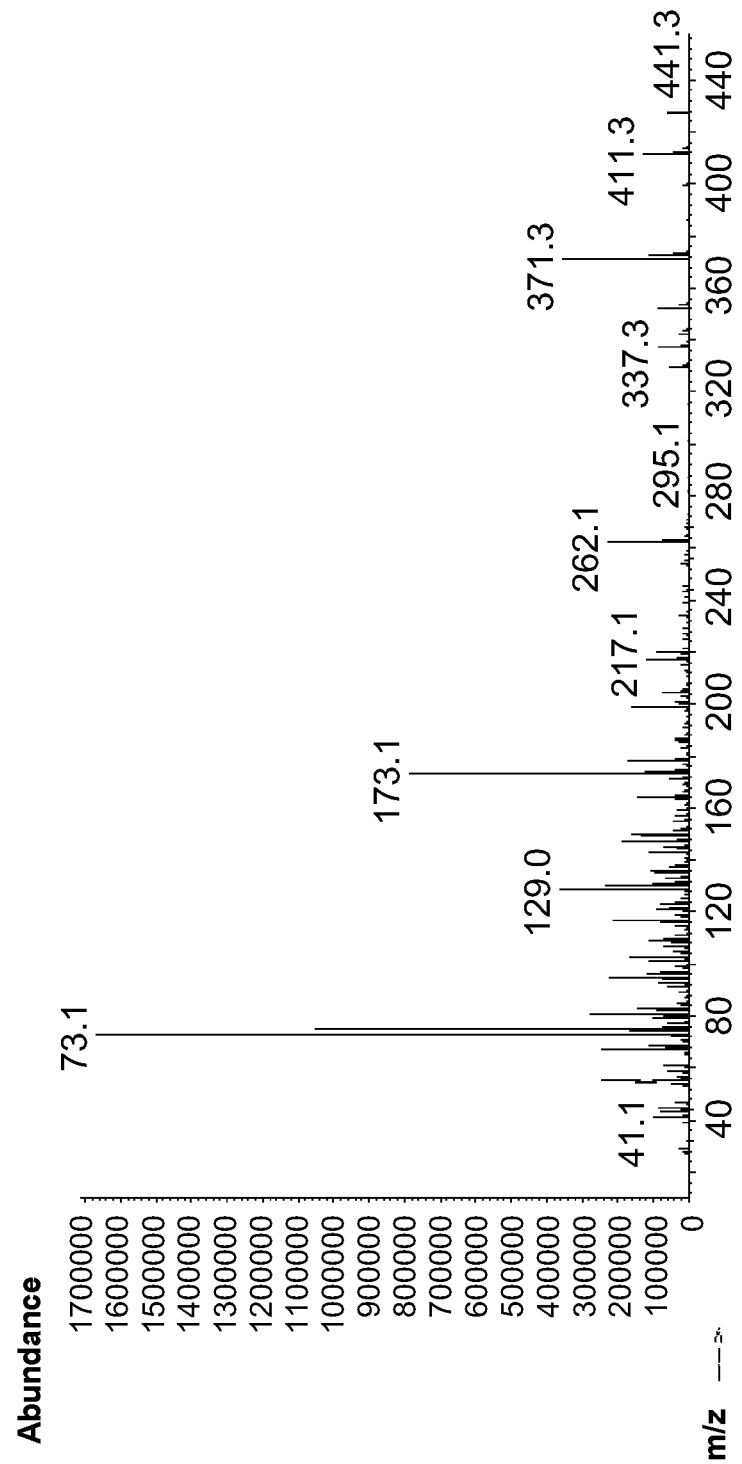
FIG. 26 shows an MS spectrum of P2 peaks obtained from a reaction solution of BLR(DE3)/pET-22b(+)Km$^R$-Lrum_13-LAH strain.
Figure 27:
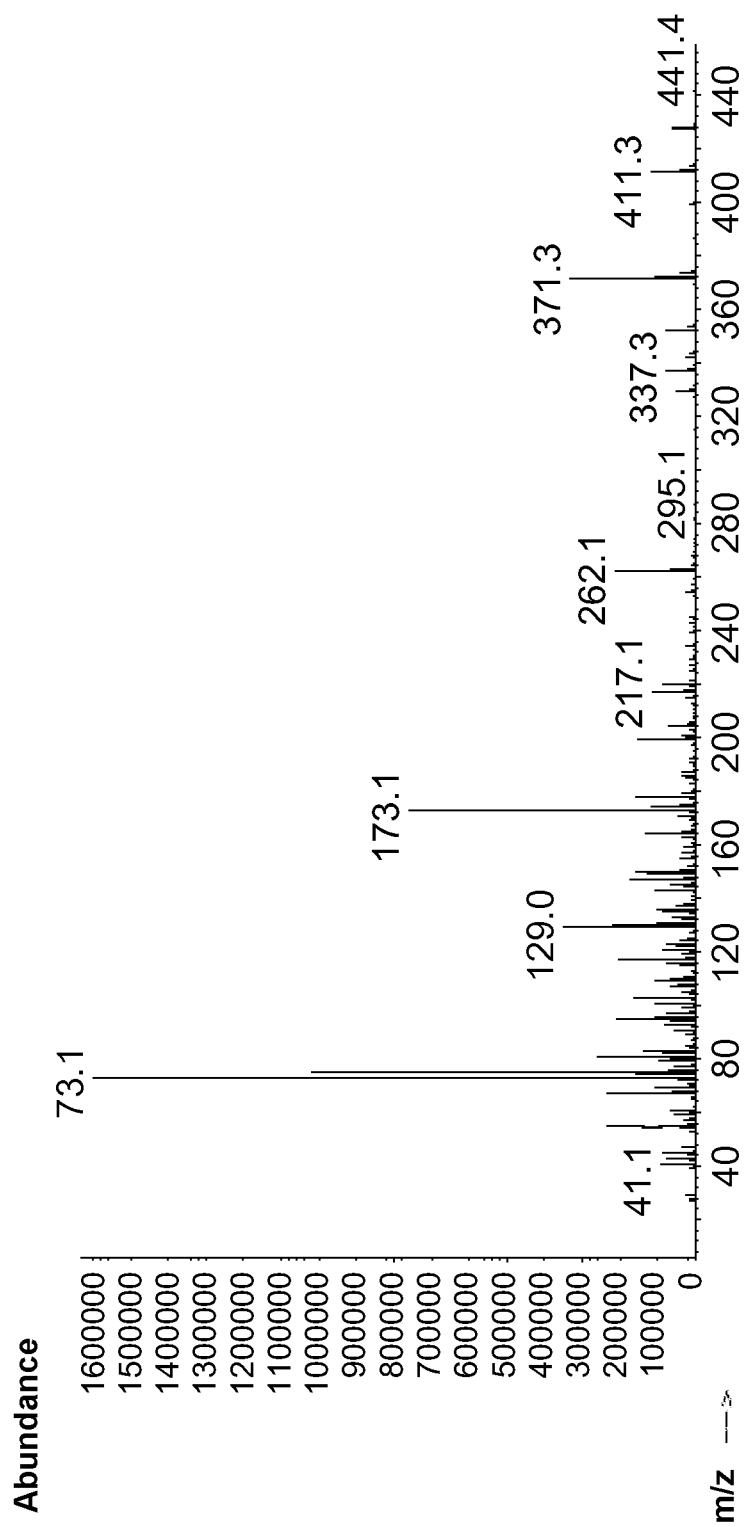
FIG. 27 shows an MS spectrum of P2 peaks obtained from a reaction solution of BLR(DE3)/pET-22b(+)Km$^R$-Sinf_13-LAH strain.
Figure 28:
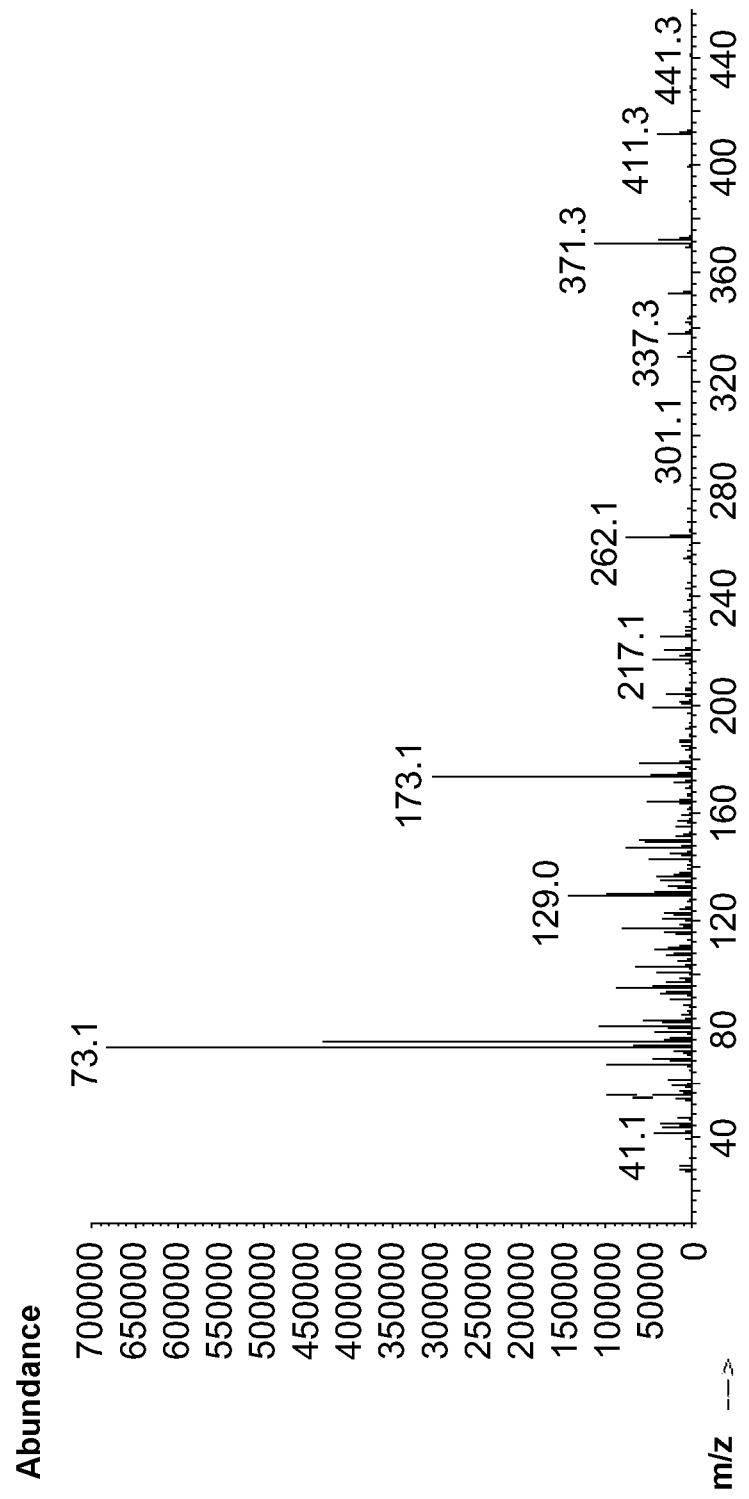
FIG. 28 shows an MS spectrum of P2 peaks obtained from a reaction solution of BLR(DE3)/pET-22b(+)Km$^R$-Smut_13-LAH strain.
Figure 29:
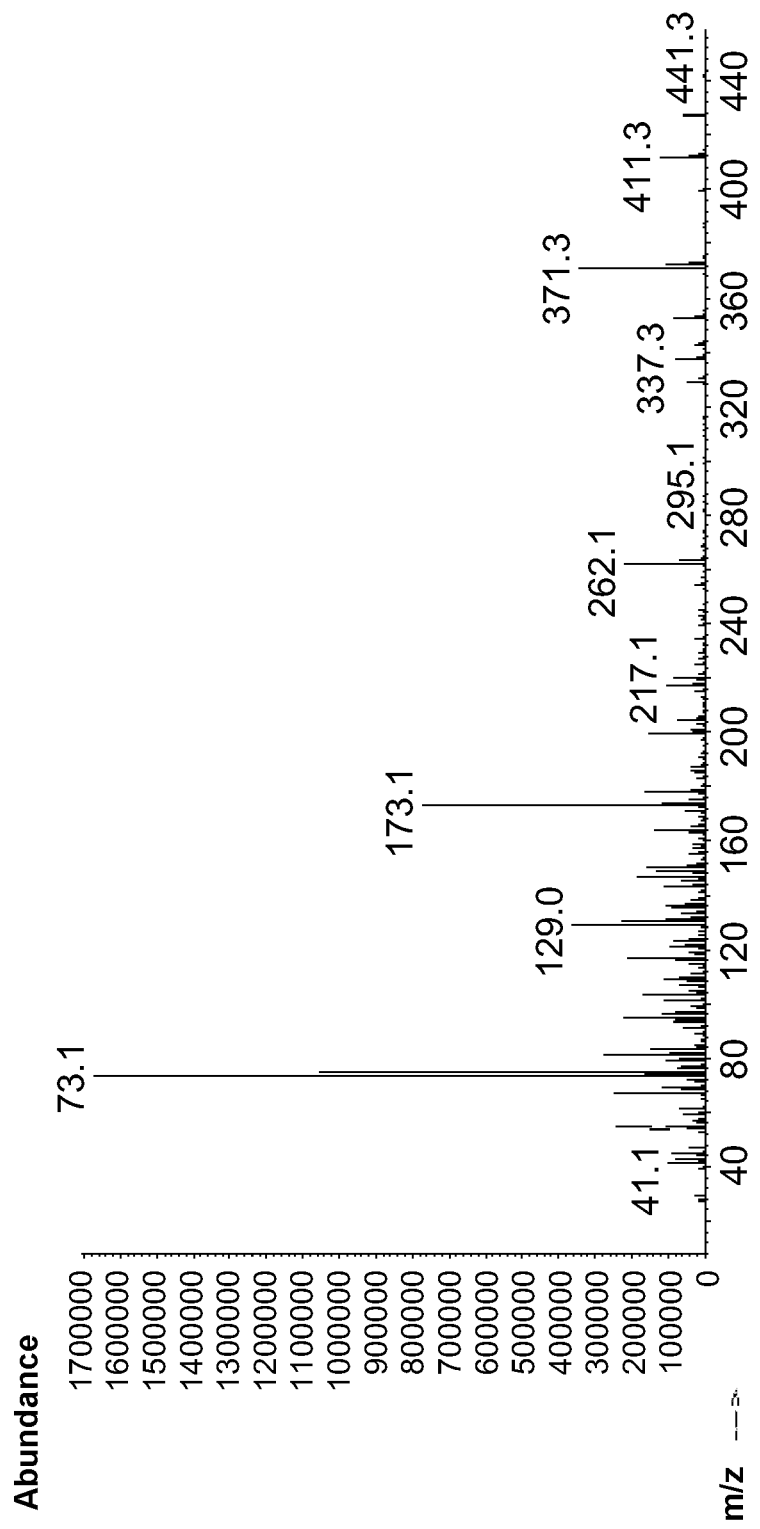
FIG. 29 shows an MS spectrum of P2 peaks obtained from a reaction solution of BLR(DE3)/pET-22b(+)Km$^R$-Sequ_13-LAH strain.

MS chromatograms and MS spectra obtained from the GC-MS analysis are shown in FIGS. 1 to 29.

A peak of R.T.=10.9 min represented by P1 denotes silylated (—SiMe$_3$) linolenic acid, and a peak of R.T.=13.6 min represented by P2 was shown to also have peaks characteristic at 73, 173 and 371 (m/Z) from analysis results of the MS spectra (see FIGS. 16 to 29). The analysis results of the MS spectra for silylated 13-HOD have been already published (Non-patent Literature: Park et al., J Biotechnol. 2015, 20; 208: 1-10), and were consistent with results obtained this time. Thus, it became evident that the peak of P2 is silylated 13-HOD. From the above results, it was found that 13-HOD was converted from linolenic acid in all 13-LAH expressing strains used in this investigation.

<Quantification Analysis of 13-HOD Utilizing GC-FID>

Next, produced 13-HOD was quantitatively analyzed using GC-FID. The samples were silylated as with above, and then subjected to GC-FID. An analysis condition for GC-FID is shown below, and results of the quantification analysis are shown in Table 7.

<Analysis Condition of GC-FID>

Apparatus: Shimadzu GC-2010 Plus/FID, column: Agilent DB-1 ms, 30 m, 0.25 mm, 0.25 μm (Part number 122-0132), injection amount: 1 μL, injection method: split 20:1, inlet: 230° C., column temperature program: starting at 90° C., then rising temperature up to 160° C. at 25° C./min, subsequently rising temperature up to 280° C. (kept for 2.5 min) at 5° C./min, carrier gas: helium, linear speed: 35 cm/s, detector: temperature at 250° C., uptake cycle 25 Hz, makeup flow (air): 30 mL/min. Ricinoleic acid where a hydroxyl group was introduced into position C12 of linoleic acid (from Tokyo Chemical Industry Co., Ltd., Product Number R0027) was silylated as with the samples to use as a preparation.

TABLE 7

Amount of produced 13-HOD by various 13-LAH expressing strains.

| Strain name | Amount of produced 13-HOD (g/L) | Relative amount of produced 13-HOD based on Laci_13-LAH |
|---|---|---|
| BLR(DE3)/pET-22b(+)Km$^R$ | Not detected | — |
| BLR(DE3)/pET-22b(+)Km$^R$-Laci_13-LAH | 10.51 | 1.00 |
| BLR(DE3)/pET-22b(+)Km$^R$-Lamy_13-LAH | 2.48 | 0.24 |
| BLR(DE3)/pET-22b(+)Km$^R$-Lhel_13-LAH | 8.77 | 0.83 |
| BLR(DE3)/pET-22b(+)Km$^R$-Lgal_13-LAH | 11.38 | 1.08 |
| BLR(DE3)/pET-22b(+)Km$^R$-Lcri_13-LAH | 10.64 | 1.01 |
| BLR(DE3)/pET-22b(+)Km$^R$-Lkef_13-LAH | 8.33 | 0.79 |
| BLR(DE3)/pET-22b(+)Km$^R$-Lint_13-LAH | 5.46 | 0.52 |
| BLR(DE3)/pET-22b(+)Km$^R$-Lham_13-LAH | 16.92 | 1.61 |
| BLR(DE3)/pET-22b(+)Km$^R$-Lgas_13-LAH | 14.94 | 1.42 |
| BLR(DE3)/pET-22b(+)Km$^R$-Pcla_13-LAH | 10.57 | 1.01 |
| BLR(DE3)/pET-22b(+)Km$^R$-Lrum_13-LAH | 9.30 | 0.88 |
| BLR(DE3)/pET-22b(+)Km$^R$-Sinf_13-LAH | 9.85 | 0.94 |
| BLR(DE3)/pET-22b(+)Km$^R$-Smut_13-LAH | 33.17 | 3.16 |
| BLR(DE3)/pET-22b(+)Km$^R$-Sequ_13-LAH | 24.61 | 2.34 |

From the above results, higher amounts of produced 13-HOD were observed in 13-LAH from *Lactobacillus gallinarum, Lactobacillus crispatus, Lactobacillus hamster, Lactobacillus gasseri, Pediococcus claussenii, Streptococcus mutans*, and *Streptococcus equinus* than in known 13-LAH from *Lactobacillus acidophilus*.

Example 3: Conversion Reaction from 13-HOD to δ-Decalactone Utilizing *Yarrowia lipolytica*

<Construction of Plasmid pUC-APDH1::URA3 for Construction of *Yarrowia lipolytica* W29ΔURA3>

Next, conversion to δ-decalactone was attempted using 13-HOD obtained in this investigation. A genomic sequence of *Y. lipolytica* CLIB122 strain was published (GCF_000002525.2). Primers IF-ura3_f1 (SEQ ID NO:63) and IF-ura3_r1 (SEQ ID NO:64) for amplifying a URA3 gene were designed based information for the genomic sequence. PCR (PrimeSTAR GXL (registered trade name), 98° C. for 10 seconds, 55° C. for 15 seconds and 68° C. for 60 seconds, 35 cycles) was performed using genomic DNA of *Y. lipolytica* W29 (CBS7504) strain as the template and using the primers IF-ura3_f1 and IF-ura3_r1 to obtain a gene fragment including an ORF region of the URA3 gene. Likewise, PCR (PrimeSTAR GXL (registered trade name), 98° C. for 10 seconds, 55° C. for 15 seconds and 68° C. for 60 seconds, 35 cycles) was performed using genomic DNA of this strain as the template and using a combination of primers IF-Dpdh1_f1 (SEQ ID NO:65) and IF-Dpdh1_r1 (SEQ ID NO:66) and a combination of primers IF-Dpdh1_f2 (SEQ ID NO:67) and IF-Dpdh1_r2 (SEQ ID NO:68), respectively to obtain a DNA fragment of an upstream region (about 1 kb) of a PDH1 gene and a DNA fragment of a downstream region (about 1 kb) of the PDH1 gene, respectively. Further, PCR (PrimeSTAR GXL (registered trade name), 98° C. for 10 seconds, 55° C. for 15 seconds and 68° C. for 240 seconds, 35 cycles) was performed using plasmid DNA of pUC18 (from TAKARA, Product Number 3218) as the template and using primers R-M13-M4 (SEQ ID NO:69) and R-M13-RV (SEQ ID NO:70) to obtain a DNA fragment of the plasmid. Four DNA fragments obtained above were mixed and ligated using In-Fusion (registered trade name) HD cloning Kit (from Clontech, Product Number 639648). This was used to transform *E. coli* JM109 strain. Culture medium containing transformants was applied onto LB agar medium containing 100 mg/L of carbenicillin disodium (from Nacalai Tesque, Product Number 07129-14). Using the obtained transformant, colony PCR (SapphireAmp Fast PCR Master Mix, from TAKARA, Product Number RR350A, 98° C. for 5 seconds, 55° C. for 5 seconds and 68° C. for 60 seconds, 35 cycles) was performed using primers M13-M4 (SEQ ID NO:71) and M13-RV (SEQ ID NO:72) to confirm insertion of the target gene fragment into the plasmid. The obtained plasmid was designated as pUC-ΔPDH1::URA3. Sequences of the primers used for the construction of pUC-ΔPDH1::URA3 are shown in Table 8.

<Construction of *Yarrowia lipolytica* W29ΔURA3 Strain>

Next, PCR (PrimeSTAR GXL (registered trade name), 98° C. for 10 seconds, 55° C. for 15 seconds and 68° C. for 360 seconds, 35 cycles) was performed using plasmid DNA of pUC-ΔPDH1::URA3 as the template and using primers HR-Dpdh1_f1 (SEQ ID NO:73) and HR-Dpdh1_r1 (SEQ ID NO:74). To remove the Template DNA in the obtained PCR product, the PCR product was digested with a restriction enzyme DpnI, and purified using Wizard (registered trade name) SV Gel and PCR Clean-UP system (from Promega, Product Number A9281). The obtained DNA fragment was used for transformation. Subsequently, competent cells of *Y. lipolytica* W29 strain were prepared by the following procedure. The W29 strain was cultured in 3 mL of YPD medium (10 g/L of Bacto yeast extract, 20 g/L of polypeptone, 20 g/L of glucose) at 30° C. overnight. Then, 30 μL of the culture medium was inoculated again to 3 mL of fresh YPD medium, and cultured until absorbance (660 nm) reached around 0.8. Microbial cells were collected from the obtained culture medium by centrifugation. The microbial cells after being further prepared as competent cells was mixed with about 2 g of pUC-ΔPDH1::URA3 to perform the transformation. The preparation of competent cells and the transformation were performed using Frozen-EZ Yeast Transformation II Kit (ZYMO Research, Product Number T2001) according to an attached protocol. A microbial cell suspension after the transformation was cultured for recovery in YPD medium at 30° C. overnight, then microbial cells were collected, and applied onto SC+5-FOA agar medium (22.2 g/L of glucose, 6.7 g/L of yeast nitrogen base, 1.5 g/L of 5-FOA, 20 g/L of Bacto agar) to obtain a 5-FOA resistant strain. Uracil requirement of the obtained resistant strain was confirmed in SC agar medium and SC (-ura) agar medium (22.2 g/L of glucose, 6.7 g/L of yeast nitrogen base without amino acid, 0.77 g/L of Ura DO supplement, 20 g/L of Bacto agar). Using this strain exhibiting the uracil requirement, colony PCR (SapphireAmp Fast PCR Master Mix, suppled from TAKARA, Product Number RR350A, 98° C. for 5 seconds, 55° C. for 5 seconds and 68° C. for 30 seconds, 35 cycles) was performed using primers CP-Dura3-f1 (SEQ ID NO:75) and CP-Dura3-r1 (SEQ ID NO:76) to confirm deletion of the URA3 gene. The uracil requirement strain thus obtained was used as W29ΔURA3 strain. Sequences of the primers used for the construction of W29ΔURA3 strain are shown in Table 8.

increases an amount of produced δ-decalactone (Non-patent Literature: Wache et al., Appl. Environ. Microbiol., 2000, 66: 1233-1236). Thus, the AOX3 gene (YALI0D24750g) encoded on a chromosome was destroyed in *Y. lipolytica* W29ΔURA3 strain. A gene sequence and an amino acid sequence of the AOX3 gene are shown in SEQ ID NOS 77 and 78, respectively. First, a plasmid pUC57-AOX3-Hyg$^R$ for destroying that gene was constructed according to the following procedure. A plasmid pUC57-AOX3-URA3 where a gene fragment having homologous regions to 1000 bp before and after the AOX3 gene at both ends of the URA3 gene from *Y. lipolytica* had been cloned into pUC57 was chemically synthesized utilizing the artificial gene synthesis service provided by GenScript. A nucleotide sequence of pUC57-AOX3-URA3 is shown in SEQ ID NO:79. Next, the URA 3 gene in the same plasmid was replaced with a hygromycin resistant gene. A plasmid, PUC57-TEF-Hyg$^R$ where a gene fragment where hygromycin B phosphotransferase (hereinafter abbreviated as Hyg$^R$) was linked to downstream of TEF 1 promoter from *Saccharomyces cerevisiae* had been cloned into pUC57 was chemically synthesized utilizing the artificial gene synthesis service provided by GenScript as with above. A nucleotide sequence of PUC57-TEF-Hyg$^R$ is shown in SEQ ID NO:80. PCR

TABLE 8

Sequences of primers used for the construction of pUC-ΔPDH1::URA3 and W29ΔURA3 strain

| Primer name | Nucleotide sequence (5'-3') | Nucleotide sequence number |
|---|---|---|
| IF-ura3_f1 | 5'TACTCTACAGCGAGTATACCTGTACAGACTG3' | SEQ ID NO: 63 |
| IF-ura3_r1 | 5'TGACCTTGGTACTCAAAGAATATTCAGATG3' | SEQ ID NO: 64 |
| IF-Dpdh1_f1 | 5'CCCAGTCACGACGTTTGATCCCAGCTTTGTTTCTAGCTC3' | SEQ ID NO: 65 |
| IF-Dpdh1_r1 | 5'TGAGTACCAAGGTCAATTGTCTTGTTTTCACAC3' | SEQ ID NO: 66 |
| IF-Dpdh1_f2 | 5'TACTCGCTGTAGAGTAGAATGTAATTACTAATG3' | SEQ ID NO: 67 |
| IF-Dpdh1_r2 | 5'GGAAACAGCTATGACTGCTCCTGGACCAGAGCCTTGAG3' | SEQ ID NO: 68 |
| R-M13-M4 | 5'GTCATAGCTGTTTCCTGTGT3' | SEQ ID NO: 69 |
| R-M13-RV | 5'AACGTCGTGACTGGGAAAAC3' | SEQ ID NO: 70 |
| M13-M4 | 5'GTTTTCCCAGTCACGACGTT3' | SEQ ID NO: 71 |
| M13-RV | 5'ACACAGGAAACAGCTATGAC3' | SEQ ID NO: 72 |
| HR-Dpdh1_f1 | 5'TGATCCCAGCTTTGTTTCTAGCTC3' | SEQ ID NO: 73 |
| HR-Dpdh1_r1 | 5'TGCTCCTGGACCAGAGCCTTGAG3' | SEQ ID NO: 74 |
| CP-Dura3_f1 | 5'ACACTGCTCACTATCGCAGGCTGC3' | SEQ ID NO: 75 |
| CP-Dura3_r1 | 5'AGCTTCAAAACACACAGCAGTCC3' | SEQ ID NO: 76 |

<Construction of Plasmid pUC57-AOX3-Hyg$^R$ for Destruction of AOX3 Gene>

An acetyl-CoA oxidase gene was destroyed for the purpose of enhancing an ability of producing δ-decalactone. There are six genes encoding acetyl-CoA oxidase in *Y. lipolytica*. It has been reported that among them, deletion of acetyl-CoA oxidase 3 (hereinafter abbreviated as AOX3) exhibiting high substrate affinity to short chain fatty acids (PrimeSTAR GXL (registered trade name), 98° C. for 10 seconds, 55° C. for 5 seconds and 68° C. for 300 seconds, 35 cycles) was performed using p57UC-AOX3-URA3 as the template and using primers AOX3_insert_F (SEQ ID NO:81) and AOX3_insert_R (SEQ ID NO:82) to obtain a DNA fragment. Likewise, PCR (PrimeSTAR GXL (registered trade name), 98° C. for 10 seconds, 55° C. for 5 seconds and 68° C. for 300 seconds, 35 cycles) was performed using pUC57-TEF-Hyg[R] as the template and using primers AOX3_backbone_F (SEQ ID NO:83) and AOX3_backbone_R (SEQ ID NO:84) to obtain a DNA fragment where the TEF promoter was ligated to the hygromycin resistant gene. The above two DNA fragments were applied to agarose gel electrophoresis, corresponding bands were cut out from the gel, and purified using Wizard (registered trade name) SV Gel and PCR Clean-UP system (Promega). The obtained two purified DNA fragments were mixed and ligated using In-Fusion (registered trade name) HD cloning Kit (from Clontech, Product Number 639648). This was used to transform E. coli JM109 strain. Culture medium containing transformants was applied onto LB agar medium containing 100 mg/L of carbenicillin disodium (from Nacalai Tesque, Product Number 07129-14). Using the obtained transformant, colony PCR (SapphireAmp Fast PCR Master Mix, supplied from TAKARA, Product Number RR350A, 98° C. for 5 seconds, 55° C. for 5 seconds and 72° C. for 30 seconds, 35 cycles) was performed using primers pUC57_F (SEQ ID NO:85) and pUC57_R (SEQ ID NO:86) to confirm insertion of the target gene fragment into the plasmid. The obtained plasmid was designated as pUC57-AOX3-Hyg[R]. A nucleotide sequence of pUC57-AOX3-Hyg[R] is shown in SEQ ID NO:87. Sequences of the primers used for the construction of pUC57-AOX3-Hyg[R] are shown in Table 9.

enzyme DpnI, and purified using Wizard (registered trade name) SV Gel and PCR Clean-UP system (from Promega, Product Number A9281). The obtained DNA fragment was used for transformation. Subsequently, competent cells of Y. lipolytica W29ΔURA3 strain (hereinafter abbreviated as W29ΔURA3 strain) were prepared according to the following procedure. W29ΔURA3 strain was cultured in YPD medium (10 g/L of Bacto yeast extract, 20 g/L of polypeptone, 20 g/L of glucose) at 30° C. overnight, then 30 μL of this culture medium was inoculated again to 3 mL of fresh YPD medium, and cultured until the absorbance (660 nm) reached around 0.8. Microbial cells were collected from the obtained culture medium by centrifugation. After preparation of competent cells, the cells were mixed with about 1 g of the purified DNA fragment to perform the transformation. The preparation of competent cells and the transformation were carried out using Frozen-EZ Yeast Transformation II Kit (ZYMO Research, Product Number T2001) according to the attached protocol. The microbial cells after the transformation were cultured for recovery in YPD medium at 30° C. overnight. Then, the microbial cells were collected, applied onto YPD agar medium containing 300 mg/L of hygromycin (from Nacalai Tesque, Product Number 07296-24), and cultured at 30° C. for two days. Using the obtained trans-

TABLE 9

Sequences of primers used for construction of pUC57-AOX3-Hyg[R]

| Primer name | Nucleotide sequence (5'-3') | SEQ ID NO |
|---|---|---|
| AOX3_insert_F | 5'GCTATACGAAGTTATACCCTCCTTGACAGTCTTGACGTG3' | SEQ ID NO: 81 |
| AOX3_insert_R | 5'ATTATACGAAGTTATCGCGGCCGCTGCAGGATATC3' | SEQ ID NO: 82 |
| AOX3_backbone_F | 5'GGGAGGCTTACCAGAAGATTAACTGTTAG3' | SEQ ID NO: 83 |
| AOX3_backbone_R | 5'CGAGCTTCGTAGGAGGGCATATAAC3' | SEQ ID NO: 84 |
| pUC57_F | 5'CCTCTTCGCTATTACGCCAGCTG3' | SEQ ID NO: 85 |
| pUC57_R | 5'CCCAGGCTTTACACTTTATGCTTCCG3' | SEQ ID NO: 86 |

<Construction of Yarrowia lipolytica W29ΔURA3ΔAOX3 Strain>

Next, PCR (PrimeSTAR GXL (registered trade name), 98° C. for 10 seconds, 55° C. for 5 seconds and 72° C. for 240 seconds, 40 cycles) was performed using plasmid DNA of pUC57-AOX3-Hyg[R] as the template and using primers AOX3_del_F (SEQ ID NO:88) and AOX3_del_R (SEQ ID NO:89). To remove template DNA in the obtained PCR product, the PCR product was digested with the restriction formant, colony PCR (KOD FX (registered trade name) Neo DNA polymerase, 98° C. for 10 seconds, 55° C. for 30 seconds, 68° C. for 120 seconds, 40 cycles) was performed using primers AOX3_check_F (SEQ ID NO:90) and AOX3_check_R (SEQ ID NO:91) to confirm destruction of the AOX3 gene. Sequences of the primers used for the construction of W29ΔURA3ΔAOX3 strain are shown in Table 10.

TABLE 10

Sequences of primers used for construction of W29ΔURA3ΔAOX3 strain

| Primer name | Nucleotide sequence (5'-3') | SEQ ID NO |
|---|---|---|
| AOX3_del_F | 5'TAGTGTTTTTGTTGGTTTTTATTTGATTTGTTGG3' | SEQ ID NO: 88 |
| AOX3_del_R | 5'GCTCATTTTCGGTCTCCAAACTGATTCTC3' | SEQ ID NO: 89 |

TABLE 10-continued

Sequences of primers used for construction of W29ΔURA3ΔAOX3 strain

| Primer name | Nucleotide sequence (5'-3') | SEQ ID NO |
|---|---|---|
| AOX3_check_F | 5'GAACGGTTCGACCCAGTCACGTG3' | SEQ ID NO: 90 |
| AOX3_check_R | 5'ACCCTCCTTGACAGTCTTGACGTG3' | SEQ ID NO: 91 |

<Study on Producing δ-Decalactone from 13-HOD Utilizing *Y. lipolytica* W29ΔURA3ΔAOX3 Strain>

W29ΔURA3ΔAOX3 strain obtained above was inoculated in 10 mL of YPD medium in a test tube, and cultured with shaking at 30° C. for 20 hours to obtain precultured medium B. 7.5 mL of the precultured medium was inoculated to 50 mL of induction medium in a 500 mL flask, and cultured with shaking under the condition at 30° C. and at 120 rpm for 20 hours. A composition of the induction medium and a preparation method thereof are shown in Table 11. Microbial cells were collected by centrifuging the obtained culture medium (1000 G, 5 minutes, 4° C.). Subsequently, the microbial cells were washed twice with phosphate buffer (137 mM NaCl, 8.1 mM $Na_2HPO_4$, 2.68 mM KCl, 1.47 mM $KH_2PO_4$) to use for the conversion reaction.

TABLE 11

Composition of induction medium and preparation method thereof

| Composition | Amount of component |
|---|---|
| Stock solution B | 929 mL |
| 10 g/L $FeSO_4$ | 1 mL |
| 50 mg/L $ZnCl_2$ | 10 mL |
| 156 mg/L $CuSO_4$ | 10 mL |
| 10% Glucose | 50 mL |
| Oleic acid | 7 g |

A stock solution B was prepared by the following procedure. 0.1 g of Yeast extract, 2.1 g of $KH_2PO_4$, 4.51 g of $K_2HPO_4$, 0.1 g of NaCl, and 0.2 g of $MgSO_4$ were dissolved in purified water and diluted to 929 mL. Then, the solution was sterilized by the autoclave at 120° C. for 15 minutes. Solutions of 10 g/L $FeSO_4$, 50 mg/L $ZnCl_2$, and 156 mg/L $CuSO_4$ were prepared, respectively, and sterilized by filtrating through the 0.22 μm filter. 1 mL of the $FeSO_4$ solution, 10 mL of the $ZnCl_2$ solution, 10 mL of the $CuSO_4$ solution and 50 mL of glucose were added to 929 mL of the cooled stock solution B. Subsequently, 7 g of oleic acid was also added to the stock solution B to use as the induction medium.

Phosphate buffer was prepared by the following procedure. 80 g of NaCl, 2 g of KCl, 22 g of $Na_2HPO_4.7H_2O$, and 2 g of $KH_2PO_4$ were dissolved in purified water, diluted to 1 L, and then sterilized by the autoclave at 120° C. for 15 minutes to use as a 10 times concentration stock solution. This stock solution was diluted 10 times to use as the phosphate buffer.

The culture medium after culturing a bacterial strain that expressed each 13-LAH according to the method described above was used as the culture medium containing 13-HOD. W29ΔURA3ΔAOX3 strain was inoculated to this culture medium so that bacterial cells were about 4.2 g DCW (dry cell weight)/L based on this culture medium, and cultured with shaking under the condition at 30° C. and at 120 rpm for 6 hours. When DCW was calculated, a value obtained by multiplying a value at $OD_{600}$ by 0.197 was used. δ-decalactone in the reaction solution was analyzed as follows. 0.2 mL of the culture medium after the conversion reaction was placed in a 1.5 mL tube with cap lock, then 20 μL of a 2 N HCl solution and 0.6 mL of ethyl acetate were added thereto, and the mixture was mixed on the vortex for 10 seconds. This mixture was centrifuged at 15,000 rpm at 25° C. for 10 minutes. 200 μL of an ethyl acetate layer at an upper layer was collected and subjected to GC-FID analysis under the following condition. Amounts of δ-decalactone produced from the culture medium after culturing the bacterial strain that expresses each 13-LAH are shown in Table 12.

<GC-FID Analysis Condition for δ-Decalactone>

Apparatus: GC-2010 Plus (Shimadzu Corporation), column: DB-1 ms, internal diameter: 0.25 mm, length: 30 m, membrane thickness: 0.25 μm (Part Number 122-0132), injection amount: 5 μL, injection method: split 20:1, inlet: 230° C., column temperature program: starting at 90° C., then rising temperature up to 160° C. at 25° C./minute, then rising temperature up to 180° C. at 5° C./minute, then, rising temperature up to 280° C. (kept for 2.5 minutes) at 50° C./minute, carrier gas: helium, column flow: 2.0 mL/minute, detector: temperature 250° C., uptake cycle 25 Hz, makeup flow (Air) 30 mL/minute.

TABLE 12

Amounts of produced δ-decalactone when culture medium of each 13-LAH expressing strain was utilized

| Source of culture medium containing 13-HOD used | Amount of produced δ-decalactone (mg/L) |
|---|---|
| Culture medium of BLR(DE3)/pET-22b(+)$Km^R$ | Not detected |
| Culture medium of BLR(DE3)/pET-22b(+)$Km^R$ - Laci_13-LAH strain | 4.01 |
| Culture medium of BLR(DE3)/pET-22b(+)$Km^R$ - Lamy_13-LAH strain | 2.46 |
| Culture medium of BLR(DE3)/pET-22b(+)$Km^R$ - Lhel_13-LAH strain | 4.65 |
| Culture medium of BLR(DE3)/pET-22b(+)$Km^R$ - Lgal_13-LAH strain | 11.67 |
| Culture medium of BLR(DE3)/pET-22b(+)$Km^R$ - Lcri_13-LAH strain | 7.33 |
| Culture medium of BLR(DE3)/pET-22b(+)$Km^R$ - Lkef_13-LAH strain | 5.10 |
| Culture medium of BLR(DE3)/pET-22b(+)$Km^R$ - Lint_13-LAH strain | 2.19 |
| Culture medium of BLR(DE3)/pET-22b(+)$Km^R$ - Lham_13-LAH strain | 4.64 |
| Culture medium of BLR(DE3)/pET-22b(+)$Km^R$ - Lgas_13-LAH strain | 5.34 |
| Culture medium of BLR(DE3)/pET-22b(+)$Km^R$ - Pcla_13-LAH strain | 4.43 |
| Culture medium of BLR(DE3)/pET-22b(+)$Km^R$ - Lrum_13-LAH strain | 4.33 |

TABLE 12-continued

Amounts of produced δ-decalactone when culture medium of each 13-LAH expressing strain was utilized

| Source of culture medium containing 13-HOD used | Amount of produced δ-decalactone (mg/L) |
|---|---|
| Culture medium of BLR(DE3)/pET-22b(+)Km$^R$-Sinf_13-LAH strain | 4.90 |
| Culture medium of BLR(DE3)/pET-22b(+)Km$^R$-Smut_13-LAH strain | 15.68 |
| Culture medium of BLR(DE3)/pET-22b(+)Km$^R$-Sequ_13-LAH strain | 8.37 |

From analysis results of GC-FID, the production of δ-decalactone was able to be confirmed in all culture media obtained from the strains expressing various 13-LAH. As described above, it was demonstrated that the conversion to δ-decalactone could be achieved by utilizing 13-HOD obtained in this investigation.

INDUSTRIAL APPLICABILITY

The present invention is useful for producing 13-hydroxy-9(Z)-octadecenoic acid available as an intermediate of δ-decalactone and further for producing δ-decalactone.

SEQUENCE LISTING FREE TEXT

SEQ ID NO:1 sets forth an amino acid sequence of 13-LAH from *Lactobacillus acidophilus*.
SEQ ID NO:2 sets forth an amino acid sequence of 13-LAH from *Lactobacillus amylovorus*.
SEQ ID NO:3 sets forth an amino acid sequence of 13-LAH from *Lactobacillus helveticus*.
SEQ ID NO:4 sets forth an amino acid sequence of 13-LAH from *Lactobacillus gallinarum*.
SEQ ID NO:5 sets forth an amino acid sequence of 13-LAH from *Lactobacillus crispatus*.
SEQ ID NO:6 sets forth an amino acid sequence of 13-LAH from *Lactobacillus kefiranofaciens*.
SEQ ID NO:7 sets forth an amino acid sequence of 13-LAH from *Lactobacillus intestinalis*.
SEQ ID NO:8 sets forth an amino acid sequence of 13-LAH from *Lactobacillus hamsteri*.
SEQ ID NO:9 sets forth an amino acid sequence of 13-LAH from *Lactobacillus gasseri*.
SEQ ID NO:10 sets forth an amino acid sequence of 13-LAH from *Pediococcus claussenii*.
SEQ ID NO:11 sets forth an amino acid sequence of 13-LAH from *Lactobacillus ruminis*.
SEQ ID NO:12 sets forth an amino acid sequence of 13-LAH from *Streptococcus infantarius*.
SEQ ID NO:13 sets forth an amino acid sequence of 13-LAH from *Streptococcus mutans*.
SEQ ID NO:14 sets forth an amino acid sequence of 13-LAH from *Streptococcus equinus*.
SEQ ID NO:15 sets forth a nucleotide sequence of a 13-LAH gene from *Lactobacillus acidophilus* (Laci_13-LAH) and chemically synthesized.
SEQ ID NO:16 sets forth a nucleotide sequence of a 13-LAH gene from *Lactobacillus amylovorus* (Lamy_13-LAH) and chemically synthesized.
SEQ ID NO:17 sets forth a nucleotide sequence of a 13-LAH gene from *Lactobacillus helveticus* (Lhel_13-LAH) and chemically synthesized.
SEQ ID NO:18 sets forth a nucleotide sequence of a 13-LAH gene from *Lactobacillus gallinarum* (Lgal_13-LAH) and chemically synthesized.
SEQ ID NO:19 sets forth a nucleotide sequence of a 13-LAH gene from *Lactobacillus crispatus* (Lcri_13-LAH) and chemically synthesized.
SEQ ID NO:20 sets forth a nucleotide sequence of a 13-LAH gene from *Lactobacillus kefiranofaciens* (Lkef_13-LAH) and chemically synthesized.
SEQ ID NO:21 sets forth a nucleotide sequence of a 13-LAH gene from *Lactobacillus intestinalis* (Lint_13-LAH) and chemically synthesized.
SEQ ID NO:22 sets forth a nucleotide sequence of a 13-LAH gene from *Lactobacillus hamsteri* (Lham_13-LAH) and chemically synthesized.
SEQ ID NO:23 sets forth a nucleotide sequence of a 13-LAH gene from *Lactobacillus gasseri* (Lgas_13-LAH) and chemically synthesized.
SEQ ID NO:24 sets forth a nucleotide sequence of a 13-LAH gene from *Pediococcus claussenii* (Pcla_13-LAH) and chemically synthesized.
SEQ ID NO:25 sets forth a nucleotide sequence of a 13-LAH gene from *Lactobacillus ruminis* (Lrum_13-LAH) and chemically synthesized.
SEQ ID NO:26 sets forth a nucleotide sequence of a 13-LAH gene from *Streptococcus infantarius* (Sinf_13-LAH) and chemically synthesized.
SEQ ID NO:27 sets forth a nucleotide sequence of a 13-LAH gene from *Streptococcus mutans* (Smut_13-LAH) and chemically synthesized.
SEQ ID NO:28 sets forth a nucleotide sequence of a 13-LAH gene from *Streptococcus equinus* (Sequ_13-LAH) and chemically synthesized.
SEQ ID NOs:29 to 32 set forth nucleotide sequences of the primers used for the construction of pET-22b(+)Km$^R$.
SEQ ID NOs:33 to 62 set forth nucleotide sequences of the primers used for the construction of plasmids for the expression of 13-LAH.
SEQ ID NOs:63 to 76 set forth nucleotide sequences of the primers used for the construction of *Yarrowia lipolytica* W29ΔURA3 strain.
SEQ ID NO:77 sets forth a nucleotide sequence of AOX3.
SEQ ID NO:78 sets forth an amino acid sequence of AOX3.
SEQ ID NO:79 sets forth a nucleotide sequence of pUC57-AOX3-Ura.
SEQ ID NO:80 sets forth a nucleotide sequence of pUC57-TEF-Hyg$^R$.
SEQ ID NO:81 to 86 set forth nucleotide sequences of the primers used for the construction of pUC57-AOX3-Hyg$^R$.
SEQ ID NO:87 sets forth a nucleotide sequence of pUC57-AOX3-Hyg$^R$.
SEQ ID NO:88 to 91 set forth nucleotide sequences of the primers used for the construction of *Yarrowia lipolytica* W29ΔURA3ΔAOX3 strain.

The invention claimed is:

1. A method of producing 13-hydroxy-9(Z)-octadecenoic acid, comprising producing 13-hydroxy-9(Z)-octadecenoic acid from linoleic acid in the presence of a transformed microorganism that produces a protein selected from the group consisting of:
- (1A) a protein comprising the amino acid sequence of SEQ ID NO: 4;
- (1B) a protein comprising an amino acid sequence containing one to twenty amino acid substitutions, deletions, insertions or additions the amino acid sequence of SEQ ID NO: 4, and having a linoleate 13-hydratase activity;
- (1C) a protein comprising an amino acid sequence having 95% or more identity to the amino acid sequence of SEQ ID NO: 4, and having a linoleate 13-hydratase activity;
- (2A) a protein comprising the amino acid sequence of SEQ ID NO: 5;
- (2B) a protein comprising an amino acid sequence containing one to twenty amino acid substitutions, deletions, insertions or additions the amino acid sequence of SEQ ID NO: 5, and having a linoleate 13-hydratase activity;
- (2C) a protein comprising an amino acid sequence having 95% or more identity to the amino acid sequence of SEQ ID NO: 5, and having a linoleate 13-hydratase activity;
- (3A) a protein comprising the amino acid sequence of SEQ ID NO: 8;
- (3B) a protein comprising an amino acid sequence containing one to fifty amino acid substitutions, deletions, insertions or additions the amino acid sequence of SEQ ID NO: 8, and having a linoleate 13-hydratase activity;
- (3C) a protein comprising an amino acid sequence having 90% or more identity to the amino acid sequence of SEQ ID NO: 8, and having a linoleate 13-hydratase activity;
- (4A) a protein comprising the amino acid sequence of SEQ ID NO: 9;
- (4B) a protein comprising an amino acid sequence containing one to fifty amino acid substitutions, deletions, insertions or additions the amino acid sequence of SEQ ID NO: 9, and having a linoleate 13-hydratase activity;
- (4C) a protein comprising an amino acid sequence having 90% or more identity to the amino acid sequence of SEQ ID NO: 9, and having a linoleate 13-hydratase activity;
- (5A) a protein comprising the amino acid sequence of SEQ ID NO: 10;
- (5B) a protein comprising an amino acid sequence containing one to fifty amino acid substitutions, deletions, insertions or additions the amino acid sequence of SEQ ID NO: 10, and having a linoleate 13-hydratase activity;
- (5C) a protein comprising an amino acid sequence having 90% or more identity to the amino acid sequence of SEQ ID NO: 10, and having a linoleate 13-hydratase activity;
- (6A) a protein comprising the amino acid sequence of SEQ ID NO: 13;
- (6B) a protein comprising an amino acid sequence containing one to fifty amino acid substitutions, deletions, insertions or additions the amino acid sequence of SEQ ID NO: 13, and having a linoleate 13-hydratase activity;
- (6C) a protein comprising an amino acid sequence having 90% or more identity to the amino acid sequence of SEQ ID NO: 13, and having a linoleate 13-hydratase activity;
- (7A) a protein comprising the amino acid sequence of SEQ ID NO: 14;
- (7B) a protein comprising an amino acid sequence containing one to fifty amino acid substitutions, deletions, insertions or additions the amino acid sequence of SEQ ID NO: 14, and having a linoleate 13-hydratase activity; and
- (7C) a protein comprising an amino acid sequence having 90% or more identity to the amino acid sequence of SEQ ID NO: 14, and having a linoleate 13-hydratase activity.

2. The method according to claim 1, wherein said protein is the following:
- (3A) a protein comprising the amino acid sequence of SEQ ID NO: 8;
- (3B) a protein comprising an amino acid sequence containing one to fifty amino acid substitutions, deletions, insertions or additions the amino acid sequence of SEQ ID NO: 8, and having a linoleate 13-hydratase activity;
- (3C) a protein comprising an amino acid sequence having 90% or more identity to the amino acid sequence of SEQ ID NO: 8, and having a linoleate 13-hydratase activity;
- (4A) a protein comprising the amino acid sequence of SEQ ID NO: 9;
- (4B) a protein comprising an amino acid sequence containing one to fifty amino acid substitutions, deletions, insertions or additions the amino acid sequence of SEQ ID NO: 9, and having a linoleate 13-hydratase activity;
- (4C) a protein comprising an amino acid sequence having 90% or more identity to the amino acid sequence of SEQ ID NO: 9, and having a linoleate 13-hydratase activity;
- (6A) a protein comprising the amino acid sequence of SEQ ID NO: 13;
- (6B) a protein comprising an amino acid sequence containing one to fifty amino acid substitutions, deletions, insertions or additions the amino acid sequence of SEQ ID NO: 13, and having a linoleate 13-hydratase activity;
- (6C) a protein comprising an amino acid sequence having 90% or more identity to the amino acid sequence of SEQ ID NO: 13, and having a linoleate 13-hydratase activity;
- (7A) a protein comprising the amino acid sequence of SEQ ID NO: 14;
- (7B) a protein comprising an amino acid sequence containing one to fifty amino acid substitutions, deletions, insertions or additions the amino acid sequence of SEQ ID NO: 14, and having a linoleate 13-hydratase activity; and (7C) a protein comprising an amino acid sequence having 90% or more identity to the amino acid sequence of SEQ ID NO: 14, and having a linoleate 13-hydratase activity.

3. The method according to claim 1, wherein said identity is 95% or more.

4. The method according to claim 1, wherein said protein is linoleate 13-hydratase from a microorganism selected from the group consisting of *Lactobacillus gallinarum, Lactobacillus crispatus, Lactobacillus hamsteri, Lactobacillus gasseri, Pediococcus claussenii, Streptococcus mutans*, and *Streptococcus equinus*.

5. The method according to claim 4, wherein said protein is linoleate 13-hydratase from a microorganism selected from the group consisting of *Lactobacillus hamsteri, Lactobacillus gasseri, Streptococcus mutans*, and *Streptococcus equinus*.

6. The method according to claim 1, wherein said transformed microorganism is a microorganism comprising an expression unit containing a polynucleotide encoding said protein and a promoter operably linked thereto.

7. The method according to claim 1, wherein said transformed microorganism is a bacterium belonging to the genus *Escherichia*.

8. The method according to claim 7, wherein said transformed microorganism is *Escherichia coli*.

9. A method for producing δ-decalactone, comprising:
(i) producing 13-hydroxy-9(Z)-octadecenoic acid from linoleic acid in the presence of a transformed microorganism that produces a protein selected from the group consisting of:
(1A) a protein comprising the amino acid sequence of SEQ ID NO: 4;
(1B) a protein comprising an amino acid sequence containing one to twenty amino acid substitutions, deletions, insertions or additions the amino acid sequence of SEQ ID NO: 4, and having a linoleate 13-hydratase activity;
(1C) a protein comprising an amino acid sequence having 95% or more identity to the amino acid sequence of SEQ ID NO: 4, and having a linoleate 13-hydratase activity;
(2A) a protein comprising the amino acid sequence of SEQ ID NO: 5;
(2B) a protein comprising an amino acid sequence containing one to twenty amino acid substitutions, deletions, insertions or additions the amino acid sequence of SEQ ID NO: 5, and having a linoleate 13-hydratase activity;
(2C) a protein comprising an amino acid sequence having 95% or more identity to the amino acid sequence of SEQ ID NO: 5, and having a linoleate 13-hydratase activity;
(3A) a protein comprising the amino acid sequence of SEQ ID NO: 8;
(3B) a protein comprising an amino acid sequence containing one to fifty amino acid substitutions, deletions, insertions or additions the amino acid sequence of SEQ ID NO: 8, and having a linoleate 13-hydratase activity;
(3C) a protein comprising an amino acid sequence having 90% or more identity to the amino acid sequence of SEQ ID NO: 8, and having a linoleate 13-hydratase activity;
(4A) a protein comprising the amino acid sequence of SEQ ID NO: 9;
(4B) a protein comprising an amino acid sequence containing one to fifty amino acid substitutions, deletions, insertions or additions the amino acid sequence of SEQ ID NO: 9, and having a linoleate 13-hydratase activity;
(4C) a protein comprising an amino acid sequence having 90% or more identity to the amino acid sequence of SEQ ID NO: 9, and having a linoleate 13-hydratase activity;
(5A) a protein comprising the amino acid sequence of SEQ ID NO: 10;
(5B) a protein comprising an amino acid sequence containing one to fifty amino acid substitutions, deletions, insertions or additions the amino acid sequence of SEQ ID NO: 10, and having a linoleate 13-hydratase activity;
(5C) a protein comprising an amino acid sequence having 90% or more identity to the amino acid sequence of SEQ ID NO: 10, and having a linoleate 13-hydratase activity;
(6A) a protein comprising the amino acid sequence of SEQ ID NO: 13;
(6B) a protein comprising an amino acid sequence containing one to fifty amino acid substitutions, deletions, insertions or additions the amino acid sequence of SEQ ID NO: 13, and having a linoleate 13-hydratase activity;
(6C) a protein comprising an amino acid sequence having 90% or more identity to the amino acid sequence of SEQ ID NO: 13, and having a linoleate 13-hydratase activity;
(7A) a protein comprising the amino acid sequence of SEQ ID NO: 14;
(7B) a protein comprising an amino acid sequence containing one to fifty amino acid substitutions, deletions, insertions or additions the amino acid sequence of SEQ ID NO: 14, and having a linoleate 13-hydratase activity; and
(7C) a protein comprising an amino acid sequence having 90% or more identity to the amino acid sequence of SEQ ID NO: 14, and having a linoleate 13-hydratase activity; and
(ii) producing δ-decalactone from 13-hydroxy-9(Z)-octadecenoic acid.

10. The method according to claim 9, wherein (ii) is performed in the presence of a microorganism having a β oxidation activity.

11. The method according to claim 10, wherein said microorganism having the β oxidation activity is a microorganism having lowered aldehyde oxidase activity compared to an activity of a wild-type enzyme.

12. The method according to claim 11, wherein said microorganism having the β oxidation activity is *Yarrowia lipoytica*.

13. The method according to claim 1, wherein the protein is selected from the group consisting of:
(1A) a protein comprising the amino acid sequence of SEQ ID NO: 4;
(1B) a protein comprising an amino acid sequence containing one to twenty amino acid substitutions, deletions, insertions or additions the amino acid sequence of SEQ ID NO: 4, and having a linoleate 13-hydratase activity; and (1C) a protein comprising an amino acid sequence having 95% or more identity to the amino acid sequence of SEQ ID NO: 4, and having a linoleate 13-hydratase activity.

14. The method according to claim 1, wherein the protein is selected from the group consisting of:
- (2A) a protein comprising the amino acid sequence of SEQ ID NO: 5;
- (2B) a protein comprising an amino acid sequence containing one to twenty amino acid substitutions, deletions, insertions or additions the amino acid sequence of SEQ ID NO: 5, and having a linoleate 13-hydratase activity; and
- (2C) a protein comprising an amino acid sequence having 95% or more identity to the amino acid sequence of SEQ ID NO: 5, and having a linoleate 13-hydratase activity.

15. The method according to claim 1, wherein the protein is selected from the group consisting of:
- (3A) a protein comprising the amino acid sequence of SEQ ID NO: 8;
- (3B) a protein comprising an amino acid sequence containing one to fifty amino acid substitutions, deletions, insertions or additions the amino acid sequence of SEQ ID NO: 8, and having a linoleate 13-hydratase activity; and
- (3C) a protein comprising an amino acid sequence having 90% or more identity to the amino acid sequence of SEQ ID NO: 8, and having a linoleate 13-hydratase activity.

16. The method according to claim 1, wherein the protein is selected from the group consisting of:
- (4A) a protein comprising the amino acid sequence of SEQ ID NO: 9;
- (4B) a protein comprising an amino acid sequence containing one to fifty amino acid substitutions, deletions, insertions or additions the amino acid sequence of SEQ ID NO: 9, and having a linoleate 13-hydratase activity; and
- (4C) a protein comprising an amino acid sequence having 90% or more identity to the amino acid sequence of SEQ ID NO: 9, and having a linoleate 13-hydratase activity.

17. The method according to claim 1, wherein the protein is selected from the group consisting of:
- (5A) a protein comprising the amino acid sequence of SEQ ID NO: 10;
- (5B) a protein comprising an amino acid sequence containing one to fifty amino acid substitutions, deletions, insertions or additions the amino acid sequence of SEQ ID NO: 10, and having a linoleate 13-hydratase activity; and
- (5C) a protein comprising an amino acid sequence having 90% or more identity to the amino acid sequence of SEQ ID NO: 10, and having a linoleate 13-hydratase activity.

18. The method according to claim 1, wherein the protein is selected from the group consisting of:
- (6A) a protein comprising the amino acid sequence of SEQ ID NO: 13;
- (6B) a protein comprising an amino acid sequence containing one to fifty amino acid substitutions, deletions, insertions or additions the amino acid sequence of SEQ ID NO: 13, and having a linoleate 13-hydratase activity; and
- (6C) a protein comprising an amino acid sequence having 90% or more identity to the amino acid sequence of SEQ ID NO: 13, and having a linoleate 13-hydratase activity.

19. The method according to claim 1, wherein the protein is selected from the group consisting of:
- (7A) a protein comprising the amino acid sequence of SEQ ID NO: 14;
- (7B) a protein comprising an amino acid sequence containing one to fifty amino acid substitutions, deletions, insertions or additions the amino acid sequence of SEQ ID NO: 14, and having a linoleate 13-hydratase activity; and
- (7C) a protein comprising an amino acid sequence having 90% or more identity to the amino acid sequence of SEQ ID NO: 14, and having a linoleate 13-hydratase activity.

20. The method according to claim 1, wherein the protein is selected from the group consisting of:
- (A) a protein comprising an amino acid sequence selected from the group consisting of SEQ ID NOs: 4, 5, 8 to 10, 13, and 14;
- (B) a protein comprising an amino acid sequence containing one to twenty amino acid substitutions, deletions, insertions or additions in an amino acid sequence selected from the group consisting of SEQ ID NOs: 4, 5, 8 to 10, 13, and 14, and having a linoleate 13-hydratase activity; and
- (C) a protein comprising an amino acid sequence having 95% or more identity to an amino acid sequence selected from the group consisting of SEQ ID NOs: 4, 5, 8 to 10, 13, and 14, and having a linoleate 13-hydratase activity.

* * * * *